(12) United States Patent
Galley et al.

(10) Patent No.: US 7,253,158 B2
(45) Date of Patent: Aug. 7, 2007

(54) SULFONAMIDES

(75) Inventors: Guido Galley, Rheinfelden (DE); Eric Argirios Kitas, Aesch (CH); Roland Jakob-Roetne, Inzlingen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 32 days.

(21) Appl. No.: 11/179,703

(22) Filed: Jul. 12, 2005

(65) Prior Publication Data

US 2006/0014945 A1    Jan. 19, 2006

(30) Foreign Application Priority Data

Jul. 13, 2004    (EP) .................. 04103339

(51) Int. Cl.
  *C07D 223/08* (2006.01)
  *A61K 31/55* (2006.01)
  *A61P 35/00* (2006.01)
  *A61P 25/28* (2006.01)

(52) U.S. Cl. .................. 514/212.03; 514/212.08; 540/524; 540/527

(58) Field of Classification Search ........... 540/524, 540/527; 514/212.03, 212.08
  See application file for complete search history.

(56) References Cited

U.S. PATENT DOCUMENTS

| 6,107,291 A | 8/2000 | Russo-Rodriguez et al. |
| 2005/0165003 A1* | 7/2005 | Neitzel et al. ......... 514/212.08 |

FOREIGN PATENT DOCUMENTS

| WO | WO 03/066592 | 8/2003 |
| WO | WO 2004/080983 | 9/2004 |
| WO | WO 2005/042489 | 5/2005 |

OTHER PUBLICATIONS

Sisodia, S. S. et al., Nature Reviews/Neuroscience, vol. 3, Apr. 2002, 281-290.
Wolfe, M. S. et al., Current Topics in Medicinal Chemistry, 2002, 2, 371-383.
Tsai, J. Y. et al., Current Medicinal Chemistry, 2002, vol. 9, No. 11, 1087-1106.
Sambamurti, K. et al., Drug Development Research, 56, 211-227, 2002.
May, P.C., Drug Discovery Today, vol. 6, No. 9, May 2001, 459-462.
Nunan, J. et al., FEBS Letters, 483, (2000), 6-10.
Hardy, J. et al., Science, vol. 297, 353-356, Jul. 2002.
Wolfe, M.S., Journal of Medicinal Chemistry, vol. 44, No.13, 2001, 2039-2060.
Haass, C., The EMBO Journal (2004), 23, 483-488.
Fraering, P. C. et al., Biochemistry (2004), 43 (30), 9774-9789.
Herreman, A. H. et al., Nature Cell Biology 2, 461-462, 2000.
De Strooper, B. et al., Nature 398, 518-522, 1999.
Chung, H. M. et al., Nature Cell Biology 3, 1129-1132, 2001.
Hadland, B. K. et al., PNAS 98, 7487-7491, 2001.
Ferrando, A. A. et al., Cancer Cell 1, 75-87, 2002.
Weng, A. P. et al., Science 306, 269-271, 2004.
Weng, A. P. et al., Mol Cell Biol 23, 655-664, 2003.
Weijzen, S. et al., Nature Medicine 8, 979-986, 2002.
Nickoloff, B. J. et al., Oncogene 22, 6598-6608, 2003.

* cited by examiner

*Primary Examiner*—Bruck Kifle
(74) *Attorney, Agent, or Firm*—George W. Johnston; Patricia S. Rocha-Tramaloni; Kimberly J. Prior

(57) ABSTRACT

The invention relates to compounds of the general formula

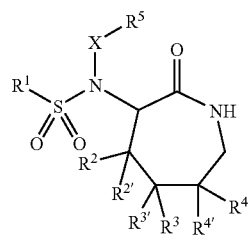

I in which $R^1$, $R^2$, R3, $R^4$, $R^{2'}$, R3', $R^{4'}$, $R^5$, and X is —CHR— are as defined in the specification. The invention also provides pharmaceutically acceptable acid addition salts, optically pure enantiomers, racemates and diastereomeric mixtures of such compounds. The invention further provides methods for the treatment of Alzheimer's disease or common cancers.

12 Claims, No Drawings

SULFONAMIDES

BACKGROUND OF THE INVENTION

Alzheimer's disease (AD) is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length.

Abeta peptides are produced from APP through the sequential action of 2 proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. The majority of Abeta peptides is of 40 amino acids length (Aβ40), a minor species carries 2 additional amino acids at its C-terminus. The latter is supposed to be the more pathogenic amyloid peptide.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substates and which are themselves polytopic membrane proteins. Other essential components of γ-secretase may be presenilin, nicastrin and the products of the aph1 and pen-2 genes. Proven substrates for γ-secretase are the APP and the proteins of the Notch receptor family, however, γ-secretase has a loose substrate specificity and may cleave further membrane proteins unrelated to APP and Notch. It was demonstrated by genetic means, i.e., ablation of either the presenilin 1 and 2 genes or the nicastrin gene, that γ-secretase is absolutely required for Notch signaling. This was subsequently confirmed by treatment with specific γ-secretase inhibitors.

Notch receptors are not only essential in embryonal development but also play a critical role in several tissues of the adult organism which continue to undergo proliferation and differentiation, e.g., hematopoietic cells and epithelia of the gut and skin. The signaling of Notch receptors occurs through an ordered sequence of events: binding to a ligand of the Delta or Jagged group, cleavage of the extracellular domain by an ADAM protease (TACE) and subsequent cleavage by the γ-secretase within the Notch transmembrane domain. The latter cleavage results in the liberation of the cytoplasmic domain which then translocates to the nucleus where it acts with other proteins as a regulator of a specific group of genes.

A role for Notch in human oncogenesis was most dearly established for T-cell Acute Lymphoblastic Leukemia (T-ALL). Some rare cases of T-ALL show a (7:9) chromosomal translocation which leads to a constitutive activation of Notch1. Recently it was reported that ca. 50% of all T-ALL cases have point mutation in the Notch1 receptor which also cause over-activation. It was shown that growth of some cell lines derived from such leukemias were sensitive to treatment with γ-secretase inhibitors which confirmed an essential role for Notch1 signaling.

A broader role for Notch in oncogenesis is discussed in several recent paper which descibe that its signaling is required for maintaining the neoplastic phenotype in ras-transformed cells. Deregulation of the ras-signaling pathway is found in a number of common cancers including cervical carcinomas and breast carcinomas.

The γ-secretase activity is absolutely required for the production of Abeta peptides. This has been shown both by genetic means, i.e., ablation of the presenilin genes and by low-molecular-weight inhibitory compounds. Since according to the amyloid hypothesis of AD the production and deposition of Abeta is the ultimate cause for the disease, it is thought that selective and potent inhibitors of γ-secretase will be useful for the prevention and treatment of AD.

Numerous documents describe the current knowledge on γ-secretase inhibition, for example the following publications:

The EMBO Journal (2204), 23, 483-488,
Biochemistry (2004), 43 (30), 9774-9789,
Nature Reviews/Neuroscience, Vol. 3, April 2002/281,
Biochemical Society Transactions (2002), Vol. 30. part 4,
Current Topics in Medicinal Chemistry, 2002, 2, 371-383,
Current Medicinal Chemistry, 2002, Vol. 9, No. 11, 1087-1106,
Drug Development Research, 56, 211-227, 2002,
Drug Discovery Today, Vol. 6, No. 9, May 2001, 459-462,
FEBS Letters, 483, (2000), 6-10,
Science, Vol. 297, 353-356, July 2002,
Journal. of Medicinal Chemistry, Vol. 44, No. 13, 2001, 2039-2060,
Nature Cell Biology 2, 461-462, 2000,
Nature 398, 518-522, 1999,
Nature Cell Biology 3, 1129-1132, 2001,
PNAS 98, 7487-7491, 2001,
Cancer Cell 1, 75-87, 2002,
Science 306, 269-271, 2004,
Mol Cell Biol 23, 655-664, 2003,
Nature Medicine 8, 979-986, 2002 and
Oncogene 22, 6598-6608, 2003.

SUMMARY OF THE INVENTION

The invention provides sulfonamides and methods of preparing them. It also provides pharmaceutical compositions containing the sulfonamides and methods of preparing such compositions. It has been found that the compounds of general formula I are γ-secretase inhibitors. Thus, the compounds of this invention will be useful treating AD or common cancers by blocking the activity of γ-secretase and reducing or preventing the formation of the various amyloidogenic Abeta peptides and furthermore, by blocking the Notch signaling pathways they can interfere with cancer pathogenesis.

The invention further provides methods for treating Alzheimer's disease and for treating common cancers including but not limited to cervical carcinomas, breast carcinomas and malignancies of the hematopoietic system.

In particular, the invention provides compounds of formula I

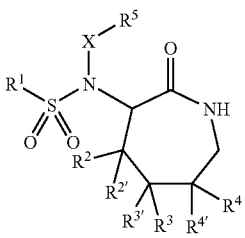

wherein
R[1] is aryl or heteroaryl, each of which is unsubstituted or substituted by one or more substituents selected from the group consisting of halogen, lower alkyl, lower alkyl substituted by halogen, O-lower alkyl substituted by halogen, $NO_2$ and CN;
R[2], R[3], R[4], R[2'], R[3'], and R[4'] are each indpendently hydrogen, lower alkyl, phenyl or lower alkyl substituted by halogen;
R[5] is aryl or heteroaryl, each of which is unsubstituted or substituted by one or more substituents selected from the group consisting of
halogen,
lower alkyl,
lower alkoxy,
CN,
nitro,
amino,
hydroxy,
lower alkyl substituted by hydroxy, and
lower alkyl substituted by halogen,
or is aryl or heteroaryl each of which is substituted by
—C(O)—NR"$_2$,
—(CR$_2$)$_m$—C(O)—R',
—(CH$_2$)$_m$-heterocycloalkyl,
—(CH$_2$)$_m$-heteroaryl which is unsubstituted or substituted by —(CH$_2$)$_m$-lower alkoxy, lower alkyl, —(CH$_2$)$_m$—O-benzyl or CH$_2$OH,
—C—(O)-lower alkyl,
—O—C(O)—NR$_2$,
—O—(CH$_2$)$_m$—C(O)OH,
—O-lower alkinyl,
—O-lower alkyl substituted by halogen,
—O—(CH$_2$)$_m$-heterocyclyl,
—O—(CH$_2$)$_m$-phenyl which is unsubstituted or substituted by hydroxy,
—O—(CH$_2$)$_m$-heteroaryl which is unsubstituted or substituted by lower alkyl,
—(CH$_2$)$_m$—NH—C(O)R',
—(CH$_2$)$_m$—NH—S(O)$_2$—R',
—S(O)$_2$-lower alkyl,
—S(O)$_2$-heterocyclyl, or
—S(O)$_2$NH-cycloalkyl,
or is cycloalkyl;
R' is hydrogen, lower alkyl, lower alkinyloxy, hydroxy, cycloalkyl, heterocycloalkyl which is unsubstituted or substituted by one or more substituents selected from COOH, —C(O)O-lower alkyl, —CH$_2$C(O)O-lower alkyl, halogen and lower alkyl, or is phenyl, benzyl, heteroaryl, —(CH$_2$)$_m$-lower alkoxy or —(CHR)$_m$—C(O)O-lower alkyl;
R" is hydrogen, cycloalkyl which is unsubstituted or substituted by one or more halogen atoms, lower alkyl, lower alkyl substituted by halogen, lower alkyl substituted by hydroxy, —(CH$_2$)$_m$-heterocycloalkyl, —NR$_2$, heteroaryl, benzyl or
—(CHR)$_m$—C(O)O-lower alkyl;
R is hydrogen or lower alkyl;
R[6] is hydrogen or lower alkyl;
X is —CHR—; and
m is 0, 1, 2 or 3;

and to a pharmaceutically acceptable acid addition salt thereof. The invention also provides all forms of optically pure enantiomers, recemates and diastereomeric mixtures of the compounds of the invention.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkenyl" denotes a straight- or branched chain group containing from 2 to 7 carbon atoms, wherein at least one bond is a double bond for example, ethenyl, propenyl, isopropenyl, n-butenyl, i-butenyl, and the like.

As used herein, the term "lower alkinyl" denotes a straight- or branched-chain group containing from 2 to 7 carbon atoms, wherein at least one bond is a triple bond for example, ethinyl, propinyl, isopropenyl, n-butinyl, i-butinyl and the like.

The term "lower alkoxy" or lower alkinyloxy" denotes a group wherein the alkyl or alkinyl residues is as defined above, and which is attached via an oxygen atom. The term "O-lower alkyl" is synonymous with lower alkoxy.

The term "halogen" denotes chlorine, iodine, fluorine and bromine.

The term "aryl" denotes a cyclic aromatic hydrocarbon radical which may contain one or more fused rings in which at least one ring is aromatic in nature, for example phenyl, benzyl, naphthyl or biphenyl. The preferred aryl group is phenyl.

The term "heteroaryl" denotes an aromatic cyclic radical, which may contain one or more fused rings in which at least one ring is aromatic in nature, and wherein the ring(s) may contain one to three heteroatoms, for example pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl or isoxazolyl. Preferred heteroaryl groups are pyridyl, thienyl, triazinyl, furyl and thiazolyl.

The term "heterocycloalkyl" denotes a non aromatic hydrocarbon radical, for example oxetanyl, tetrahydrofuranyl, tetrahydropyranyl, azetidinyl, pyrrolidinyl, piperidinyl, piperazinyl, morpholinyl or thiomorpholinyl. Preferred heterocycloalkyl groups are morpholinyl, piperidinyl and pyrrolidinyl.

The term "cycloalkyl" denotes a saturated carbocyclic ring, containing 3-7 carbon atoms.

The term "pharmaceutically acceptable," such as pharmaceutically acceptable carrier, excipient, etc., denotes pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" means an amount that is effective to prevent, alleviate or ameliorate symptoms of disease or prolong the survival of the subject being treated.

The invention provides compounds of formula I

I wherein
$R^1$ is aryl or heteroaryl, each of which is unsubstituted or substituted by one or more substituents selected from the group consisting of halogen, lower alkyl, lower alkyl substituted by halogen, O-lower alkyl substituted by halogen, $NO_2$ and CN;
$R^2$, $R^3$, $R^4$, $R^{2'}$, $R^{3'}$, and $R^{4'}$ are each indpendently hydrogen, lower alkyl, phenyl or lower alkyl substituted by halogen;
$R^5$ is aryl or heteroaryl, each of which is unsubstituted or substituted by one or more substituents selected from the group consisting of
halogen,
lower alkyl,
lower alkoxy,
CN,
nitro,
amino,
hydroxy,
lower alkyl substituted by hydroxy, and
lower alkyl substituted by halogen,
or is aryl or heteroaryl substituted by
—C(O)—NR''$_2$,
—(CR$_2$)$_m$—C(O)—R',
—(CH$_2$)$_m$-heterocycloalkyl,
—(CH$_2$)$_m$-heteroaryl which is unsubstituted or substituted by —(CH$_2$)$_m$-lower alkoxy, lower alkyl, —(CH$_2$)$_m$—O-benzyl or CH$_2$OH,
—O—C(O)-lower alkyl,
—O—C(O)—NR$_2$,
—O—(CH$_2$)$_m$—C(O)OH,
—O-lower alkinyl,
—O-lower alkyl substituted by halogen,
—O—(CH$_2$)$_m$-heterocyclyl,
—O—(CH$_2$)$_m$-phenyl which is unsubstituted or substituted by hydroxy,
—O—(CH$_2$)$_m$-heteroaryl which is unsubstituted or substituted by lower alkyl,
—(CH$_2$)$_m$—NH—C(O)R',
—(CH$_2$)$_m$—NH—S(O)$_2$—R',
—S(O)$_2$-lower alkyl,
—S(O)$_2$-heterocyclyl, or
—S(O)$_2$NH-cycloalkyl,
or is cycloalkyl;
R' is hydrogen, lower alkyl, lower alkinyloxy, hydroxy, cycloalkyl, heterocycloalkyl which is unsubstituted or substituted by one or more substituents selected from COOH, —C(O)O-lower alkyl, —CH$_2$C(O)O-lower alkyl, halogen and lower alkyl, or is phenyl, benzyl, heteroaryl, —(CH$_2$)$_m$-lower alkoxy or —(CHR)$_m$—C(O)O-lower alkyl;
R'' is hydrogen, cycloalkyl which is unsubstituted or substituted by one or more halogen atoms, lower alkyl, lower alkyl substituted by halogen, lower alkyl substituted by hydroxy, —(CH$_2$)$_m$-heterocycloalkyl, —NR$_2$, heteroaryl, benzyl or
—(CHR)$_m$—C(O)O-lower alkyl;
R is hydrogen or lower alkyl;
$R^6$ is hydrogen or lower alkyl;
X is —CHR—; and
m is 0, 1, 2 or 3;

and to a pharmaceutically acceptable acid addition salt, optically pure enantiomer, racemate, or diasteriomeric thereof.

In particular, the invention relates also to compounds of formula II

II wherein
$R^1$ is aryl or heteroaryl, each of which is unsubstituted or substituted by one or more substituents selected from the group consisting of halogen, CF$_3$, OCF$_3$, NO$_2$ and CN;
$R^2$, $R^3$, $R^4$, $R^{2'}$, $R^{3'}$, and $R^{4'}$ are hydrogen, lower alkyl or CF$_3$;
$R^5$ is cycloalkyl, aryl or heteroaryl, wherein cycloalkyl, aryl and heteroaryl are each independently unsubstituted or substituted by one or more substituents selected from the group consisting of
halogen,
lower alkyl,
CHO,
CN,
hydroxy,
lower alkyloxy,
lower alkinyloxy,
—OCF$_3$,
OCHF$_2$,
OCH$_2$F,
—OC(O)-lower alkyl,
—OC(O)—NR'R'',
—O—(CH$_2$)$_n$-heterocycloalkyl,
—O—(CH$_2$)$_n$-heteroaryl which is unsubstituted or substituted by lower alkyl, —O—(CH$_2$)$_n$-aryl,
—(CH$_2$)$_n$—C(O)NR'R",
—(CH$_2$)$_n$—C(O)O-lower alkyl,
—(CH$_2$)$_n$—C(O)OH,
—(CH$_2$)$_n$—C(O)O-lower alkinyl,
—C(O)-heterocycloalkyl, optionally substituted by COOH,
—C(O)-cycloalkyl,
—C(O)-aryl,
—NR'R",
nitro,
—S(O)$_2$-lower alkyl,
—S(O)$_2$-cycloalkyl,
—S(O)$_2$-heterocycloalkyl,
—S(O)$_2$-aryl, and
S(O)$_2$—NR'R",
or is

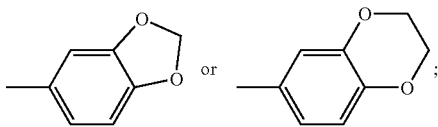

R' and R" are each independently hydrogen, lower alkyl, cycloalkyl, heterocycloalkyl, heteroaryl, di-lower alkylamino, —CH$_2$CF$_3$, —CH$_2$CHF$_2$, —CH$_2$CH$_2$F, —C(O)-lower alkyl, —C(O)O-lower alkyl or —C(O)-cycloalkyl;
X is a bond, lower alkyl or lower alkenyl;
n is 0, 1, 2 or 3;

and to a pharmaceutically acceptable acid addition salt, optically pure enantiomer, racemate or diastereomeric mixture thereof.

The most preferred compounds of formula I are those, wherein
R$^1$ is phenyl substituted by halogen and R$^5$ is phenyl substituted by —C(O)—NR"$_2$, for example the following compounds:
4-{[(4-chloro-benzenesulfonyl)-((R)-2-oxo-azepan-3-yl)-amino]-methyl}-benzamide,
4-{[(4-chloro-benzenesulfonyl)-(5-isopropyl-2-oxo-azepan-3-yl)-amino]-methyl}-benzamide,
rac-4-{[(4-chloro-benzenesulfonyl)-(5-isopropyl-2-oxo-azepan-3-yl)-amino]-methyl}-N-cyclopropyl-benzamide,
rac-4-{[(4-chloro-benzenesulfonyl)-(2-oxo-azepan-3-yl)-amino]-methyl}-N-cyclopropyl-benzamide,
4-{[(4-chloro-benzenesulfonyl)-(2-oxo-5-phenyl-azepan-3-yl)-amino]-methyl}-N-cyclopropyl-benzamide,
5-{[(4-chloro-benzenesulfonyl)-(5-isopropyl-2-oxo-azepan-3-yl)-amino]-methyl}-pyridine-2-carboxylic acid cyclopropylamide,
N-cyclopropyl-4-{[((R)-2-oxo-azepan-3-yl)-(4-bromo-benzenesulfonyl)-amino]-methyl}-benzamide,
4-{[(5-tert-butyl-2-oxo-azepan-3-yl)-(4-chloro-benzenesulfonyl)-amino]-methyl}-N-cyclopropyl-benzamide,
4-{[(4-chloro-benzenesulfonyl)-(5,5-dimethyl-2-oxo-azepan-3-yl)-amino]-methyl}-N-cyclopropyl-benzamide,
4-{[(4-chloro-benzenesulfonyl)-(2-oxo-5-trifluoromethyl-azepan-3-yl)-amino]-methyl}-N-cyclopropyl-benzamide,
rac-4-{[(4-chloro-benzenesulfonyl)-(5,5-dimethyl-2-oxo-azepan-3-yl)-amino]-methyl}-N-(2-fluoro-ethyl)-benzamide,
rac-4-{[(4-chloro-benzenesulfonyl)-(5,5-dimethyl-2-oxo-azepan-3-yl)-amino]-methyl}-N-(2,2,2-trifluoro-ethyl)-benzamide,
rac-4-{[(4-chloro-benzenesulfonyl)-(5,5-dimethyl-2-oxo-azepan-3-yl)-amino]-methyl}-N-((1R,2S)-2-fluoro-cyclopropyl)-benzamide,
rac-4-{[(4-chloro-benzenesulfonyl)-(5,5-dimethyl-2-oxo-azepan-3-yl)-amino]-methyl}-N-(2-hydroxy-ethyl)-benzamide,
rac-4-{[(4-chloro-benzenesulfonyl)-(5,5-dimethyl-2-oxo-azepan-3-yl)-amino]-methyl}-N-cyclopentyl-benzamide,
rac-4-{[(4-chloro-benzenesulfonyl)-(5,5-dimethyl-2-oxo-azepan-3-yl)-amino]-methyl}-N-methyl-benzamide,
rac-4-{[(4-chloro-benzenesulfonyl)-(5,5-dimethyl-2-oxo-azepan-3-yl)-amino]-methyl}-benzamide,
rac-N-benzyl-4-{[(4-chloro-benzenesulfonyl)-(5,5-dimethyl-2-oxo-azepan-3-yl)-amino]-methyl}-benzamide,
rac-(4-{[(4-chloro-benzenesulfonyl)-(5,5-dimethyl-2-oxo-azepan-3-yl)-amino]-methyl}-benzoylamino)-acetic acid methyl ester,
rac-4-{[(4-chloro-benzenesulfonyl)-(5,5-dimethyl-2-oxo-azepan-3-yl)-amino]-methyl}-N-(2-morpholin-4-yl-ethyl)-benzamide,
4-{[(4-chloro-benzenesulfonyl)-((R)-5,5-dimethyl-2-oxo-azepan-3-yl)-amino]-methyl}-N-cyclopropyl-benzamide,
4-chloro-N-[4-(N',N'-dimethyl-hydrazinocarbonyl)-2-fluoro-benzyl]-N-((R)-5,5-dimethyl-2-oxo-azepan-3-yl)-benzenesulfonamide and
4-chloro-N-[4-(N',N'-dimethyl-hydrazinocarbonyl)-benzyl]-N-(2-oxo-5-trifluoromethyl-azepan-3-yl)-benzenesulfonamide.

Further preferred are compounds, wherein R$^1$ is phenyl substituted by halogen or by lower alkyl substituted by halogen and R$^5$ is phenyl substituted by halogen or by lower alkyl substituted by halogen, or by CH$_2$OH, or by halogen and lower alkoxy, for example the following compounds:
rac-4-chloro-N-(4-chloro-benzyl)-N-(2-oxo-azepan-3-yl)-benzenesulfonamide,
rac-4-chloro-N-(3-fluoro-4-methoxy-benzyl)-N-(2-oxo-azepan-3-yl)-benzenesulfonamide,
rac-4-chloro-N-(4-methoxy-benzyl)-N-(2-oxo-azepan-3-yl)-benzenesulfonamide,
rac-4-Chloro-N-(3,4-dichloro-benzyl)-N-(2-oxo-azepan-3-yl)-benzenesulfonamide,
4-chloro-N-(3-fluoro-4-methoxy-benzyl)-N-((R)-2-oxo-azepan-3-yl)-benzenesulfonamide,
rac-4-bromo-N-(3-fluoro-4-methoxy-benzyl)-N-(2-oxo-azepan-3-yl)-benzenesulfonamide,
4-chloro-N-(2-fluoro-4-methoxy-benzyl)-N-((R)-2-oxo-azepan-3-yl)-benzenesulfonamide,
4-chloro-N-(3-fluoro-4-methoxy-benzyl)-N-(5-isopropyl-2-oxo-azepan-3-yl)-benzenesulfonamide,
N-(2,3-difluoro-4-methoxy-benzyl)-N-((R)-2-oxo-azepan-3-yl)-4-trifluoromethyl-benzenesulfonamide,
Rac-4-chloro-N-(4-difluoromethyl-benzyl)-N-(2-oxo-azepan-3-yl)-benzenesulfonamide
4-chloro-N-((R)-5,5-dimethyl-2-oxo-azepan-3-yl)-N-(2-fluoro-4-methoxy-benzyl)-benzenesulfonamide,
4-chloro-N-((R)-5,5-dimethyl-2-oxo-azepan-3-yl)-N-(2-fluoro-4-hydroxymethyl-benzyl)-benzenesulfonamide,
4-chloro-N-(2-fluoro-4-methoxy-benzyl)-N-(2-oxo-5-trifluoromethyl-azepan-3-yl)-benzenesulfonamide and
4-chloro-N-(2,3-difluoro-4-methoxy-benzyl)-N-((R)-2-oxo-azepan-3-yl)-benzenesulfonamide.

Further preferred are compounds, wherein R$^1$ is phenyl substituted by halogen and R$^5$ is phenyl substituted by —(CR$_2$)$_m$—C(O)—R' or by —(CR$_2$)$_m$—C(O)—R' and halogen, for example the following compounds:
4-{[(4-chloro-benzenesulfonyl)-((R)-2-oxo-azepan-3-yl)-amino]-methyl}-3-fluoro-benzoic acid methyl ester, 4-{[(4-chloro-benzenesulfonyl)-((R)-2-oxo-azepan-3-yl)-amino]-methyl}-benzoic acid ethyl ester,
4-{1-[(4-chloro-benzenesulfonyl)-((R)-2-oxo-azepan-3-yl)-amino]-ethyl}-benzoic acid methyl ester,
rac-4-{[(4-chloro-benzenesulfonyl)-(2-oxo-azepan-3-yl)-amino]-methyl}-benzoic acid methyl ester,
4-{[(4-chloro-benzenesulfonyl)-(5-isopropyl-2-oxo-azepan-3-yl)-amino]-methyl}-benzoic acid methyl ester,
Rac-4-{[(4-chloro-benzenesulfonyl)-(5,5-dimethyl-2-oxo-azepan-3-yl)-amino]-methyl}-benzoic acid methyl ester,
4-{[(4-chloro-benzenesulfonyl)-(5,5-dimethyl-2-oxo-azepan-3-yl)-amino]-methyl}-benzoic acid,
4-{[(4-chloro-benzenesulfonyl)-((R)-5,5-dimethyl-2-oxo-azepan-3-yl)-amino]-methyl}-3-fluoro-benzoic acid methyl ester,
3-(4-{[(4-chloro-benzenesulfonyl)-((R)-5,5-dimethyl-2-oxo-azepan-3-yl)-amino]-methyl}-phenyl)-propionic acid methyl ester,
3-(4-{[(4-chloro-benzenesulfonyl)-((R)-5,5-dimethyl-2-oxo-azepan-3-yl)-amino]-methyl}-phenyl)-propionic acid,
4-{[(4-chloro-benzenesulfonyl)-((R)-5,5-dimethyl-2-oxo-azepan-3-yl)-amino]-methyl}-3-fluoro-benzoic acid,
3-(4-{[(4-chloro-benzenesulfonyl)-(2-oxo-5-trifluoromethyl-azepan-3-yl)-amino]-methyl}-phenyl)-propionic acid,
4-{[(4-chloro-benzenesulfonyl)-(2-oxo-5-trifluoromethyl-azepan-3-yl)-amino]-methyl}-3-fluoro-benzoic acid methyl ester,
4-{[(4-chloro-benzenesulfonyl)-(2-oxo-5-trifluoromethyl-azepan-3-yl)-amino]-methyl}-3-fluoro-benzoic acid,
3-(4-{[(4-chloro-benzenesulfonyl)-((R)-2-oxo-azepan-3-yl)-amino]-methyl}-phenyl)-propionic acid,
rac-4-{[(4-chloro-benzenesulfonyl)-(2-oxo-azepan-3-yl)-amino]-methyl}-3-fluoro-benzoic acid methyl ester,
3-(4-{[(4-chloro-benzenesulfonyl)-((R)-2-oxo-azepan-3-yl)-amino]-methyl}-phenyl)-3-methyl-butyric acid and
3-(4-{[(4-chloro-benzenesulfonyl)-((R)-2-oxo-azepan-3-yl)-amino]-methyl}-phenyl)-2,2-dimethyl-propionic acid.

Further preferred are compounds, wherein $R^1$ is phenyl substituted by halogen and $R^5$ is phenyl substituted by hydroxy, for example the following compounds:
rac-4-chloro-N-(4-hydroxy-benzyl)-N-(2-oxo-azepan-3-yl)-benzenesulfonamide and
4-chloro-N-(4-hydroxy-benzyl)-N-((R)-2-oxo-azepan-3-yl)-benzenesulfonamide.

Further preferred are compounds, wherein $R^1$ is heteroaryl unsubstituted or substituted by one or more substituents as described in formula I, for example the following compounds:
rac-4-chloro-N-(5,5-dimethyl-2-oxo-azepan-3-yl)-N-[4-(2H-tetrazol-5-yl)-benzyl]-benzenesulfonamide,
4-chloro-N-(5-isopropyl-2-oxo-azepan-3-yl)-N-[4-(5-methyl-[1,3,4]oxadiazol-2-yl)-benzyl]-benzenesulfonamide,
4-chloro-N-(5-isopropyl-2-oxo-azepan-3-yl)-N-[4-(3-methyl-[1,2,4]oxadiazol-5-yl)-benzyl]-benzenesulfonamide,
4-chloro-N-((R)-5,5-dimethyl-2-oxo-azepan-3-yl)-N-(4-isoxazol-5-yl-benzyl)-benzenesulfonamide,
4-chloro-N-(4-isoxazol-5-yl-benzyl)-N-((R)-2-oxo-azepan-3-yl)-benzenesulfonamide and
4-Chloro-N-[2-fluoro-4-(2H-[1,2,4]triazol-3-yl)-benzyl]-N-((R)-2-oxo-azepan-3-yl)-benzenesulfonamide.

Further preferred are compounds, wherein $R^1$ is phenyl substituted by halogen and $R^5$ is phenyl substituted by $NH_2$, for example the following compound:
N-(4-amino-benzyl)-4-chloro-N-((R)-2-oxo-azepan-3-yl)-benzenesulfonamide.

Further preferred are compounds, wherein $R^1$ is phenyl substituted by halogen and $R^5$ is phenyl substituted by —$(CH_2)_m$—NH—C(O)R', for example the following compounds:
rac-N-(4-{[(4-chloro-benzenesulfonyl)-(5,5-dimethyl-2-oxo-azepan-3-yl)-amino]-methyl}-phenyl)-acetamide and
Rac-N-(4-{[(4-chloro-benzenesulfonyl)-(2-oxo-azepan-3-yl)-amino]-methyl}-phenyl)-malonamic acid ethyl ester.

Preferred are further those compounds, wherein X is —$CH_2$—.

Further preferred are compounds, wherein $R^1$ is aryl and $R^5$ is aryl.

The present compounds of formula I and their pharmaceutically acceptable salts can be prepared by methods known in the art, for example, by processes described below, which processes comprise a) reacting a compound of formula

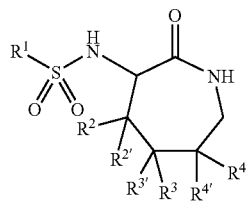

IV with a compound of formula
$R^5$X-hal in the presence of a base, or with a compound of formula
$R^5$XOH in the presence of diethylazodicarboxylate and tripenylphosphine to produce a compound of formula

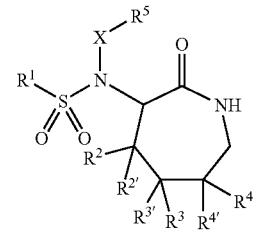

I wherein $R^1$-$R^5$ and X have the meaning as described in the definitions for compounds of formula I above, or b) reacting a compound of formula

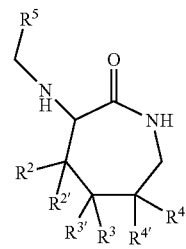

III with a compound of formula
$R^1$—S(O)$_2$—Cl in the presence of a base to produce a compound of formula

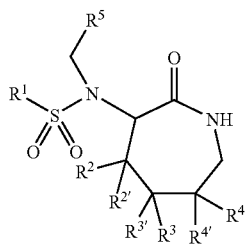

wherein $R^1$-$R^5$ and X have the meaning as described in the definitions for compounds of formula I above, and if desired, converting the compounds obtained into pharmaceutically acceptable acid addition salts.

The detailed processes for preparing of compounds of formula I are described in schemes 1 and 2 and in Examples 1-223. The starting materials of formulae II, VI, $R^1$—S(O)$_2$Cl, $R^5$Xhal, $R^5$X—OH or HOSO$_3$NH$_2$ are known compounds or can be prepared by methods well-known in the art.

Scheme 1

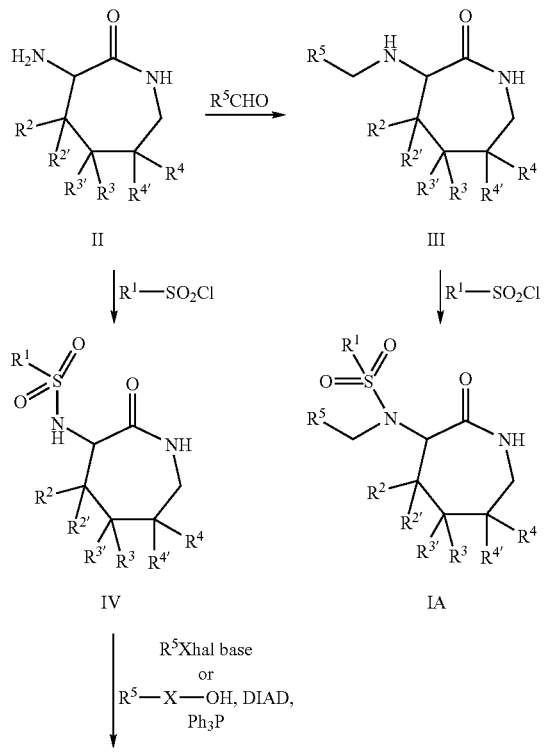

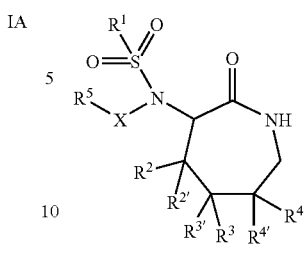

wherein $R^1$-$R^5$ and X have the meaning as described above, DIAD is diethylazodicarboxylate and Ph$_3$P is tripenylphosphine.

An amino-azepan-2-one of formula II is treated with an aldehyde and a suitable reducing reagent such as sodium triacetoxyborohydride or sodium cyanoborohydride to yield an amine compound of formula III. A solution of this amine in dichloromethane can be reacted with one equivalent of an aromatic sulfonyl chloride in the presence of a base such as Hünig's base or triethylamine and catalytic DMAP to yield after column chromatography a pure compound of formula IA. Alternatively, the compound of formula II can be reacted first with the sulfonyl chloride resulting in sulfonamide compounds of formula IV which are amenable to further derivatization using for example a Mitsunobu protocol whereby an alcohol $R^5$XOH, triphenylphosphine and diisopropyl or diethyl azodicarboxylate are reacted at low temperature under an inert atmosphere in a dry solvent such as tetrahydrofuran. The reaction mixture is allowed to warm up and further stirred at room temperature for several hours to furnish after column chromatography compounds of formula I. Intermediates of formula IV can also be used in a reaction where a halide $R^5$Xhal in the presence of excess potassium carbonate, catalytic potassium iodide in dry DMF solvent and at an elevated temperature are reacted. The reaction mixture is then filtered, acidified and purified using column chromatography to give compounds of formula I.

An unsubstituted amino-azepan-2-one (II) can for example be prepared from the corresponding lysine hydrochloride in toluene under refluxing conditions in the presence of a base such as hexamethyldisilazane. Ring-substituted 3-amino-azepan-2-ones can be prepared by numerous methods described in the literature and specifically by one approach outlined in Scheme 2.

Scheme 2

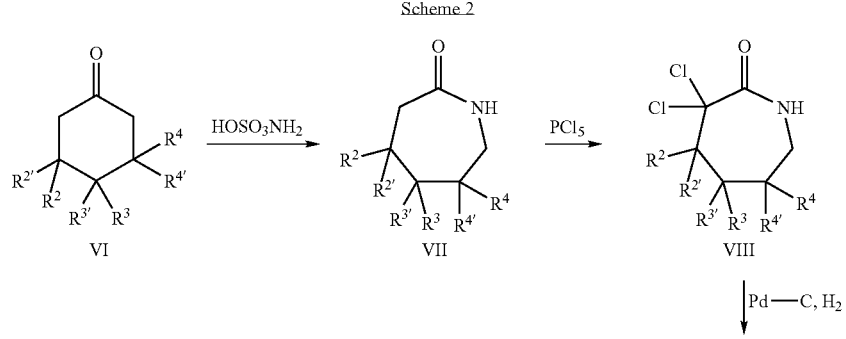

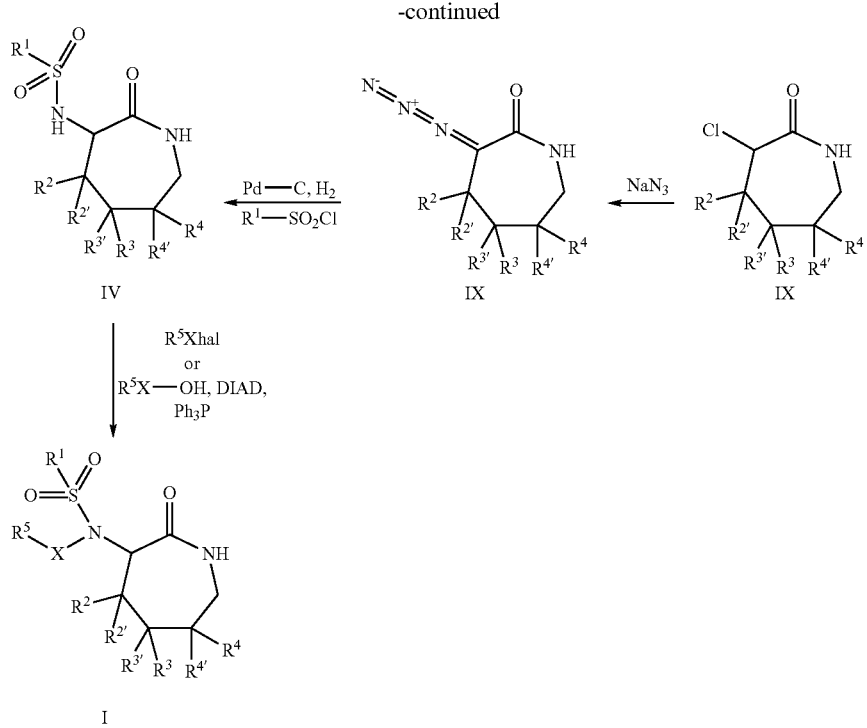

wherein $R^1$-$R^5$ and X have the meaning as described above, DIAD is diethylazodicarboxylate and $Ph_3P$ is triphenylphosphine.

A substituted cyclohexanone of formula VI can be reacted with hydroxylamine O-sulfonic acid in formic acid as solvent under refluxing conditions for several hours to yield a ring expansion product of formula VII. Such cyclic amides can be chlorinated using phosphorous pentachloride in xylenes by slowly warming the reaction mixture to 90° C. in an exothermic reaction whereby the evolution of HCl gas is also observed. After careful quenching with water at lower temperature the organic phase is isolated in an appropriate organic solvent such as chloroform, which is dried and a crude compound of formula VIII is isolated ready to be used in the next step. Monodechlorination of a compound of formula VIII can be achieved under conditions of controlled hydrogenation using palladium catalyst in acetic acid as solvent yielding compound of formula IX which can undergo substitution reaction with sodium azide as a nucleophile in preferably dry dimethylsulfoxide as solvent. Azides of compound formula X can be isolated in pure form following chromatographic purification on silica gel. Hydrogenation of azides X to the amine tend to proceed quantitatively, however owing to the instability of the amine on storage, we preferred to derivatize in situ with an appropriate aryl sulfonyl chloride to yield stable sulfonamides of compound formula IV. These can be further subjected to a Mitsunobu protocol as described before to yield target compounds of formula I.

The detailed description can be found in Examples 1-223.

If compounds of Formula I are basic, they may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention may inhibit the γ-secretase.

The compounds were investigated in accordance with the test given hereinafter.

Description of γ-Secretase Assay

The activity of test compounds can be evaluated in assays which measure the proteolytic cleavage of suitable substrates by γ-secretase activity. These can be cellular assays where e.g., a substrate of the γ-secretase is fused in its cytoplasmic domain to a transcription factor. Cells are transfected with this fusion gene and a reporter gene, e.g., firefly luciferase, which expression is enhanced by the transcription factor. Cleavage of the fused substrate by γ-secretase will lead to expression of the reporter gene which can be monitored in appropriate assays. The γ-secretase activity can also be determined in cell-free in vitro assays where e.g., a cell lysate containing the γ-secretase complex is incubated with a suitable APP-derived substrate which is cleaved to the Abeta peptides. The amount of produced peptides can be determined with specific ELISA assays. Cell lines of neuronal origin secrete Abeta peptides which can be measured with the specific ELISA assay. Treatment with compounds which inhibit γ-secretase leads to a reduction of secreted Abeta thus providing a measure of inhibition.

The in vitro assay of γ-secretase activity uses a HEK293 membrane fraction as a source of γ-secretase and a recombinant APP substrate. Latter consist of the C-terminal 100 amino acids of human APP fused to a 6× Histidin tail for purification which is expressed in *E. coli* in a regulatable expression vector, e.g. pEt15. This recombinant protein corresponds to the truncated APP fragment which results after γ-secretase cleavage of the extracellular domain and which constitutes the γ-secretase substrate. The assay principle is described in Li Y M et al, PNAS 97(11), 6138-6143 (2000). Hek293 cells are mechanically disrupted and the microsomal fraction is isolated by differential centrifugation. The membranes are solubilized in detergent (0.25% CHAPSO) and incubated with the APP substrate. The Abeta peptides which are produced by γ-secretase cleavage of the substrate are detected by specific ELISA assays as described (Brockhaus M et al, Neuroreport 9(7), 1481-1486 (1998)).

The preferred compounds show a $IC_{50} < 0.3$ μM. In the list below are described some data to the γ-secretase inhibition:

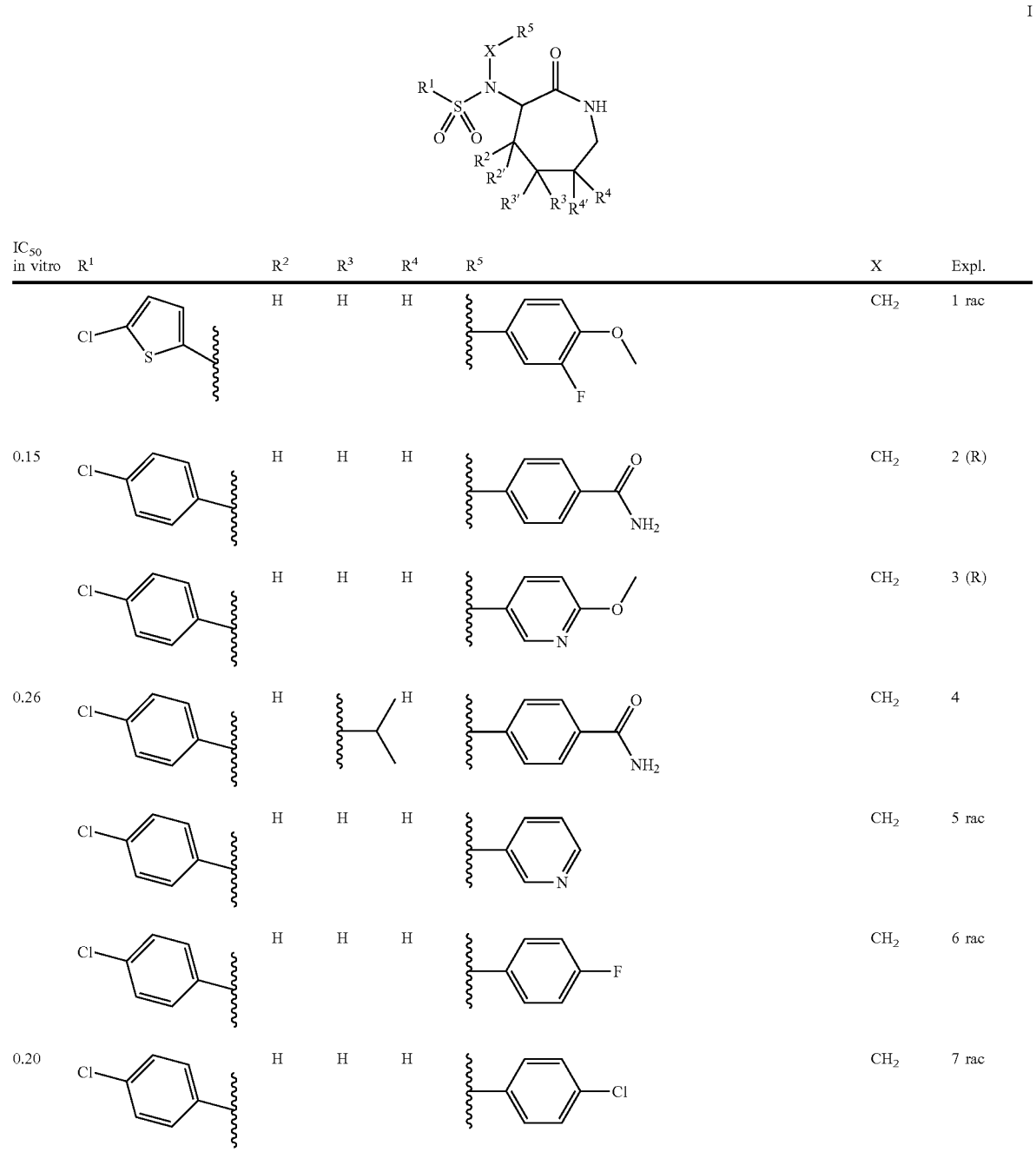

-continued

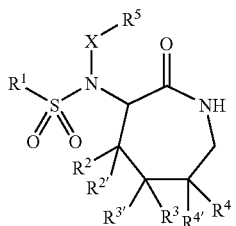

I

| IC$_{50}$ in vitro | R$^1$ | R$^2$ | R$^3$ | R$^4$ | R$^5$ | X | Expl. |
|---|---|---|---|---|---|---|---|
| 0.12 | 4-Cl-C$_6$H$_4$ | H | H | H | 3-F-4-MeO-C$_6$H$_3$ | CH$_2$ | 8 rac |
|  | 4-Cl-C$_6$H$_4$ | H | H | H | 3,4-diF-C$_6$H$_3$ | CH$_2$ | 9 rac |
| 0.15 | 4-Cl-C$_6$H$_4$ | H | H | H | 4-MeO-C$_6$H$_4$ | CH$_2$ | 10 rac |
|  | 4-Cl-C$_6$H$_4$ | H | H | H | 3,5-diF-4-MeO-C$_6$H$_2$ | CH$_2$ | 11 (R) |
| 0.08 | 4-Cl-C$_6$H$_4$ | H | H | H | 3,4-diCl-C$_6$H$_3$ | CH$_2$ | 12 rac |
|  | 4-Cl-C$_6$H$_4$ | H | H | H | 6-(Me$_2$NC(O)O)-pyridin-3-yl | CH$_2$ | 13 rac |
|  | 4-Cl-C$_6$H$_4$ | H | H | H | 6-Cl-pyridin-3-yl | CH$_2$ | 14 rac |
|  | 4-Cl-C$_6$H$_4$ | H | H | H | 6-F-pyridin-3-yl | CH$_2$ | 15 rac |
|  | 4-Cl-C$_6$H$_4$ | H | H | H | 5-Cl-pyridin-2-yl | CH$_2$ | 16 rac |

-continued
I
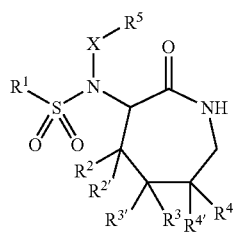
| IC$_{50}$ in vitro | R$^1$ | R$^2$ | R$^3$ | R$^4$ | R$^5$ | X | Expl. |
|---|---|---|---|---|---|---|---|
| | 4-Cl-C$_6$H$_4$ | H | H | H | 4-(OAc)-C$_6$H$_4$ | CH$_2$ | 17 rac |
| | 4-Cl-C$_6$H$_4$ | H | H | H | 4-(O-CH$_2$-C≡CH)-C$_6$H$_4$ | CH$_2$ | 18 rac |
| | 4-Cl-C$_6$H$_4$ | H | H | H | 3-F-4-CH$_3$-C$_6$H$_3$ | CH$_2$ | 19 rac |
| | 4-Cl-C$_6$H$_4$ | H | H | H | 3-F-4-Cl-C$_6$H$_3$ | CH$_2$ | 20 rac |
| | 4-Cl-C$_6$H$_4$ | H | H | H | 4-(OCHF$_2$)-C$_6$H$_4$ | CH$_2$ | 21 rac |
| | 4-Cl-C$_6$H$_4$ | H | H | H | 3-F-4-(O-CH$_2$CH$_2$-morpholinyl)-C$_6$H$_3$ | CH$_2$ | 22 rac |
| | 4-Cl-C$_6$H$_4$ | H | H | H | 4-(CONH$_2$)-C$_6$H$_4$ | CH$_2$ | 23 rac |
| | 4-Cl-C$_6$H$_4$ | H | H | H | 3-OMe-4-Cl-C$_6$H$_3$ | CH$_2$ | 24 rac |

-continued
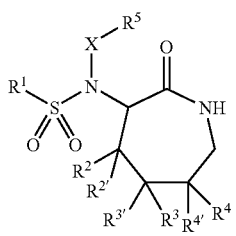
I
| IC$_{50}$ in vitro | R$^1$ | R$^2$ | R$^3$ | R$^4$ | R$^5$ | X | Expl. |
|---|---|---|---|---|---|---|---|
| 0.13 | 4-Cl-C$_6$H$_4$ | H | H | H | 3-F-4-MeO-C$_6$H$_3$ | CH$_2$ | 25 (R) |
|  | 4-Cl-C$_6$H$_4$ | H | H | H | 3,4-Cl$_2$-C$_6$H$_3$ | CH$_2$ | 26 (R) |
|  | 4-Cl-C$_6$H$_4$ | H | H | H | 4-OAc-C$_6$H$_4$ | CH$_2$ | 27 (R) |
| 0.15 | 4-Br-C$_6$H$_4$ | H | H | H | 3-F-4-MeO-C$_6$H$_3$ | CH$_2$ | 28 rac |
|  | 4-Cl-C$_6$H$_4$ | H | H | H | 3-MeO-C$_6$H$_4$ | CH$_2$ | 29 rac |
|  | 4-Cl-C$_6$H$_4$ | H | H | H | 5,6-Cl$_2$-pyridin-3-yl | CH$_2$ | 30 rac |
|  | 4-Cl-C$_6$H$_4$ | H | H | H | 4-EtO-C$_6$H$_4$ | CH$_2$ | 31 rac |
|  | 4-Cl-C$_6$H$_4$ | H | H | H | 2,5-F$_2$-C$_6$H$_3$ | CH$_2$ | 32 rac |

-continued

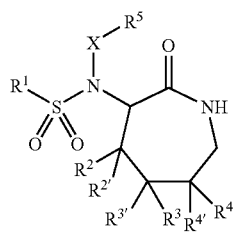

I

| IC$_{50}$ in vitro | R$^1$ | R$^2$ | R$^3$ | R$^4$ | R$^5$ | X | Expl. |
|---|---|---|---|---|---|---|---|
|  | 4-Cl-phenyl | H | H | H | 2,4,5-trifluorophenyl | CH$_2$ | 33 rac |
| 0.14 | 4-Cl-phenyl | H | H | H | 3-fluoro-4-(methoxycarbonyl)phenyl | CH$_2$ | 34 (R) |
| 0.09 | 4-Cl-phenyl | H | H | H | 4-(ethoxycarbonyl)phenyl | CH$_2$ | 35 (R) |
|  | 4-Cl-phenyl | H | H | H | 4-(methoxycarbonylmethyl)phenyl | CH$_2$ | 36 (R) |
|  | 4-Cl-phenyl | H | H | H | 4-carboxyphenyl | CH$_2$ | 37 (R, S) |
|  | 4-Cl-phenyl | H | H | H | 4-(prop-2-ynyloxycarbonyl)phenyl | CH$_2$ | 38 (R) |
|  | 4-Cl-phenyl | H | H | H | 4-(2-methoxycarbonylethyl)phenyl | CH$_2$ | 39 (R) |
|  | 4-Cl-phenyl | H | H | H | 6-chloropyridin-3-yl | CH$_2$ | 40 (R) |

-continued

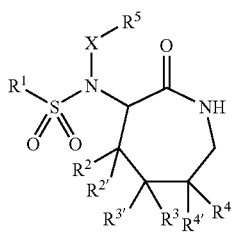

I

| IC₅₀ in vitro | R¹ | R² | R³ | R⁴ | R⁵ | X | Expl. |
|---|---|---|---|---|---|---|---|
| 0.20 | 4-Cl-C₆H₄- | H | H | H | 4-(methoxycarbonyl)phenyl | CH(CH₃) | 41 (R) |
|  | 4-Cl-C₆H₄- | H | iPr | H | 6-methoxypyridin-3-yl | CH₂ | 42 rac |
| 0.03 | 4-Cl-C₆H₄- | H | iPr | H | 4-(cyclopropylcarbamoyl)phenyl | CH₂ | 43 rac |
|  | 4-Cl-C₆H₄- | H | iPr | H | 6-methylpyridin-3-yl | CH₂ | 44 rac |
|  | 4-Cl-C₆H₄- | H | iPr | H | 4-(difluoromethoxy)phenyl | CH₂ | 45 rac |
|  | 4-Cl-C₆H₄- | H | H | H | 2-methylphenyl | CH₂ | 46 rac |
|  | 4-Cl-C₆H₄- | H | H | H | 3-methylphenyl | CH₂ | 47 rac |
|  | 4-Cl-C₆H₄- | H | H | H | 4-methylphenyl | CH₂ | 48 rac |
|  | 4-Cl-C₆H₄- | H | H | H | 2-chlorophenyl | CH₂ | 49 rac |

-continued
I
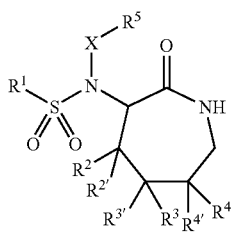
| IC$_{50}$ in vitro | R$^1$ | R$^2$ | R$^3$ | R$^4$ | R$^5$ | X | Expl. |
|---|---|---|---|---|---|---|---|
|  | 4-Cl-C$_6$H$_4$ | H | H | H | 3-Cl-C$_6$H$_4$ | CH$_2$ | 50 rac |
|  | 4-Cl-C$_6$H$_4$ | H | H | H | 2-F-C$_6$H$_4$ | CH$_2$ | 51 rac |
|  | 4-Cl-C$_6$H$_4$ | H | H | H | 3-F-C$_6$H$_4$ | CH$_2$ | 52 rac |
|  | 4-Cl-C$_6$H$_4$ | H | H | H | 3-OCF$_3$-C$_6$H$_4$ | CH$_2$ | 53 rac |
|  | 4-Cl-C$_6$H$_4$ | H | H | H | 4-OCF$_3$-C$_6$H$_4$ | CH$_2$ | 54 rac |
|  | 4-Cl-C$_6$H$_4$ | H | H | H | 3-F-4-CN-C$_6$H$_3$ | CH$_2$ | 55 (R) |
| 0.08 | 4-Cl-C$_6$H$_4$ | H | H | H | 3-F-4-(1,2,4-triazol-3-yl)-C$_6$H$_3$ | CH$_2$ | 56 (R) |
| 0.13 | 4-Cl-C$_6$H$_4$ | H | H | H | 4-CO$_2$Me-C$_6$H$_4$ | CH$_2$ | 57 rac |

-continued
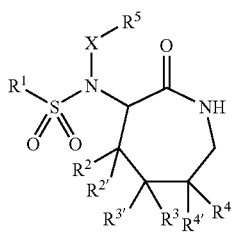
I
| IC$_{50}$ in vitro | R$^1$ | R$^2$ | R$^3$ | R$^4$ | R$^5$ | X | Expl. |
|---|---|---|---|---|---|---|---|
| | 4-Cl-phenyl | H | H | H | 4-(NHC(O)CH$_3$)-phenyl | CH$_2$ | 58 rac |
| | 4-Cl-phenyl | H | H | H | 4-(S(O)$_2$CH$_3$)-phenyl | CH$_2$ | 59 rac |
| | 4-Cl-phenyl | H | H | H | 4-(C(O)N(Et)$_2$)-phenyl | CH$_2$ | 60 rac |
| 0.28 | 4-Cl-phenyl | H | H | H | 4-OH-phenyl | CH$_2$ | 61 rac |
| | 4-Cl-phenyl | H | H | H | 4-(NHC(O)OEt)-phenyl | CH$_2$ | 62 rac |
| | 4-Cl-phenyl | H | H | H | 4-(C(O)-piperidinyl)-phenyl | CH$_2$ | 63 rac |
| | 4-Cl-phenyl | H | H | H | 4-(C(O)OCH$_2$C≡CH)-phenyl | CH$_2$ | 64 rac |
| | 4-Cl-phenyl | H | H | H | 4-CHO-phenyl | CH$_2$ | 65 rac |

-continued

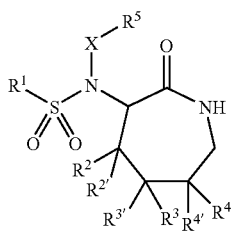

| IC$_{50}$ in vitro | R$^1$ | R$^2$ | R$^3$ | R$^4$ | R$^5$ | X | Expl. |
|---|---|---|---|---|---|---|---|
|  | 4-Cl-C$_6$H$_4$ | H | H | H | 4-(pyrrolidin-1-ylsulfonyl)phenyl | CH$_2$ | 66 rac |
|  | 4-Cl-C$_6$H$_4$ | H | H | H | 2-fluoro-4-methoxyphenyl | CH$_2$ | 67 rac |
| 0.12 | 4-Cl-C$_6$H$_4$ | H | H | H | 2-fluoro-4-methoxyphenyl | CH$_2$ | 68 R |
| 0.06 | 4-Cl-C$_6$H$_4$ | H | H | H | 4-hydroxyphenyl | CH$_2$ | 69 R |
|  | 4-Cl-C$_6$H$_4$ | H | H | H | 4-[(4-hydroxybenzyl)oxy]phenyl | CH$_2$ | 70 (R) |
|  | 4-Cl-C$_6$H$_4$ | H | H | H | 4-carboxyphenyl | CH$_2$ | 71 rac |
|  | 4-Cl-C$_6$H$_4$ | H | H | H | phenyl | CH$_2$ | 72 rac |
|  | 4-Cl-C$_6$H$_4$ | H | H | H | 4-(1-cyanocyclopropyl)phenyl | CH$_2$ | 73 rac |
|  | 4-Cl-C$_6$H$_4$ | H | H | H | 4-(1-methoxycarbonylcyclopropyl)phenyl | CH$_2$ | 74 rac |

-continued

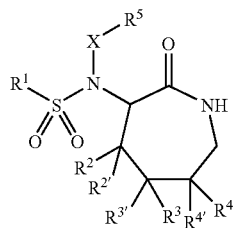

| IC$_{50}$ in vitro | R$^1$ | R$^2$ | R$^3$ | R$^4$ | R$^5$ | X | Expl. |
|---|---|---|---|---|---|---|---|
| 0.19 | 4-Cl-C$_6$H$_4$- | H | H | H | 4-(cyclopropylaminocarbonyl)phenyl | CH$_2$ | 75 rac |
|  | 4-Cl-C$_6$H$_4$- | H | H | H | 4-(methylaminocarbonyl)phenyl | CH$_2$ | 76 rac |
|  | 4-Cl-C$_6$H$_4$- | H | H | H | 4-(2,2,2-trifluoroethylaminocarbonyl)phenyl | CH$_2$ | 77 rac |
|  | 4-Cl-C$_6$H$_4$- | H | H | H | 4-(morpholin-4-ylaminocarbonyl)phenyl | CH$_2$ | 78 rac |
|  | 4-Cl-C$_6$H$_4$- | H | H | H | 4-(N',N'-dimethylhydrazidocarbonyl)phenyl | CH$_2$ | 79 rac |
|  | 4-Cl-C$_6$H$_4$- | H | H | H | 4-(pyrrolidin-1-ylaminocarbonyl)phenyl | CH$_2$ | 80 rac |
|  | 4-Cl-C$_6$H$_4$- | H | H | H | 4-(piperidin-1-ylaminocarbonyl)cyclohexa-1,4-dienyl | CH$_2$ | 81 rac |
|  | 4-Cl-C$_6$H$_4$- | H | H | H | 4-(1-methoxycarbonylcyclopropyl)phenyl | CH$_2$ | 82 (R) |
|  | 4-Cl-C$_6$H$_4$- | H | H | H | 4-(methoxycarbonylmethyl)phenyl | CH$_2$ | 83 (R) |

-continued

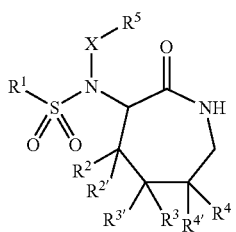

I

| IC$_{50}$ in vitro | R$^1$ | R$^2$ | R$^3$ | R$^4$ | R$^5$ | X | Expl. |
|---|---|---|---|---|---|---|---|
| | 4-Cl-phenyl | H | H | H | 4-nitrophenyl | CH$_2$ | 84 (R) |
| | thien-2-yl | H | H | H | 3-fluoro-4-methoxyphenyl | CH$_2$ | 85 rac |
| | 5-bromothien-2-yl | H | H | H | 3-fluoro-4-methoxyphenyl | CH$_2$ | 86 rac |
| | 4,5-dichlorothien-2-yl | H | H | H | 3-fluoro-4-methoxyphenyl | CH$_2$ | 87 rac |
| | 5-chloro-4-nitrothien-2-yl | H | H | H | 3-fluoro-4-methoxyphenyl | CH$_2$ | 88 rac |
| | 5-chloro-3-bromothien-2-yl | H | H | H | 3-fluoro-4-methoxyphenyl | CH$_2$ | 89 rac |
| | 5-methyl-2-(trifluoromethyl)furan-3-yl | H | H | H | 3-fluoro-4-methoxyphenyl | CH$_2$ | 90 rac |

-continued

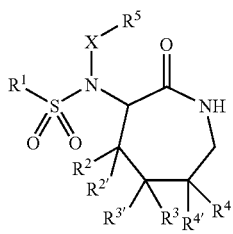

I

| IC$_{50}$ in vitro | R$^1$ | R$^2$ | R$^3$ | R$^4$ | R$^5$ | X | Expl. |
|---|---|---|---|---|---|---|---|
|  | 2,5-dichlorothien-3-yl | H | H | H | 3-fluoro-4-methoxyphenyl | CH$_2$ | 91 rac |
| 0.27 | 4-chlorophenyl | H | H | H | 4-aminophenyl | CH$_2$ | 92 rac |
|  | 4-chlorophenyl | H | H | H | 4-(1-carboxycyclopropyl)phenyl | CH$_2$ | 93 (R) |
|  | 4-chlorophenyl | H | H | H | 4-(cyclopropanecarbonylamino)phenyl | CH$_2$ | 94 (R) |
|  | 4-chlorophenyl | H | H | H | benzo[1,3]dioxol-5-yl | CH$_2$ | 95 rac |
|  | 4-chlorophenyl | H | H | H | 6-methoxypyridin-3-yl | CH$_2$ | 96 rac |
|  | 4-chlorophenyl | H | H | H | 4-[2-(4-methylthiazol-5-yl)ethoxy]phenyl | CH$_2$ | 97 rac |
|  | 4-chlorophenyl | H | H | H | 4-[(4H-1,2,4-triazol-4-yl)carbamoyl]phenyl | CH$_2$ | 98 rac |

-continued

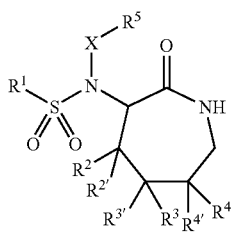

I

| IC$_{50}$ in vitro | R$^1$ | R$^2$ | R$^3$ | R$^4$ | R$^5$ | X | Expl. |
|---|---|---|---|---|---|---|---|
|  | 4-Cl-C$_6$H$_4$ | H | H | H | 2-(3-carboxypropyl)phenyl | CH(CH$_3$) | 99 rac |
|  | 4-(OCF$_3$)-C$_6$H$_4$ | H | H | H | 3-F-4-OMe-C$_6$H$_3$ | CH$_2$ | 100 rac |
|  | 4-CN-C$_6$H$_4$ | H | H | H | 3-F-4-OMe-C$_6$H$_3$ | CH$_2$ | 101 rac |
|  | 4-Cl-C$_6$H$_4$ | H | H | di-CH$_3$ | 4-(cyclopropylaminocarbonyl)phenyl | CH$_2$ | 102 |
|  | 4-Cl-C$_6$H$_4$ | H | H | H | 4-(prolyl-carbonyl)phenyl | CH$_2$ | 103 rac |
|  | 4-Cl-C$_6$H$_4$ | H | Ph | H | 4-(cyclopropylaminocarbonyl)phenyl | CH$_2$ | 104 |
|  | 4-Cl-C$_6$H$_4$ | H | iPr | H | 4-(cyclopropylaminocarbonyl)phenyl | CH$_2$ | 105 |
| 0.26 | 4-CF$_3$-C$_6$H$_4$ | H | H | H | 4-(cyclopropylaminocarbonyl)phenyl | CH$_2$ | 106 (R) |

-continued

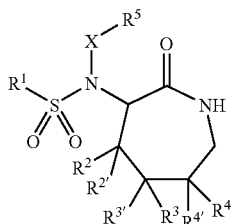
I

| IC$_{50}$ in vitro | R$^1$ | R$^2$ | R$^3$ | R$^4$ | R$^5$ | X | Expl. |
|---|---|---|---|---|---|---|---|
| 0.29 | 4-Br-C$_6$H$_4$– | H | H | H | 4-(cyclopropylaminocarbonyl)phenyl | CH$_2$ | 107 (R) |
|  | 4-Cl-C$_6$H$_4$– | H | iPr | H | 4-(cyclopropylaminocarbonyl)phenyl | CH$_2$ | 108 |
| 0.28 | 4-Cl-C$_6$H$_4$– | H | di-CH$_3$ | H | 4-(cyclopropylaminocarbonyl)phenyl | CH$_2$ | 109 |
| 0.14 | 4-Cl-C$_6$H$_4$– | H | H | H | 4-pyridyl | CH$_2$ | 110 (R) |
| 0.008 | 4-Cl-C$_6$H$_4$– | H | iPr | H | 4-methoxyphenyl | CH$_2$ | 111 |
|  | 4-Cl-C$_6$H$_4$– | H | iPr | H | 3-methoxyphenyl | CH$_2$ | 112 |
|  | 4-Cl-C$_6$H$_4$– | H | iPr | H | 4-(methoxycarbonyl)phenyl | CH$_2$ | 113 |
|  | 4-Cl-C$_6$H$_4$– | H | iPr | H | 3-fluoro-4-methoxyphenyl | CH$_2$ | 114 |
| 0.03 | 4-Cl-C$_6$H$_4$– | H | CF$_3$ | H | 4-(cyclopropylaminocarbonyl)phenyl | CH$_2$ | 115 |
| 0.14 | 4-Cl-C$_6$H$_4$– | H | iPr | H | 2-fluoro-4-methoxyphenyl | CH$_2$ | 116 |

-continued
I
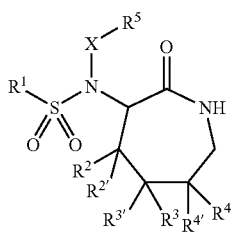
| IC$_{50}$ in vitro | R$^1$ | R$^2$ | R$^3$ | R$^4$ | R$^5$ | X | Expl. |
|---|---|---|---|---|---|---|---|
| | 4-Cl-C$_6$H$_4$ | H | H | H | 2-(methyl 4-phenylbutanoate) | CH$_2$ | 117 |
| | 4-Cl-C$_6$H$_4$ | H | H | H | 3-(methyl 4-phenylbutanoate) | CH$_2$ | 118 |
| | 4-Cl-C$_6$H$_4$ | H | H | H | 2-(4-phenylbutanoic acid) | CH$_2$ | 119 |
| | 4-Cl-C$_6$H$_4$ | H | H | H | 3-(4-phenylbutanoic acid) | CH$_2$ | 120 |
| | 4-Cl-C$_6$H$_4$ | H | H | H | 3-(methyl benzoate) | CH$_2$ | 121 rac |
| | 4-Cl-C$_6$H$_4$ | H | H | H | 3-(piperidinyl ethyl ester benzamide) | CH$_2$ | 122 rac |

-continued

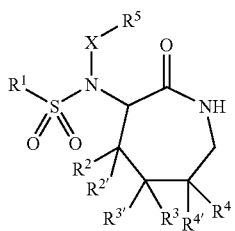

I

| IC$_{50}$ in vitro | R$^1$ | R$^2$ | R$^3$ | R$^4$ | R$^5$ | X | Expl. |
|---|---|---|---|---|---|---|---|
| | 4-Cl-C$_6$H$_4$- | H | H | H | 3-(4-ethoxycarbonyl-piperidine-1-carbonyl)-phenyl | CH$_2$ | 123 rac |
| | 4-Cl-C$_6$H$_4$- | H | H | H | 3-[(L-Val-OtBu)carbamoyl]phenyl | CH$_2$ | 124 (3S) (3RS) |
| | 4-Cl-C$_6$H$_4$- | H | H | H | 3-[(Gly-OtBu)carbamoyl]phenyl | CH$_2$ | 125 rac |
| | 4-Cl-C$_6$H$_4$- | H | H | H | 3-[(β-Ala-OtBu)carbamoyl]phenyl | CH$_2$ | 126 rac |
| | 4-Cl-C$_6$H$_4$- | H | H | H | 3-(carboxymethoxy)phenyl | CH$_2$ | 127 rac |
| | 4-Cl-C$_6$H$_4$- | H | di-CH$_3$ | H | 4-CF$_3$-C$_6$H$_4$- | CH$_2$ | 128 rac |
| | 4-Cl-C$_6$H$_4$- | H | di-CH$_3$ | H | 4-CN-C$_6$H$_4$- | CH$_2$ | 129 rac |
| | 4-Cl-C$_6$H$_4$- | H | di-CH$_3$ | H | 6-chloropyridin-3-yl | CH$_2$ | 130 rac |

-continued

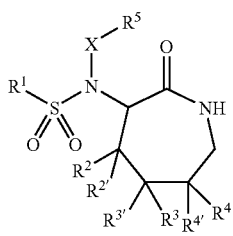

I

| IC$_{50}$ in vitro | R$^1$ | R$^2$ | R$^3$ | R$^4$ | R$^5$ | X | Expl. |
|---|---|---|---|---|---|---|---|
| | 4-Cl-phenyl | H | H | H | 3-(cyclopentylcarbamoyl)phenyl | CH$_2$ | 131 rac |
| | 4-Cl-phenyl | H | H | H | 3-(piperidin-1-ylcarbonyl)phenyl | CH$_2$ | 132 rac |
| | 4-Cl-phenyl | H | H | H | 3-(4,4-difluoropiperidin-1-ylcarbonyl)phenyl | CH$_2$ | 133 rac |
| | 4-Cl-phenyl | H | H | H | 3-(2,6-dimethylpiperidin-1-ylcarbonyl)phenyl | CH$_2$ | 134 rac |
| | 4-Cl-phenyl | H | H | H | 3-(4-fluoropiperidin-1-ylcarbonyl)phenyl | CH$_2$ | 135 rac |
| | 4-Cl-phenyl | H | H | H | 3-(3,3-difluoropiperidin-1-ylcarbonyl)phenyl | CH$_2$ | 136 rac |

-continued

I

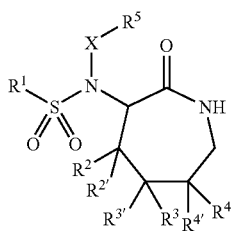

| IC$_{50}$ in vitro | R$^1$ | R$^2$ | R$^3$ | R$^4$ | R$^5$ | X | Expl. |
|---|---|---|---|---|---|---|---|
| | 4-Cl-C$_6$H$_4$ | H | H | H | 3-(3,3-difluoropyrrolidine-1-carbonyl)phenyl | CH$_2$ | 137 rac |
| 0.01 | 4-Cl-C$_6$H$_4$ | H | di-CH$_3$ | H | 4-(methoxycarbonyl)phenyl | CH$_2$ | 138 rac |
| 0.07 | 4-Cl-C$_6$H$_4$ | H | di-CH$_3$ | H | 4-carboxyphenyl | CH$_2$ | 139 |
| 0.02 | 4-Cl-C$_6$H$_4$ | H | di-CH$_3$ | H | 4-(2-fluoroethylcarbamoyl)phenyl | CH$_2$ | 140 rac |
| 0.02 | 4-Cl-C$_6$H$_4$ | H | di-CH$_3$ | H | 4-(2,2,2-trifluoroethylcarbamoyl)phenyl | CH$_2$ | 141 rac |
| 0.02 | 4-Cl-C$_6$H$_4$ | H | di-CH$_3$ | H | 4-(2-fluorocyclopropylcarbamoyl)phenyl | CH$_2$ | 142 rac |
| 0.04 | 4-Cl-C$_6$H$_4$ | H | di-CH$_3$ | H | 4-(2-hydroxyethylcarbamoyl)phenyl | CH$_2$ | 143 rac |
| 0.05 | 4-Cl-C$_6$H$_4$ | H | di-CH$_3$ | H | 4-(cyclopentylcarbamoyl)phenyl | CH$_2$ | 144 rac |
| 0.01 | 4-Cl-C$_6$H$_4$ | H | di-CH$_3$ | H | 4-(methylcarbamoyl)phenyl | CH$_2$ | 145 rac |

-continued

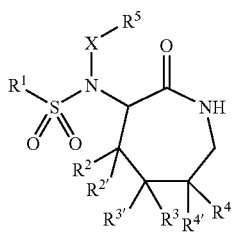

I

| IC$_{50}$ in vitro | R$^1$ | R$^2$ | R$^3$ | R$^4$ | R$^5$ | X | Expl. |
|---|---|---|---|---|---|---|---|
| 0.02 | 4-Cl-C$_6$H$_4$- | H | di-CH$_3$ | H | 4-(C(O)NH$_2$)-C$_6$H$_4$- | CH$_2$ | 146 rac |
| 0.02 | 4-Cl-C$_6$H$_4$- | H | di-CH$_3$ | H | 4-(C(O)NHCH$_2$Ph)-C$_6$H$_4$- | CH$_2$ | 147 rac |
| 0.02 | 4-Cl-C$_6$H$_4$- | H | di-CH$_3$ | H | 4-(C(O)NHCH$_2$C(O)OCH$_3$)-C$_6$H$_4$- | CH$_2$ | 148 rac |
| 0.15 | 4-Cl-C$_6$H$_4$- | H | di-CH$_3$ | H | 4-(C(O)NHCH$_2$CH$_2$-morpholinyl)-C$_6$H$_4$- | CH$_2$ | 149 rac |
| 0.10 | 4-Cl-C$_6$H$_4$- | H | di-CH$_3$ | H | 4-(tetrazol-5-yl)-C$_6$H$_4$- | CH$_2$ | 150 rac |
|  | 4-Cl-C$_6$H$_4$- | H | di-CH$_3$ | H | 4-(NHC(O)OEt)-C$_6$H$_4$- | CH$_2$ | 151 rac |
| 0.02 | 4-Cl-C$_6$H$_4$- | H | di-CH$_3$ | H | 4-(NHC(O)CH$_3$)-C$_6$H$_4$- | CH$_2$ | 152 rac |
|  | 4-CF$_3$-C$_6$H$_4$- | H | H | H | 4-(NHC(O)-cyclopropyl)-C$_6$H$_4$- | CH$_2$ | 153 rac |
|  | 4-CF$_3$-C$_6$H$_4$- | H | H | H | 4-(NHC(O)-cyclohexyl)-C$_6$H$_4$- | CH$_2$ | 154 rac |

-continued

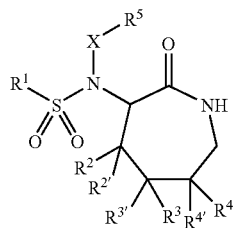

| IC$_{50}$ in vitro | R$^1$ | R$^2$ | R$^3$ | R$^4$ | R$^5$ | X | Expl. |
|---|---|---|---|---|---|---|---|
| | 4-CF$_3$-phenyl | H | H | H | 4-(NHC(O)CH$_2$OCH$_3$)-phenyl | CH$_2$ | 155 rac |
| | 4-CF$_3$-phenyl | H | H | H | 4-(NHC(O)CH$_2$C(O)OEt)-phenyl | CH$_2$ | 156 rac |
| | 4-CF$_3$-phenyl | H | H | H | 4-(NHC(O)CH$_2$Ph)-phenyl | CH$_2$ | 157 rac |
| | 4-CF$_3$-phenyl | H | H | H | 4-(NHC(O)-isoxazol-5-yl)-phenyl | CH$_2$ | 158 rac |
| | 4-CF$_3$-phenyl | H | H | H | 4-(NHC(O)Ph)-phenyl | CH$_2$ | 159 rac |
| | 4-Cl-phenyl | H | H | H | 4-(S(O)$_2$NHcyclopropyl)-phenyl | CH$_2$ | 160 rac |
| | 4-Cl-phenyl | H | H | H | 3-(NH$_2$)-phenyl | CH$_2$ | 161 rac |
| | 4-Cl-phenyl | H | H | H | 4-(NHS(O)$_2$CH$_3$)-phenyl | CH$_2$ | 162 rac |

-continued

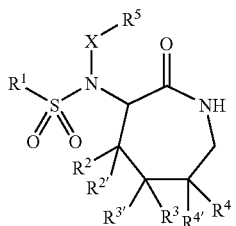

I

| IC$_{50}$ in vitro | R$^1$ | R$^2$ | R$^3$ | R$^4$ | R$^5$ | X | Expl. |
|---|---|---|---|---|---|---|---|
|  | 4-Cl-C$_6$H$_4$ | H | H | H | 3-(cyclopropylcarbonylamino)phenyl | CH$_2$ | 163 rac |
|  | 4-Cl-C$_6$H$_4$ | H | H | H | 3-(methylsulfonylamino)phenyl | CH$_2$ | 164 rac |
| 0.27 | 4-Cl-C$_6$H$_4$ | H | H | H | 4-(ethoxycarbonylacetylamino)phenyl | CH$_2$ | 165 rac |
| 0.23 | 4-CF$_3$-C$_6$H$_4$ | H | H | H | 2,3-difluoro-4-methoxyphenyl | CH$_2$ | 166 (R) |
|  | 4-CF$_3$-C$_6$H$_4$ | H | H | H | 4-(2-methoxycarbonyl-1,1-dimethylethyl)phenyl | CH$_2$ | 167 (R) |
|  | 4-CF$_3$-C$_6$H$_4$ | H | H | H | 2-fluoro-4-methoxyphenyl | CH$_2$ | 168 (R) |
|  | 4-CF$_3$-C$_6$H$_4$ | H | H | H | 4-(2-carboxy-1,1-dimethylethyl)phenyl | CH$_2$ | 169 (R) |
|  | 4-Cl-C$_6$H$_4$ | H | H | H | 4-(1H-pyrazol-1-yl)phenyl | CH$_2$ | 170 rac |

-continued

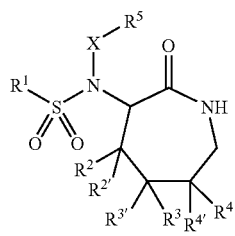

I

| IC$_{50}$ in vitro | R$^1$ | R$^2$ | R$^3$ | R$^4$ | R$^5$ | X | Expl. |
|---|---|---|---|---|---|---|---|
| | 4-Cl-C$_6$H$_4$- | H | H | H | 4-(1,2,4-triazol-1-yl)phenyl- | CH$_2$ | 171 rac |
| 0.23 | 4-Cl-C$_6$H$_4$- | H | H | H | 4-(CHF$_2$)-phenyl- | CH$_2$ | 172 rac |
| | 4-Cl-C$_6$H$_4$- | H | H | H | 4-CN-phenyl- | CH$_2$ | 173 rac |
| | 4-Cl-C$_6$H$_4$- | H | H | H | 4-[5-(CH$_2$OCH$_3$)-1,2,4-oxadiazol-3-yl]phenyl- | CH$_2$ | 174 rac |
| | 4-Cl-C$_6$H$_4$- | H | H | H | 4-(5-methyl-1,2,4-oxadiazol-3-yl)phenyl- | CH$_2$ | 175 rac |
| | 4-Cl-C$_6$H$_4$- | H | H | H | 4-[5-(CH$_2$OCH$_2$Ph)-1,2,4-oxadiazol-3-yl]phenyl- | CH$_2$ | 176 rac |
| | 4-Cl-C$_6$H$_4$- | H | H | H | 4-[5-(CH$_2$OH)-1,2,4-oxadiazol-3-yl]phenyl- | CH$_2$ | 177 |
| | 4-Cl-C$_6$H$_4$- | H | iPr | H | 4-pyridyl- | CH$_2$ | 178 |
| | 4-Cl-C$_6$H$_4$- | H | iPr | H | 4-(O-CH$_2$CH$_2$CH$_2$F)-phenyl- | CH$_2$ | 179 |
| 0.14 | 4-Cl-C$_6$H$_4$- | H | iPr | H | 4-(5-methyl-1,3,4-oxadiazol-2-yl)phenyl- | CH$_2$ | 180 |

-continued

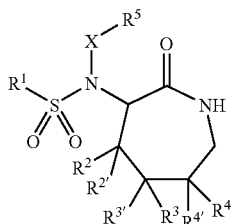

I

| IC$_{50}$ in vitro | R$^1$ | R$^2$ | R$^3$ | R$^4$ | R$^5$ | X | Expl. |
|---|---|---|---|---|---|---|---|
| 0.27 | 4-Cl-C$_6$H$_4$- | H | -CH(CH$_3$)$_2$ | H | 4-(3-methyl-1,2,4-oxadiazol-5-yl)phenyl | CH$_2$ | 181 |
|  | 4-Cl-C$_6$H$_4$- | H | -CH(CH$_3$)$_2$ | H | 4-(2-carboxyethyl)phenyl | CH$_2$ | 182 |
| 0.01 | 4-Cl-C$_6$H$_4$- | H | di-CH$_3$ | H | 4-(cyclopropylaminocarbonyl)phenyl | CH$_2$ | 183 (R) |
|  | 4-Cl-C$_6$H$_4$- | H | di-CH$_3$ | H | 4-(cyclopropylaminocarbonyl)phenyl | CH$_2$ | 184 (S) |
| 0.01 | 4-Cl-C$_6$H$_4$- | H | di-CH$_3$ | H | 3-fluoro-4-(methoxycarbonyl)phenyl | CH$_2$ | 185 (R) |
| 0.13 | 4-Cl-C$_6$H$_4$- | H | di-CH$_3$ | H | 4-(2-methoxycarbonylethyl)phenyl | CH$_2$ | 186 (R) |
| 0.01 | 4-Cl-C$_6$H$_4$- | H | di-CH$_3$ | H | 4-(2-carboxyethyl)phenyl | CH$_2$ | 187 (R) |
| 0.03 | 4-Cl-C$_6$H$_4$- | H | di-CH$_3$ | H | 3-fluoro-4-carboxyphenyl | CH$_2$ | 188 (R) |
| 0.02 | 4-Cl-C$_6$H$_4$- | H | di-CH$_3$ | H | 3-fluoro-4-(N',N'-dimethylhydrazinocarbonyl)phenyl | CH$_2$ | 189 (R) |

-continued

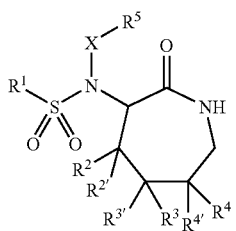

I

| IC$_{50}$ in vitro | R$^1$ | R$^2$ | R$^3$ | R$^4$ | R$^5$ | X | Expl. |
|---|---|---|---|---|---|---|---|
|  | 4-Cl-C$_6$H$_4$ | H | di-CH$_3$ | H | 2-(CH$_2$CH$_2$COOH)-5-F-C$_6$H$_3$ | CH$_2$ | 190 (R) |
| 0.06 | 4-Cl-C$_6$H$_4$ | H | di-CH$_3$ | H | 4-(isoxazol-5-yl)-C$_6$H$_4$ | CH$_2$ | 191 (R) |
| 0.04 | 4-Cl-C$_6$H$_4$ | H | di-CH$_3$ | H | 2-F-4-OMe-C$_6$H$_3$ | CH$_2$ | 192 (R) |
| 0.02 | 4-Cl-C$_6$H$_4$ | H | di-CH$_3$ | H | 2-F-4-CH$_2$OH-C$_6$H$_3$ | CH$_2$ | 193 (R) |
| 0.13 | 4-Cl-C$_6$H$_4$ | H | CF$_3$ | H | 4-(CH$_2$CH$_2$COOH)-C$_6$H$_4$ | CH$_2$ | 194 |
| 0.03 | 4-Cl-C$_6$H$_4$ | H | CF$_3$ | H | 4-COOH-C$_6$H$_4$ | CH$_2$ | 195 |
| 0.19 | 4-Cl-C$_6$H$_4$ | H | CF$_3$ | H | 4-C(O)NHN(CH$_3$)$_2$-C$_6$H$_4$ | CH$_2$ | 196 |
| 0.02 | 4-Cl-C$_6$H$_4$ | H | CF$_3$ | H | 2-F-4-COOMe-C$_6$H$_3$ | CH$_2$ | 197 |

-continued

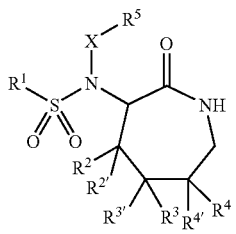

I

| IC$_{50}$ in vitro | R$^1$ | R$^2$ | R$^3$ | R$^4$ | R$^5$ | X | Expl. |
|---|---|---|---|---|---|---|---|
| 0.29 | 4-Cl-C$_6$H$_4$- | H | CF$_3$ | H | 2-F-4-MeO-C$_6$H$_3$- | CH$_2$ | 198 |
| 0.02 | 4-Cl-C$_6$H$_4$- | H | CF$_3$ | H | 3-F-4-(4-COOH)-C$_6$H$_3$- | CH$_2$ | 199 |
|  | 4-Cl-C$_6$H$_4$- | H | CF$_3$ | H | 3-F-4-(CH$_2$OH)-C$_6$H$_3$- | CH$_2$ | 200 |
| 0.02 | 4-Cl-C$_6$H$_4$- | H | H | H | 4-(CH$_2$CH$_2$COOH)-C$_6$H$_4$- | CH$_2$ | 201 (R) |
|  | 4-Cl-C$_6$H$_4$- | H | H | H | 4-(CH$_2$CH$_2$CH$_2$COOMe)-C$_6$H$_4$- | CH$_2$ | 202 (R) |
| 0.19 | 4-Cl-C$_6$H$_4$- | H | H | H | 3-F-4-(COOMe)-C$_6$H$_3$- | CH$_2$ | 203 |
|  | 4-Cl-C$_6$H$_4$- | H | H | H | 4-(CH$_2$CH$_2$CH$_2$COOH)-C$_6$H$_4$- | CH$_2$ | 204 (R) |
|  | 4-Cl-C$_6$H$_4$- | H | H | H | 4-(CH$_2$COOH)-C$_6$H$_4$- | CH$_2$ | 205 (R) |

-continued

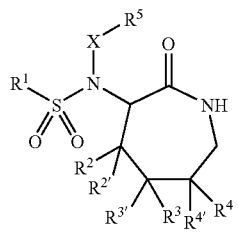

| IC$_{50}$ in vitro | R$^1$ | R$^2$ | R$^3$ | R$^4$ | R$^5$ | X | Expl. |
|---|---|---|---|---|---|---|---|
|  | 4-Cl-C$_6$H$_4$ | H | H | H | 4-(oxazol-5-yl)phenyl | CH$_2$ | 206 (R) |
|  | 4-Cl-C$_6$H$_4$ | H | H | H | 4-(2-acetamidoethyl)phenyl | CH$_2$ | 207 (R) |
| 0.22 | 4-Cl-C$_6$H$_4$ | H | H | H | 4-(isoxazol-5-yl)phenyl | CH$_2$ | 208 (R) |
|  | 4-Cl-C$_6$H$_4$ | H | H | H | 4-(hydroxymethyl)phenyl | CH$_2$ | 209 (R) |
|  | 4-Cl-C$_6$H$_4$ | H | H | H | 2,5-difluoro-4-methoxyphenyl | CH$_2$ | 210 (R) |
| 0.05 | 4-Cl-C$_6$H$_4$ | H | H | H | 2,3-difluoro-4-methoxyphenyl | CH$_2$ | 211 (R) |
|  | 4-Cl-C$_6$H$_4$ | H | H | H | 4-(2-methyl-1-(methoxycarbonyl)propan-2-yl)phenyl | CH$_2$ | 212 (R) |
|  | 4-Cl-C$_6$H$_4$ | H | H | H | 4-(2-methyl-2-(methoxycarbonyl)propyl)phenyl | CH$_2$ | 213 (R) |
|  | 4-Cl-C$_6$H$_4$ | H | H | H | 3-chloro-4-(2-(methoxycarbonyl)ethyl)phenyl | CH$_2$ | 214 (R) |

-continued

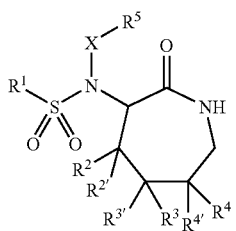

I

| IC$_{50}$ in vitro | R$^1$ | R$^2$ | R$^3$ | R$^4$ | R$^5$ | X | Expl. |
|---|---|---|---|---|---|---|---|
|  | 4-Cl-C$_6$H$_4$ | H | H | H | ethyl 5-benzofuran-2-carboxylate | CH$_2$ | 215 (R) |
|  | 4-Cl-C$_6$H$_4$ | H | H | H | 3-fluoro-4-benzoic acid | CH$_2$ | 216 |
|  | 4-Cl-C$_6$H$_4$ | H | H | H | 3-fluoro-4-benzoic acid | CH$_2$ | 217 (R) |
| 0.21 | 4-Cl-C$_6$H$_4$ | H | H | H | 4-(2-methyl-1-carboxyprop-2-yl)phenyl | CH$_2$ | 218 (R) |
| 0.23 | 4-Cl-C$_6$H$_4$ | H | H | H | 4-(2,2-dimethyl-2-carboxyethyl)phenyl | CH$_2$ | 219 (R) |
|  | 4-Cl-C$_6$H$_4$ | H | H | H | 3-chloro-4-(2-carboxyethyl)phenyl | CH$_2$ | 220 (R) |
|  | 4-Cl-C$_6$H$_4$ | di-CH$_3$ | H | H | 4-(N-cyclopropylcarbamoyl)phenyl | CH$_2$ | 221 rac |
|  | 4-Cl-C$_6$H$_4$ | H | H | H | cyclopropyl | CH$_2$ | 222 rac |

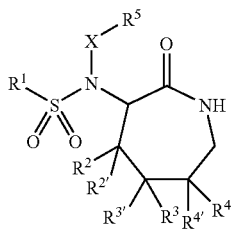

| IC$_{50}$ in vitro | R$^1$ | R$^2$ | R$^3$ | R$^4$ | R$^5$ | X | Expl. |
|---|---|---|---|---|---|---|---|
| | Cl—⟨phenyl⟩— | H | H | H | ⟨cyclobutyl⟩ | CH$_2$ | 223 rac |

The present invention also provides pharmaceutical compositions containing compounds of the invention or pharmaceutically acceptable acid addition salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carrier.

The compounds and compositions of the invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, in the form of injectable solutions.

Compounds of the present invention are γ-secretase inhibitors. Therefore, the invention also provides methods for treating illnesses that are mediated by γ-secretase. Such methods include a method of treating Alzheimer's disease which comprises administering to an individual a therapeutically effective amount of a compound of the invention or a pharmaceutically acceptable salt thereof. Such methods also comprise a method of treating cancer which comprises administering to an individual a therapeutically effective amount of a compound of the invention or a pharmaceutically acceptable salt thereof. In particular, the invention provides a method of treating breast cancer, cervical cancer, and malignancies of the hematopoietic system which comprises administering to an individual a therapeutically effective amount of a compound of the invention.

The dosage at which the compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated

| | | Tablet Formulation (Wet Granulation) mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.

4. Add item 5 and mix for three minutes; compress on a suitable press.

| | | Capsule Formulation mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.
4. Numerous intermediates or reagents such as aldehydes, cyclic ketones, aromatic sulfonyl chlorides, alkyl halides, benzyl halides, benzyl alcohols are used to prepare compounds of formula I. These are typically commercially available, or accessable by literature routes. Representative syntheses are described below.

Preparation of Intermediates

EXAMPLE A

4-Chloromethyl-N-cyclopropyl-benzamide

4-Chloromethyl-benzoyl chloride (2.82 g, 15 mmol) and cyclopropylamine (1.26 ml, 18 mmol) were reacted in $CH_2Cl_2$ (30 ml) and in the presence of Hünig's base (3.1 ml, 18 mmol) for 1 h. A precipitate was formed which was resolubilzed by adding ethyl acetate. The reaction mixture was washed with a 5% $KHSO_4$/10% $K_2SO_4$ solution, NaCl sat. solution and dried ($Na_2SO_4$). The organic phase was filtered and concentrated under reduced pressure to yield a semi-solid which was triturated in hexanes: solid 3.1 g (95%); $^1$H NMR ($CDCl_3$) δ 0.60-0.64 (m, 2H), 0.85-0.90 (m, 2H), 2.89-2.92 (m, 1H), 4.60 (s, 2H), 6.20 (br, 1H), 7.44 (d, 2H), 7.71-7.74 (m, 2H); MS: m/e=210.2 ($MH^+$)

EXAMPLE B (6-Methoxy-pyridin-3-yl)-methanol

To lithium aluminium hydride (0.68 g, 18 mmol) suspended in dry THF (10 ml) was added dropwise a solution of methyl 6-methoxynicotinate (1 g, 6 mmol) in dry THF (5 ml). The reaction mixture was stirred for 2 h at r.t. then cooled (ice-bath) and quenched with water (2 ml) followed by the further addition of 1N NaOH (6 ml) and water (2 ml). The cold-bath was removed and the mixture stirred for 30 min at r.t., filtered and concentrated under reduced pressure. The residue was diluted with water and extracted with ethyl acetate (3×). The combined organic extracts were washed with water, brine, dried ($MgSO_4$), filtered and concentrated under reduced pressure to give a crude oil which was purified over silica gel (ethyl acetate/n-heptane 1:1): colorless oil 0.45 g (51%);
$^1$H NMR ($CDCl_3$) δ 1.69 (t, 1H), 3.94 (s, 3H), 4.62 (d, 2H), 6.75 (d, 1H), 7.62 (dd, 1H), 8.13 (d, 1H); MS: m/e=139.0 ($M^+$)

EXAMPLE C (5-Methoxy-pyridin-2-yl)-methanol 1) 5-Methoxy-2-methyl-pyridine
5-Hydroxy-2-methylpyridine (16.4 g, 150.3 mmol) was added to a suspension of KOH (34.6 g, 616 mmol) in DMSO (250 ml) and stirred for 1 h at r.t. followed by the dropwise addition of methyl iodide (10.3 ml, 165 mmol). The reaction mixture was stirred for a further 16 h, poored onto ice-cold water (500 ml) and extracted with diethyl ether (4×350 ml). The combined ether extracts were washed with water (50 ml), brine (50 ml) and dried ($MgSO_4$). Filtration and concentration of the filtrate under reduced pressure gave a crude oil which was purified over silica gel (ethyl acetate/n-heptane 1:2 to 1:1): light brown oil 10.5 g (54%);
$^1$H NMR ($CDCl_3$) δ 2.49 (s, 3H), 3.82 (s, 3H), 7.04-7.10 (m, 2H), 8.20 (d, 2H); MS: m/e=123.0 (M), 108.0 ($M-CH_3$).

2) 5-Methoxy-2-methyl-pyridine 1-oxide
5-Methoxy-2-methyl-pyridine (10.3 g, 83.6 mmol) was dissolved in $CHCl_3$ (250 ml) and reacted with methyltrioxorhenium (0.2 g, 0.83 mmol) and hydrogen peroxide (30% in water, 14.6 ml). The resultant mixture was stirred overnight at r.t and then cooled (ice-water bath).
Small portions of $MnO_2$ were added until no further $O_2$ gas evolved The reaction mixture was further stirred at r.t. and then diluted with water (140 ml). The organice layer was collected and the aqueous phase was extracted with $CHCl_3$ (2×). The combined $CHCl_3$ fractions were dried ($MgSO_4$), filtered and evaporated. The resultant white solid was stirred for ca. 1 h in n-pentane, filtered and dried under vacuum: solid 9.31 g (76%);
$^1$H NMR ($CDCl_3$) δ 2.45 (s, 3H), 3.81 (s, 3H), 6.83 (dd, 1H), 7.12 (d, 1H), 8.03 (d, 1H); MS: m/e=139.0 (M), 122.0 (M−OH)

3) Acetic acid 5-methoxy-pyridin-2-ylmethyl ester
5-Methoxy-2-methyl-pyridine 1-oxide (9.25 g, 66.5 mmol) was suspended in acetic anhydride (31 ml) under an argon atmosphere. The mixture was heated to ca.115° C. and this temperature was maintained for a further 5 h and the mixture turned black. Ethanol (2.5 ml) was added and the mixture was concentrated under reduced pressure. The residue was taken up in ethyl acetate and washed with 10% $K_2CO_3$ and water. The aqueous phases were back extracted with ethyl acetate and the combined organic phases were dried ($MgSO_4$) filtered and concentrate under reduced pressure. The crude oil was purified using Kugelrohr distillation (90-100° C./0.1 mbar) yielding a colorless oil: 10.7 g (80%);
$^1$H NMR ($CDCl_3$) δ 2.13 (s, 3H), 3.86 (s, 3H), 5.16 (s, 2H), 7.18-7.31 (m, 2H), 8.30 (d, 1H) MS: m/e=181.2 (M), 138.0 (M−$COCH_3$)

4) (5-Methoxy-pyridin-2-yl)-methanol
Acetic acid 5-methoxy-pyridin-2-ylmethyl ester (10.5 g, 58 mmol) was dissolved in HCl (25%, 30 ml) and the resultant reaction mixture was stirred at ca. 105° C. for 80 min under an argon atmosphere. Solid $NaHCO_3$ was added in portions followed by aqueous $K_2CO_3$ solution to achieve an alkaline pH 10. This resultant mixture was extracted with ethyl acetate (4×) and the combined organic extracts were washed with water, brine, dried ($MgSO_4$) filtered and then concentrated under reduced pressure. The crude oil was purified over silica gel (ethyl acetate/n-heptane 1:1 to 2:1): yellow solid 4.8 g (56%);
$^1$H NMR ($CDCl_3$) δ 3.8 (br, 1H), 3.86 (s, 3H), 7.21 (m, 2H), 8.24 (m, 1H); MS: m/e=138.0 (M), 110.0 (M−CO).

EXAMPLE D

5-Hydroxymethyl-pyridine-2-carboxylic acid cyclopropylamide 1) 5-Hydroxymethyl-pyridine-2-carboxylic acid A suspension of $LiBH_4$ (1.53 g, 70 mmol) in THF (30 ml) was slowly added to a solution of pyridine-2,5-dicarboxylic acid 5-methyl ester (2.5 g, 14 mmol) in dry THF (30 ml) at 0° C. and under an argon atmosphere. The reaction mixture was stirred for a further 2 h at r.t., then chilled to 0° C. and treated with 2 N HCl (40 ml). The reaction mixture was filtered, concentrated under reduced pressure and crystallized from MeOH: 340 mg;

$^1H$ NMR ($CDCl_3$) δ 4.73 (s, 1H), 4.91 (s, 2H) 8.36 & 8.58 (dd, 2H), 8.72 (s, 1H) MS: m/e=152.0 ($MH^-$)

2) 5-Hydroxymethyl-pyridine-2-carboxylic acid cyclopropylamide

5-Hydroxymethyl-pyridine-2-carboxylic acid (0.23 g, 1.5 mmol) was dissolved in DMF (3 ml) and activated with TPTU (0.45 g, 1.5 mmol), Hünig's base (0.51 ml, 3.0 mmol) and reacted with cyclopropyl amine (0.12 ml, 1.65 mmol) for 1 h at r.t during which a precipitate was formed. Solvent was removed and the residue dissolved in acetonitrile/water and purified by prep.RP($C_{18}$)HPLC: 60 mg;

$^1H$ NMR ($CDCl_3$) δ 0.65-0.69 (m, 2H), 0.85-0.90 (m, 2H), 2.92-2.97 (m, 1H), 4.81 (d, 2H), 7.84-7.86 (m, 1H), 8.05 (br, 1H), 8.19-8.21 (m, 1H), 8.50 (s, 1H) MS: m/e=193.2 ($MH^+$), 215.3 ($MNa^+$)

EXAMPLE E

[3-Fluoro-4-(2-morpholin-4-yl-ethoxy)-phenyl]-methanol 1) 3-Fluoro-4-(2-morpholin-4-yl-ethoxy)-benzoic acid ethyl ester 3-Fluoro-4-hydroxybenzoic acid ethyl ester (0.20 g, 1.1 mmol) and N-(2-chloroethyl)morpholine (0.22 g, 1.2 mmol) were dissolved in dry DMF (10 ml). Potassium carbonate (1.88 g, 5 mmol) was added and the turbid reaction mixture was stirred overnight at 40° C. under an argon atmosphere. The reaction mixture was concentrated under reduced pressure and ethyl acetate was added to the residue followed by washing with $NaHCO_3$ (½ sat., 3×), water, brine, dried ($MgSO_4$), filtered. The crude oil was purified over silica gel ($CH_2Cl_2$/MeOH 39:1): colorless oil 0.16 g (49%);

$^1H$ NMR ($CDCl_3$) δ 1.38 (t, 3H), 2.59-2.61 (m, 4H), 2.85 (t, 2H), 3.71-3.74 (m, 4H), 4.23 (t, 2H), 4.33 (q, 2H), 6.96-7.0 (m, 1H), 7.73-7.81 (m, 2H); MS: m/e=298.3 ($MH^+$)

2) [3-Fluoro-4-(2-morpholin-4-yl-ethoxy)-phenyl]-methanol

To lithium aluminium hydride (0.03 g, 0.90 mmol) suspended in dry THF (1 ml) and cooled to 0° C. under an argon atmosphere was added a solution of 3-fluoro-4-(2-morpholin-4-yl-ethoxy)-benzoic acid ethyl ester (0.15 g, 0.5 mmol) in dry THF (1 ml). The cold bath was removed and the reaction mixture further stirred for 2 h at r.t. The reaction mixture was cooled (0° C.) and quenched with $NaHCO_3$ (½ sat., 2 ml) and further stirred for 0.5 h at r.t., filtered and concentrated under reduced pressure. The filtrate was dissolved in ethyl acetate and washed with water (2×), brine, dried ($MgSO_4$) filtered and concentrated under reduced pressure: 0.12 g (86%);

$^1H$ NMR ($CDCl_3$) δ 1.75 (br, 1H), 2.60 (t, 4H), 2.83 (t, 2H), 3.73 (t, 4H), 4.17 (t, 2H), 4.62 (s, 2H), 6.93-7.13 (m, 3H); MS: m/e=256.1 ($MH^+$)

EXAMPLE F

4-(2-Hydroxymethyl-phenyl)-butyric acid methyl ester

To an ice cooled solution of methyl 3-butenoate (2.0 g, 20 mmol) in THF (20 ml) 9-borabicyclo(3,3,1)nonane (49 ml, 0.5M in tetrahydrofurane) was added within 1 hour. After additional stirring for 4.5 hours potassium carbonate (7.5 g, 54 mmol), 2-bromobenzyl alcohol (3.4 g, 18.2 mmol), dimethylformamide (60 ml) and palladium (dppf)-dichloride (0.665 g, 0.91 mmol) were added and the mixture was stirred at 60° C. overnight. After cooling the mixture was filtered over Celite and evaporated. The residue was purified by column chromatography (eluent hexane/ethyl acetate: 4:1 gradually to 1:1) to yield 2.46 g (65%) of product.

$^1H$ NMR ($CDCl_3$) δ 1.95 (m, 2H), 2.40 (t, 2H), 2.73 (dd, 2H), 3.66 (s, 3H), 4.72 (d, 2H), 7.20-7.25 (m, 3H), 7.35 (dd, 1H);

EXAMPLE G

4-(3-Hydroxymethyl-phenyl)-butyric acid methyl ester

The title compound was obtained in comparable yield analogous to the procedure described for Example E, using 3-bromobenzyl alcohol instead of using 2-bromobenzyl alcohol.

$^1H$ NMR ($CDCl_3$) δ 1.96 (dt, 2H), 2.33 (t, 2H), 2.66 (t, 2H), 3.66 (s, 3H), 4.67 (d, 2H), 7.10-7.30 (m, 4H).

EXAMPLE 1 rac-5-Chloro-thiophene-2-sulfonic acid (3-fluoro-4-methoxy-benzyl)-(2-oxo-azepan-3-yl)-amide a) rac-3-(3-Fluoro-4-methoxy-benzylamino)-azepan-2-one Rac-amino-azepan-2-one (1.66 g, 128.2 mmol) and 3-fluoro-p-anisaldehyde (2.00 g) were dissolved in dry THF (26 ml). After stirring for 90 min at r.t., acetic acid (1.11 ml, 19.5 mmol) and sodium triacetoxyborohydride (4.58 g, 19.5 mmol) and a further 20 ml dry THF were added and the reaction was stirred overnight at r.t. The reaction mixture was diluted with 2 M $K_2CO_3$, and extracted with ethyl acetate (3×). The combined organic extracts were washed with water, brine, dried ($MgSO_4.2H_2O$) filtered and concentrated under reduced pressure. The resultant solid was redissolved in ethyl acetate and extracted with 5% $KHSO_4$/10% $K_2CO_3$ (3×). The pH of the combined aqueous fraction were adjusted to ca. 8.5-9 using solid $K_2CO_3$ and the aqueous phase was extracted with ethyl acetate (3×). The combined organic fractions were washed as before, dried, filtered and concentrated under reduced pressure: white solid 2.12 g (58%);

$^1H$ NMR ($CDCl_3$) δ 1.40-1.65 (m, 3H), 1.75-1.83 (m, 1H), 1.90-2.05 (m, 2H), 2.35 (br, 1H), 3.19-3.22 (m, 2H), 3.26-3.29 (m, 1H), 3.61 & 3.80 (dd, 1H), 3.87 (s, 3H), 5.95 (br, 1H), 6.87-6.92 (m, 1H), 7.03-7.05 (m, 1H), 7.10-7.13 (m, 1H) MS: m/e=267.5 ($MH^+$)

b) rac-5-Chloro-thiophene-2-sulfonic acid (3-fluoro-4-methoxy-benzyl)-(2-oxo-azepan-3-yl)-amide rac-3-(3-Fluoro-4-methoxy-benzylamino)-azepan-2-one (213 mg, 0.80 mmol) was dissolved in $CH_2Cl_2$ (7.7 ml) and treated with DMAP (30 mg, 0.24 mmol), Hünig's base (0.30 ml, 1.76 mmol) and ⅛ of the cooled (0° C.) reaction mixture was reacted with 5-chloro-thiophene-2-sulfonyl chloride (48 mg, 0.22 mmol) and shaken overnight in a parallel reaction block. Solvent was removed under reduced pressure and the residue dissolved in aqueous acetonitrile solution and purified using high throughput preparative RP($C_{18}$) chromatography: lyophilisate 13 mg;
MS: m/e=447.2 ($MH^+$), 464.2 ($MNH_4^+$).

EXAMPLE 2

4-{[(4-Chloro-benzenesulfonyl)-((R)-2-oxo-azepan-3-yl)-amino]-methyl}-benzamide a) 3R-Amino-azepan-2-one D-Lysine hydrochloride (48 g, 0.26 mol) and hexamethyldisilazane (424.4 g, 2.6 mol) were suspended in toluene (1.1 liter) and refluxed for 1 week under an argon atmosphere, using a water-trap condenser. The reaction mixture was cooled to r.t. and slowly added to ice-cold MeOH (2.24 liter). The resultant clear solution was stirred for 30 min and concentrated under reduced pressure. The white, waxy solid was stirred in ethyl acetate, filtered and the filtrated concentrated under reduced pressure: white solid 5.4 g, (15%);
$^1$H NMR ($CDCl_3$) δ 1.35-2.05 (m, 8H), 3.2-3.26 (m, 2H), 3.53 (dd, 1H), 6.10 (br, 1H) MS: m/e=129.2 ($MH^+$)

b) 4-Chloro-N-((R)-2-oxo-azepan-3-yl)-benzenesulfonamide

3R-Amino-azepan-2-one (3.02 g, 23.6 mmol) was dissolved in $CH_2Cl_2$ (50 ml), treated with Hünig's base (6.16 ml, 35.4 mmol) and cooled (0° C.) under an argon atmosphere. A solution of 4-chlorobenzenesulfonyl chloride (5.5 g, 26 mmol) in $CH_2Cl_2$ (15 ml) was added dropwise. The cold-bath was removed and the reaction mixture further stirred at r.t. for 2.5 h. The reaction mixture was diluted with $CH_2Cl_2$ and washed with $NaHCO_3$ (½ sat., 3×), 5% $KHSO_4$/ 10% $K_2CO_3$ (3×), brine, dried ($MgSO_4$) filtered and concentrated under reduced pressure. The solid was recrystallized from ethyl acetate/n-heptane: 6.1 g (84%); $^1$H NMR ($CDCl_3$) δ 1.33-1.40 (m, 1H), 1.57-1.69 (m, 2H), 1.78-1.83 (m, 1H), 1.84-2.15 (m, 2H), 3.04-3.21 (m, 2H), 3.81-3.85 (m, 1H), 6.02 (br, 1H) 6.21 (d, 1H), 7.45-7.48 (m, 2H), 7.78-7.80 (m, 2H) MS: m/e=301.3 ($MH^-$)

c) 4-{[(4-Chloro-benzenesulfonyl)-((R)-2-oxo-azepan-3-yl)-amino]-methyl}-benzamide 4-Chloro-N-((R)-2-oxo-azepan-3-yl)-benzenesulfonamide (0.18 g, 0.60 mmol), 4-bromo-methyl-benzamide (0.19 g, 0.90 mmol), $K_2CO_3$ (0.83 g, 6 mmol), KI (0.02 g, 0,12 mmol) were added to dry DMF (15 ml) and the resultant reaction mixture was shaken overnight at 60° C. under an argon atmosphere. The solvent was removed under reduced pressure and the residue dissolved in acetonitrile and purified using preparative RP($C_{18}$) chromatography: lyophilisate 52 mg; MS: m/e=436.4 ($MH^+$)

EXAMPLE 3

4-Chloro-N-(6-methoxy-pyridin-3-ylmethyl)-N-((R)-2-oxo-azepan-3-yl)-benzenesulfonamide 4-Chloro-N-((R)-2-oxo-azepan-3-yl)-benzenesulfonamide (0.04 g, 0.12 mmol), (5-Methoxy-pyridin-2-yl)-methanol (0.04 g, 030 mmol), triphenyl phosphine (0.08 g, 0.30 mmol) were dissolved in dry $CH_2Cl_2$ (6 ml) under an argon atmosphere followed by the dropwise addition of diisopropyl azodicarboxylate (60 mg, 0.30 ml) in dry $CH_2Cl_2$ (2 ml). The reaction mixture was further stirred overnight at r.t. and then concentrated under reduced pressure. The crude yellow oil was purified over silica gel (ethyl acetate/n-heptane 3:2): colorless gum 0.23 g (43%); MS: m/e=424.0 ($MH^+$), 446.0 ($MNa^+$).

EXAMPLE 4

4-{[(4-Chloro-benzenesulfonyl)-(5-isopropyl-2-oxo-azepan-3-yl)-amino]-methyl}-benzamide a) 5-Isopropyl-azepan-2-one To a solution of hydroxylamine-O-sulfonic acid (60.5 g, 535 mmol) in formic acid (320 ml) was added dropwise a solution of 4-isopropyl cyclohexanone (50.0 g, 357 mmol) in formic acid (110 ml) at r.t. under an argon atmosphere. The reaction mixture was refluxed for 3 h, cooled to r.t. and slowly treated with ice-water (550 ml). 10 N NaOH (1.1 liter) was added to adjust the pH to 8 and the resultant mixture was extracted with $CHCl_3$ (4×). The combined organic extracts were washed with water, brine, dried ($MgSO_4$), filtered and concentrated under reduced pressure. The light-brown solid was crystallized from n-heptane: 42.4 g (75%);
$^1$H NMR ($CDCl_3$) δ 0.87 (d, 6H), 1.35-1.39 (m, 3H), 1.60 1.68 (m, 1H), 1.76-1.80 (m, 2H), 2.43-2.49 (m, 2H), 3.20-3.24 (m, 2H), 6.25 (br, 1H) MS: m/e=155.1 (M)

b) 3,3-Dichloro-5-isopropyl-azepan-2-one

5-Isopropyl-azepan-2-one (39.5 g, 254.4 mmol) was dissolved in xylenes (1.1 liter) and phosphorus pentachloride (159.0 g, 763.3 mmol) was added and the reaction mixture slowly warmed to 90° C. $HCl_{(g)}$ accompanied the slow dissolution of phosphorus pentachloride and after 30 min a clear yellow solution resulted. After a further 90 min at 90° C. the reaction mixture was allowed to cool (ice-water bath) and water (500 ml) was added dropwise. The emulsion was stirred for a further 90 min at r.t and the aqueous layer was washed with $CHCl_3$ (3×). The xylene fraction was concentrated under reduced pressure and the residue was dissolved in $CHCl_3$. The combined organic fractions were washed with water (3×), brine and dried ($MgSO_4$) filtered and evaporated under reduced pressure. The crude brown oil was purified over silica gel (ethyl acetate/n-heptane 1:2): white solid 39.8 g (58%);
$^1$H NMR ($CDCl_3$) δ 0.93 (d, 6H), 1.32-1.36 (m, 1H), 1.68-1.72 (m, 1H), 2.00-2.01 (m, 1H), 2.27-2.34 (m, 1H), 2.66-2.70 (m, 1H), 3.23-3.27 (m, 1H), 3.51-3.55 (m, 1H), 6.30 (br, 1H) MS: m/e=224.1 ($MH^+$)

c) 3-Chloro-5-isopropyl-azepan-2-one 3,3-Dichloro-5-isopropyl-azepan-2-one (5.00 g, 22.3 mmol) was dissolved in acetic acid (125 ml) and sodium acetate (anhydrous, 2.38 g, 29.0 mmol), 10% Pd-c catalyst (0.22 g) were added. The degassed mixture was hydrogenated at r.t. and atmospheric pressure for 90 min. The reaction mixture was filtered and concentrated under reduced pressure. The residue was purified over silica gel (ethyl acetate/n-heptane 1:1): 3.49 g (74%) $^1$H NMR ($CDCl_3$) δ 0.88-0.90 (m, 6H), 1.26-1.29 (m, 1H), 1.63-1.67 (m, 2H), 1.76-1.94 (m, 2H), 2.16-2.21 (m, 1H), 3.19-3.23 (m, 1H), 3.30-3.36 (m, 1H), 4.64 & 4.67 (dd, 1H), 6.45 (br, 1H) MS: m/e=190.3 ($MH^+$), 207.2 ($MNH_4^+$)

d) 3-Azido-5-isopropyl-azepan-2-one

3-Chloro-5-isopropyl-azepan-2-one (3.4 g, 18 mmol) and sodium azide (3.51 g, 53.9 mmol) were reacted in dry dimethyl sulfoxide (50 ml) overnight at 80° C. under an argon atmosphere. The reaction mixture was allowed to cool to r.t. diluted with water (200 ml) and extrated with $CH_2Cl_2$ (4×). The combined organic fractions were washed with water (3×), brine and dried (MgSO$_4$) filtered and evaporated under reduced pressure. The crude yellow oil was purified over silica gel (ethyl acetate/n-heptane 1:2): yellow oil 2.6 g (70%); MS: m/e=197.4 (MH$^+$)

e) 4-Chloro-N-(5-isopropyl-2-oxo-azepan-3-yl)-benzenesulfonamide

3-Azido-5-isopropyl-azepan-2-one (70 mg, 0.36 mmol) was dissolved in ethanol/water (2:1 v/v) and hydrogenated over 10% Pd-c (5 mg) for 2 h. The reaction mixture was filtered and concentrated under reduced pressure. The residue was taken up in dry CH$_2$Cl$_2$ (5 ml) and Hünig's base (0.09 ml, 0.54 mmol) was added and this mixture was cooled (ice-bath) followed by the dropwise addition of 4-chlorobenzylsulfonyl chloride (90.3 mg, 0.43 mmol) in CH$_2$Cl$_2$ (0.5 ml). The reaction mixture was stirred at r.t. for 1 h and then diluted with CH$_2$Cl$_2$ and washed with NaHCO$_3$ (1/2 sat., 3×), 5% KHSO$_4$/10% K$_2$SO$_4$ (3×), water, brine, dried (MgSO$_4$) and filtered. The filtrate was concentrated under reduced pressure and the crude product was purified over silica gel (ethyl acetate/n-heptane 1:2 to 1:1): white solid 0.08 g (75%); MS: m/e=343.0 (MH$^-$)

f) 4-{[(4-Chloro-benzenesulfonyl)-(5-isopropyl-2-oxo-azepan-3-yl)-amino]-methyl}-benzamide 4-Chloro-N-(5-isopropyl-2-oxo-azepan-3-yl)-benzenesulfonamide (0.06 g, 0.17 mmol), 4-bromo-methyl-benzamide (0.06 g, 0.25 mmol), K$_2$CO$_3$ (0.24 g, 1.7 mmol), KI (0.01 g, 0.06 mmol) were added to dry DMF (5 ml) and the resultant reaction mixture was shaken overnight at 65° C. under an argon atmosphere. The solvent was removed under reduced pressure and the residue taken up in ethyl acetate and washed with 5% KHSO$_4$/10% K$_2$SO$_4$ (2×), water, brine, dried (MgSO$_4$), filtered, concentrated under reduced pressure and purified using preparative RP(C$_{18}$) chromatography: lyophilisate 23 mg; MS: m/e=478.3 (MH$^+$), 495.4 (MNH$_4^+$)

EXAMPLE 5 rac-4-Chloro-N-(2-oxo-azepan-3-yl)-N-pyridin-3-ylmethyl-benzenesulfonamide

The title compound, MS: m/e=393.9 (MH$^+$), was obtained in comparable yield analogous to the procedure described for Example 3 using 3-(hydroxymethyl)pyridine as the alcohol.

EXAMPLE 6 rac-4-Chloro-N-(4-fluoro-benzyl)-N-(2-oxo-azepan-3-yl)-benzenesulfonamide

The title compound, MS: m/e=411.0 (MH$^+$), 433.1 (MNa$^+$), was obtained in comparable yield analogous to the procedure described for Example 3, using 4-fluorobenzylalcohol as the alcohol.

EXAMPLE 7 rac-4-Chloro-N-(4-chloro-benzyl)-N-(2-oxo-azepan-3-yl)-benzenesulfonamide

The title compound, MS: m/e=427.0 (MH$^+$), 448.8 (MNa$^+$), was obtained in comparable yield analogous to the procedure described for Example 3, using 4-chlorobenzylalcohol as the alcohol.

EXAMPLE 8 rac-4-Chloro-N-(3-fluoro-4-methoxy-benzyl)-N-(2-oxo-azepan-3-yl)-benzenesulfonamide The title compound, MS: m/e=441.0 (MH$^+$), 463.0 (MNa$^+$), was obtained in comparable yield analogous to the procedure described for Example 3, using (3-Fluoro-4-methoxy-phenyl)-methanol as the alcohol.

EXAMPLE 9 rac-4-Chloro-N-(3,4-difluoro-benzyl)-N-(2-oxo-azepan-3-yl)-benzenesulfonamide

The title compound, MS: m/e=429.0 (MH$^+$), 450.9 (MNa$^+$), was obtained in comparable yield analogous to the procedure described for Example 3, using 3,4-difluorobenzyl alcohol as the alcohol.

EXAMPLE 10 rac-4-Chloro-N-(4-methoxy-benzyl)-N-(2-oxo-azepan-3-yl)-benzenesulfonamide

The title compound, MS: m/e=422.9 (MH$^+$), 445.0 (MNa$^+$), was obtained in comparable yield analogous to the procedure described for Example 3, using 4-methoxybenzyl alcohol as the alcohol.

EXAMPLE 11

4-Chloro-N-(2,6-difluoro-4-methoxy-benzyl)-N-((R)-2-oxo-azepan-3-yl)-benzenesulfonamide The title compound, MS: m/e=459.3 (MH$^+$), 476.3 (MNH$_4^+$), was obtained in comparable yield analogous to the procedure described for Example 3, using (2,6-difluoro-4-methoxy-phenyl)-methanol as the alcohol.

EXAMPLE 12 rac-4-Chloro-N-(3,4-dichloro-benzyl)-N-(2-oxo-azepan-3-yl)-benzenesulfonamide

The title compound, MS: m/e=460.8 (MH$^+$), was obtained in comparable yield analogous to the procedure described for Example 3, using 3,4-dichlorobenzyl alcohol as the alcohol.

EXAMPLE 13 rac-Dimethyl-carbamic acid 6-{[(4-chloro-benzenesulfonyl)-(2-oxo-azepan-3-yl)-amino]-methyl}-pyridin-3-yl ester The title compound, MS: m/e=480.9 (MH$^+$), was obtained in comparable yield analogous to the procedure described for Example 3, using dimethyl-carbamic acid 6-hydroxymethyl-pyridin-3-yl ester as the alcohol.

EXAMPLE 14 rac-4-Chloro-N-(6-chloro-pyridin-3-ylmethyl)-N-(2-oxo-azepan-3-yl)-benzenesulfonamide The title compound, MS: m/e=428.0 (MH$^+$), 449.8 (MNa$^+$), was obtained in comparable yield analogous to the procedure described for Example 3, using (6-chloro-pyridin-3-yl)-methanol as the alcohol.

EXAMPLE 15 rac-4-Chloro-N-(6-fluoro-pyridin-3-ylmethyl)-N-(2-oxo-azepan-3-yl)-benzenesulfonamide The title compound, MS: m/e=412.0 (MH$^+$), 434 (MNa$^+$), was obtained in comparable yield analogous to the procedure described for Example 3, using (6-fluoro-pyridin-3-yl)-methanol as the alcohol.

EXAMPLE 16 rac-4-Chloro-N-(5-chloro-pyridin-2-ylmethyl)-N-(2-oxo-azepan-3-yl)-benzenesulfonamide The title compound, MS: m/e=428.0 (MH$^+$), 449.9 (MNa$^+$), was obtained in comparable yield analogous to the procedure described for Example 3, using (5-chloro-pyridin-2-yl)-methanol as the alcohol.

EXAMPLE 17 rac-Acetic acid 4-{[(4-chloro-benzenesulfonyl)-(2-oxo-azepan-3-yl)-amino]-methyl}-phenyl ester The title compound, MS: m/e=450.8 (MH$^+$), 473.0 (MNa$^+$), was obtained in comparable yield analogous to the procedure described for Example 3, using acetic acid 4-hydroxymethyl-phenyl ester as the alcohol.

EXAMPLE 18 rac-4-Chloro-N-(2-oxo-azepan-3-yl)-N-(4-prop-2-ynyloxy-benzyl)-benzenesulfonamide The title compound, MS: m/e=447.0 (MH$^+$), 469.0 (MNa$^+$), was obtained in comparable yield analogous to the procedure described for Example 3, using (4-prop-2-ynyloxy-phenyl)-methanol as the alcohol.

EXAMPLE 19 rac-4-Chloro-N-(3-fluoro-4-methyl-benzyl)-N-(2-oxo-azepan-3-yl)-benzenesulfonamide The title compound, MS: m/e=424.9 (MH$^+$), 447.0 (MNa$^+$), was obtained in comparable yield analogous to the procedure described for Example 3, using (3-fluoro-4-methyl-phenyl)-methanol as the alcohol.

EXAMPLE 20 rac-4-Chloro-N-(4-chloro-3-fluoro-benzyl)-N-(2-oxo-azepan-3-yl)-benzenesulfonamide The title compound, MS: m/e=MS: m/e=445.0 (MH$^+$), 466.9 (MNa$^+$), was obtained in comparable yield analogous to the procedure described for Example 3, using 4-chloro-3-fluorobenzylalcohol as the alcohol.

EXAMPLE 21 rac-4-Chloro-N-(4-difluoromethoxy-benzyl)-N-(2-oxo-azepan-3-yl)-benzenesulfonamide The title compound, MS: m/e=459.0 (MH$^+$), 481.1 (MNa$^+$), was obtained in comparable yield analogous to the procedure described for Example 2c, using 4-(difluoromethoxy)benzyl bromide as the benzylating reagent.

EXAMPLE 22 rac-4-Chloro-N-[3-fluoro-4-(2-morpholin-4-yl-ethoxy)-benzyl]-N-(2-oxo-azepan-3-yl)-benzenesulfonamide The title compound, MS: m/e=540.3 (MH$^+$), was obtained in comparable yield analogous to the procedure described for Example 3, using [3-fluoro-4-(2-morpholin-4-yl-ethoxy)-phenyl]-methanol as the alcohol.

EXAMPLE 23 rac-4-{[(4-Chloro-benzenesulfonyl)-(2-oxo-azepan-3-yl)-amino]-methyl}-benzamide

The title compound, MS: m/e=436.3 (MH$^+$), 458.0 (MNa$^+$), was obtained analogous to the procedure described for Example 2c, using 4-bromomethyl-benzamide as the benzylating reagent.

EXAMPLE 24 rac-4-Chloro-N-(4-chloro-3-methoxy-benzyl)-N-(2-oxo-azepan-3-yl)-benzenesulfonamide The title compound, MS: m/e=457.1 (MH$^+$), 478.9 (MNa$^+$), was obtained analogous to the procedure described for Example 2c, using 4-bromomethyl-1-chloro-2-methoxy-benzene as the benzylating reagent.

EXAMPLE 25

4-Chloro-N-(3-fluoro-4-methoxy-benzyl)-N-((R)-2-oxo-azepan-3-yl)-benzenesulfonamide The title compound, MS: m/e=441.3 (MH$^+$), 463.0 (MNa$^+$), was obtained in comparable yield analogous to the procedure described for Example 2c, using 3-fluoro-4-methoxybenzyl bromide as the benzylating reagent.

EXAMPLE 26

4-Chloro-N-(3,4-dichloro-benzyl)-N-((R)-2-oxo-azepan-3-yl)-benzenesulfonamide

The title compound, MS: m/e=461.0 (MH$^+$), 484.9 (MNa$^+$), was obtained in comparable yield analogous to the procedure described for Example 3, using (3,4-dichloro-phenyl)-methanol as the alcohol.

EXAMPLE 27

Acetic acid 4-{[(4-chloro-benzenesulfonyl)-((R)-2-oxo-azepan-3-yl)-amino]-methyl}-phenyl ester The title compound, MS: m/e=451.0 (MH$^+$), 473.1 (MNa$^+$), was obtained in comparable yield analogous to the procedure described for Example 3, using acetic acid 4-hydroxymethyl-phenyl ester as the alcohol.

EXAMPLE 28 rac-4-Bromo-N-(3-fluoro-4-methoxy-benzyl)-N-(2-oxo-azepan-3-yl)-benzenesulfonamide The title compound, MS: m/e=486.8 (MH$^+$), 503.7 (MNH$_4^+$), was obtained in comparable yield according to the procedure described for Example 2c, using 3-fluoro-4-methoxybenzyl bromide as the benzylating reagent and the analogous 4-bromophenyl sulfonamide.

EXAMPLE 29 rac-4-Chloro-N-(3-methoxy-benzyl)-N-(2-oxo-azepan-3-yl)-benzenesulfonamide

The title compound, MS: m/e=423.2 (MH$^+$), was obtained in comparable yield analogous to the procedure described for Example 3, using 3-methoxybenzyl alcohol as the alcohol.

EXAMPLE 30 rac-4-Chloro-N-(5,6-dichloro-pyridin-3-ylmethyl)-N-(2-oxo-azepan-3-yl)-benzenesulfonamide The title compound, MS: m/e=462.2 (MH$^+$), 479.2 (MNH$_4^+$), was obtained in comparable yield analogous to the procedure described for Example 3, using 5,6-dichloro-pyridin-3-ylmethanol as the alcohol.

EXAMPLE 31 rac-4-Chloro-N-(4-ethoxy-benzyl)-N-(2-oxo-azepan-3-yl)-benzenesulfonamide

The title compound, MS: m/e=437.3 (MH$^+$), was obtained in comparable yield analogous to the procedure described for Example 3, using 4-ethoxybenzyl alcohol as the alcohol.

EXAMPLE 32 rac-4-Chloro-N-(2,5-difluoro-benzyl)-N-(2-oxo-azepan-3-yl)-benzenesulfonamide

The title compound, MS: m/e=429.4 (MH$^+$), 446.2 (MNH$_4^+$), was obtained in comparable yield according to the procedure described for Example 2c, using 2,5-difluorobenzyl bromide as the benzylating reagent.

EXAMPLE 33 rac-4-Chloro-N-(2-oxo-azepan-3-yl)-N-(2,4,5-trifluoro-benzyl)-benzenesulfonamide The title compound, MS: m/e=447.3 (MH$^+$), 464.2 (MNH$_4^+$), was obtained in comparable yield according to the procedure described for Example 2c, using 2,4,5-trifluorobenzyl bromide as the benzylating reagent.

EXAMPLE 34

4-{[(4-Chloro-benzenesulfonyl)-((R)-2-oxo-azepan-3-yl)-amino]-methyl}-3-fluoro-benzoic acid methyl ester The title compound, MS: m/e=469.2 (MH$^+$), 486.4 (MNH$_4^+$), was obtained in comparable yield according to the procedure described for Example 2c, using 4-bromomethyl-3-fluoro-benzoic acid methyl ester as the benzylating reagent.

EXAMPLE 35

4-{[(4-Chloro-benzenesulfonyl)-((R)-2-oxo-azepan-3-yl)-amino]-methyl}-benzoic acid ethyl ester The title compound, MS: m/e=465.3 (MH$^+$), was obtained in comparable yield according to the procedure described for Example 2c, using 4-bromomethyl-benzoic acid ethyl ester as the benzylating reagent.

EXAMPLE 36

(3-{[(4-Chloro-benzenesulfonyl)-((R)-2-oxo-azepan-3-yl)-amino]-methyl}-phenyl)-acetic acid methyl ester The title compound, MS: m/e=465.0 (MH$^+$), was obtained in comparable yield according to the procedure described for Example 2c, using (3-chloromethyl-phenyl)-acetic acid methyl ester as the benzylating reagent.
MS: m/e=465.0 (MH$^+$).

EXAMPLE 37

4-{[(4-Chloro-benzenesulfonyl)-((R,S)-2-oxo-azepan-3-yl)-amino]-methyl}-benzoic acid 4-{[(4-Chloro-benzenesulfonyl)-((R)-2-oxo-azepan-3-yl)-amino]-methyl}-benzoic acid ethyl ester (0.08 g, 0.17 mmol) was saponified with 1 N NaOH (0.25 ml) in ethanol (2 ml) for 48 h. The reaction mixture was diluted with acetic acid (0.7 ml) concentrated under reduced pressure and purified directly using preparative RP(C$_{18}$) chromatography: lyophilisate 27 mg; MS: m/e=435.0 (MH$^+$).

EXAMPLE 38

3-{[(4-Chloro-benzenesulfonyl)-((R)-2-oxo-azepan-3-yl)-amino]-methyl}-benzoic acid prop-2-ynyl ester The title compound, MS: m/e=474.9 (MH$^+$), 492.0 (MNH$_4^+$), was obtained in comparable yield according to the procedure described for Example 2c, using 3-chloromethyl-benzoic acid prop-2-ynyl ester as the benzylating reagent.

EXAMPLE 39

3-(4-{[(4-Chloro-benzenesulfonyl)-((R)-2-oxo-azepan-3-yl)-amino]-methyl}-phenyl)-propionic acid methyl ester The title compound, MS: m/e=478.9 (MH$^+$), was obtained in comparable yield according to the procedure described for Example 2c, using 3-(4-chloromethyl-phenyl)-propionic acid methyl ester as the benzylating reagent.

EXAMPLE 40

4-Chloro-N-(6-chloro-pyridin-3-ylmethyl)-N-((R)-2-oxo-azepan-3-yl)-benzenesulfonamide The title compound, MS: m/e=427.9 (MH$^+$), was obtained in comparable yield analogous to the procedure described for Example 3, using (6-chloro-pyridin-3-yl)-methanol as the alcohol.

EXAMPLE 41

4-{1-[(4-Chloro-benzenesulfonyl)-((R)-2-oxo-azepan-3-yl)-amino]-ethyl}-benzoic acid methyl ester The title compound, MS: m/e=465.0 (MH$^+$), was obtained in comparable yield analogous to the procedure described for Example 3, using methyl 4-(1-hydroxyethyl) benzoate as the alcohol.

EXAMPLE 42 rac-4-Chloro-N-(5-isopropyl-2-oxo-azepan-3-yl)-N-(6-methoxy-pyridin-3-ylmethyl)-benzenesulfonamide The title compound, MS: m/e=466.3 (MH$^+$), was obtained in comparable yield analogous to the procedure described for Example 3, using 6-methoxy-pyridin-3-yl)-methanol and 4-chloro-N-(5-isopropyl-2-oxo-azepan-3-yl)-benzenesulfonamide from Example 4e.

EXAMPLE 43 rac-4-{[(4-Chloro-benzenesulfonyl)-(5-isopropyl-2-oxo-azepan-3-yl)-amino]-methyl}-N-cyclopropyl-benzamide The title compound, MS: m/e=518.3 (MH$^+$), 535.4 (MNH$_4^+$), was obtained in comparable yield analogous to the procedure described for Example 2c, using 4-chloromethyl-N-cyclopropyl-benzamide and 4-chloro-N-(5-isopropyl-2-oxo-azepan-3-yl)-benzenesulfonamide from Example 4e.

EXAMPLE 44 rac-4-Chloro-N-(5-isopropyl-2-oxo-azepan-3-yl)-N-(6-methyl-pyridin-3-ylmethyl)-benzenesulfonamide The title compound, MS: m/e=450.1 (MH$^+$), was obtained in comparable yield analogous to the procedure described for Example 2c, using 5-chloromethyl-2-methyl-pyridine and 4-chloro-N-(5-isopropyl-2-oxo-azepan-3-yl)-benzenesulfonamide from Example 4e.

EXAMPLE 45 rac-4-Chloro-N-(4-difluoromethoxy-benzyl)-N-(5-isopropyl-2-oxo-azepan-3-yl)-benzenesulfonamide The title compound, MS: m/e=501.3 (MH$^+$), 518.3 (MNH$_4^+$), was obtained in comparable yield analogous to the procedure described for Example 2c, using 4-(difluoromethoxy)benzyl bromide and 4-chloro-N-(5-isopropyl-2-oxo-azepan-3-yl)-benzenesulfonamide from Example 4e.

EXAMPLE 46 rac-4-Chloro-N-(2-methyl-benzyl)-N-(2-oxo-azepan-3-yl)-benzenesulfonamide

The title compound, MS: m/e=407.3 (MH$^+$), 429.4 (MNa$^+$), was obtained in comparable yield according to the procedure described for Example 2c, using 1-bromomethyl-2-methyl-benzene as the benzylating reagent.

EXAMPLE 47 rac-4-Chloro-N-(3-methyl-benzyl)-N-(2-oxo-azepan-3-yl)-benzenesulfonamide

The title compound, MS: m/e=407.3 (MH$^+$), 429.4 (MNa$^+$), was obtained in comparable yield according to the procedure described for Example 2c, using 1-bromomethyl-3-methyl-benzene as the benzylating reagent.

EXAMPLE 48 rac-4-Chloro-N-(4-methyl-benzyl)-N-(2-oxo-azepan-3-yl)-benzenesulfonamide

The title compound, MS: m/e=407.4 (MH$^+$), 429.4 (MNa$^+$), was obtained in comparable yield according to the procedure described for Example 2c, using 1-bromomethyl-4-methyl-benzene as the benzylating reagent.

EXAMPLE 49 rac-4-Chloro-N-(2-chloro-benzyl)-N-(2-oxo-azepan-3-yl)-benzenesulfonamide

The title compound, MS: m/e=427.3 (MH$^+$), 449.2 (MNa$^+$), was obtained in comparable yield according to the procedure described for Example 2c, using 1-bromomethyl-2-chloro-benzene as the benzylating reagent.

EXAMPLE 50 rac-4-Chloro-N-(3-chloro-benzyl)-N-(2-oxo-azepan-3-yl)-benzenesulfonamide

The title compound, MS: m/e=427.3 (MH$^+$), was obtained in comparable yield according to the procedure described for Example 2c, using 1-bromomethyl-3-chloro-benzene as the benzylating reagent.

EXAMPLE 51 rac-4-Chloro-N-(2-fluoro-benzyl)-N-(2-oxo-azepan-3-yl)-benzenesulfonamide

The title compound, MS: m/e=411.3 (MH$^+$), 433.3 (MNa$^+$), was obtained in comparable yield according to the procedure described for Example 2c, using 1-bromomethyl-2-fluoro-benzene as the benzylating reagent.

EXAMPLE 52 rac-4-Chloro-N-(3-fluoro-benzyl)-N-(2-oxo-azepan-3-yl)-benzenesulfonamide

The title compound, MS: m/e=411.3 (MH$^+$), 433.3 (MNa$^+$), was obtained in comparable yield according to the procedure described for Example 2c, using 1-bromomethyl-3-fluoro-benzene as the benzylating reagent.

EXAMPLE 53 rac-4-Chloro-N-(2-oxo-azepan-3-yl)-N-(3-trifluoromethoxy-benzyl)-benzenesulfonamide The title compound, MS: m/e=477.2 (MH$^+$), 499.2 (MNa$^+$), was obtained in comparable yield according to the procedure described for Example 2c, using 1-bromomethyl-3-trifluoromethoxy-benzene as the benzylating reagent.

EXAMPLE 54 rac-4-Chloro-N-(2-oxo-azepan-3-yl)-N-(4-trifluoromethoxy-benzyl)-benzenesulfonamide The title compound, MS: m/e=477.2 (MH$^+$), 499.2 (MNa$^+$), was obtained in comparable yield according to the procedure described for Example 2c, using 1-bromomethyl-4-trifluoromethoxy-benzene as the benzylating reagent.

EXAMPLE 55

4-Chloro-N-(4-cyano-2-fluoro-benzyl)-N-((R)-2-oxo-azepan-3-yl)-benzenesulfonamide The title compound, MS: m/e=436.1 (MH$^+$), 453.0 (MNH$_4^+$) was obtained in comparable yield analogous to the procedure described for Example 2c, using 4-bromomethyl-3-fluoro-benzonitrile as the benzylating reagent.

EXAMPLE 56

4-Chloro-N-[2-fluoro-4-(2H-[1,2,4]triazol-3-yl)-benzyl]-N-((R)-2-oxo-azepan-3-yl)-benzenesulfonamide 4-{[(4-Chloro-benzenesulfonyl)-((R)-2-oxo-azepan-3-yl)-amino]-methyl}-3-fluoro-benzimidic acid ethyl ester hydrochloride salt Dry HCl gas was slowly bubbled through a solution of 4-chloro-N-(4-cyano-2-fluoro-benzyl)-N-((R)-2-oxo-azepan-3-yl)-benzenesulfonamide (0.09 g, 0.20 mmol) in dry ethanol (3 ml) for 30 min at 0° C. The reaction mixture wa allowed to stir for a further 20 h at r.t. and then concentrated under reduced pressure. Trituration of the residue in diethyl ether yielded the HCl salt: 0.09 g; MS: m/e=482.2 (MH$^+$).

4-Chloro-N-[2-fluoro-4-(2H-[1,2,4]triazol-3-yl)-benzyl]-N-((R)-2-oxo-azepan-3-yl)-benzenesulfonamide The HCl salt (0.08 g, 0.15 mmol) and formyl hydrazine (0.01 g, 0.17 mmol) were dissolved in pyridine (1.5 ml) and further stirred for 4 h to give the N-formyl amidrazone intermediate. Solvent was removed under reduced pressure was refluxed in xylenes (5 ml) for 30 min. Solvent was removed under reduced pressure and the residue was purified using preparative RP(C$_{18}$) chromatography: lyophilisate 0.016 mg; MS: m/e=477.9 (MH$^+$), 495.1 (MNH$_4^+$).

EXAMPLE 57 rac-4-{[(4-Chloro-benzenesulfonyl)-(2-oxo-azepan-3-yl)-amino]-methyl}-benzoic acid methyl ester The title compound, MS: m/e=451.3 (MH$^+$), was obtained in comparable yield according to the procedure described for Example 2c, using 4-bromomethyl-benzoic acid methyl ester.

EXAMPLE 58 rac-N-(4-{[(4-Chloro-benzenesulfonyl)-(2-oxo-azepan-3-yl)-amino]-methyl}-phenyl)-acetamide The title compound, MS: m/e=450.4 (MH$^+$), 472.2 (MNa$^+$), was obtained in comparable yield according to the procedure described for Example 2c, using N-(4-chloromethyl-phenyl)-acetamide.

EXAMPLE 59 rac-4-Chloro-N-(4-methanesulfonyl-benzyl)-N-(2-oxo-azepan-3-yl)-benzenesulfonamide The title compound, MS: m/e=471.3 (MH$^+$), 493.3 (MNa$^+$), was obtained in comparable yield according to the procedure described for Example 2c, using 1-bromomethyl-4-methanesulfonyl-benzene as the benzylating reagent.

EXAMPLE 60 rac-4-{[(4-Chloro-benzenesulfonyl)-(2-oxo-azepan-3-yl)-amino]-methyl}-N,N-diethyl-benzamide The title compound, MS: m/e=492.3 (MH$^+$), 509.3 (MNH$_4^+$), was obtained in comparable yield according to the procedure described for Example 2c, using 4-bromomethyl-N,N-diethyl-benzamide as the benzylating reagent.

EXAMPLE 61 rac-4-Chloro-N-(4-hydroxy-benzyl)-N-(2-oxo-azepan-3-yl)-benzenesulfonamide

The title compound, MS: m/e=409.2 (MH$^+$), 426.2 (MNH$_4^+$), was obtained in comparable yield according to the procedure described for Example 2c, using butyl-carbamic acid 4-chloromethyl-phenyl ester as the benzylating reagent.

EXAMPLE 62 rac-(4-{[(4-Chloro-benzenesulfonyl)-(2-oxo-azepan-3-yl)-amino]-methyl}-phenyl)-carbamic acid ethyl ester The title compound, MS: m/e=497.3 (MNH$_4^+$), was obtained in comparable yield according to the procedure described for Example 2c, using (4-chloromethyl-phenyl)-carbamic acid ethyl ester as the benzylating reagent.

EXAMPLE 63 rac-4-Chloro-N-(2-oxo-azepan-3-yl)-N-[4-(piperidine-1-carbonyl)-benzyl]-benzenesulfonamide The title compound, MS: m/e=504.4 (MH$^+$), 526.23 (MNa$^+$), was obtained in comparable yield according to the procedure described for Example 2c, using (4-chloromethyl-phenyl)-piperidin-1-yl-methanone as the benzylating reagent.

EXAMPLE 64 rac-4-{[(4-Chloro-benzenesulfonyl)-(2-oxo-azepan-3-yl)-amino]-methyl}-benzoic acid prop-2-ynyl ester The title compound, MS: m/e=475.3 (MH$^+$), 497.2 (MNa$^+$), was obtained in comparable yield according to the procedure described for Example 2c, using 4-chloromethyl-benzoic acid prop-2-ynyl ester as the benzylating reagent.

EXAMPLE 65 rac-4-Chloro-N-(4-formyl-benzyl)-N-(2-oxo-azepan-3-yl)-benzenesulfonamide

The title compound, MS: m/e=421.3 (MH$^+$), 443.2 (MNa$^+$), was obtained in comparable yield according to the procedure described for Example 2c, using 4-bromomethyl-benzaldehyde as the benzylating reagent.

EXAMPLE 66 rac-4-Chloro-N-(2-oxo-azepan-3-yl)-N-[4-(pyrrolidine-1-sulfonyl)-benzyl]-benzenesulfonamide The title compound, MS: m/e=526.2 (MH$^+$), 548.3 (MNa$^+$), was obtained in comparable yield according to the procedure described for Example 2c, using 1-(4-bromomethyl-benzenesulfonyl)-pyrrolidine as the benzylating reagent.

EXAMPLE 67 rac-4-Chloro-N-(2-fluoro-4-methoxy-benzyl)-N-(2-oxo-azepan-3-yl)-benzenesulfonamide The title compound, MS: m/e=441.4 (MH$^+$) 458.4 (MNH$_4^+$), was obtained in comparable yield analogous to the procedure described for Example 3, using (2-fluoro-4-methoxy-phenyl)-methanol as the alcohol.

EXAMPLE 68

4-Chloro-N-(2-fluoro-4-methoxy-benzyl)-N-((R)-2-oxo-azepan-3-yl)-benzenesulfonamide The title compound, MS: m/e=441.4 (MH$^+$) 458.4 (MNH$_4^+$), was obtained in comparable yield analogous to the procedure described for Example 3, using (2-fluoro-4-methoxy-phenyl)-methanol as the alcohol and the corresponding chiral sulfonamide.

EXAMPLE 69

4-Chloro-N-(4-hydroxy-benzyl)-N-((R)-2-oxo-azepan-3-yl)-benzenesulfonamide

The title compound, MS: m/e=409.2 (MH$^+$), 426.3 (MNH$_4^+$), was obtained in comparable yield according to the procedure described for Example 2c, using butyl-carbamic acid 4-chloromethyl-phenyl ester. The title compound was unexpectedly, the main product.

EXAMPLE 70

4-Chloro-N-[4-(4-hydroxy-benzyloxy)-benzyl]-N-((R)-2-oxo-azepan-3-yl)-benzenesulfonamide The title compound, MS: m/e=515.3 (MH$^+$), 532.3 (MNH$_4^+$), was obtained as a side product when following the procedure described for Example 2c, and using butyl-carbamic acid 4-chloromethyl-phenyl ester as the benzylating reagent.

EXAMPLE 71 rac-4-{[(4-Chloro-benzenesulfonyl)-(2-oxo-azepan-3-yl)-amino]-methyl}-benzoic acid rac-4-{[(4-Chloro-benzenesulfonyl)-(2-oxo-azepan-3-yl)-amino]-methyl}-benzoic acid methyl ester (0.95 g, 2.10 mmol) in a mixture of MeOH/CH$_3$CN (50 ml, 1:1 v/v) was treated with 1 N NaOH (2.5 ml) for 24 h. Solvent was removed under reduced pressure and the residue dissolved in ethyl acetate and washed with 5% KHSO$_4$/10% K$_2$SO$_4$ (2×). The aqueous washes were extracted with ethyl acetate and the combined organic fractions were washed with brine, dried (Na$_2$SO$_4$), filtered, concentrated under reduced pressure and lyophilized from water/CH$_3$CN: lyophilisate, 0.87 g; MS: m/e=435.2 (MH$^-$)

EXAMPLE 72 rac-N-Benzyl-4-chloro-N-(2-oxo-azepan-3-yl)-benzenesulfonamide

The title compound, MS: m/e=393.1 (MH$^+$), 410.4 (MNH$_4^+$), was obtained in comparable yield according to the procedure described for Example 2c, using bromomethyl-benzene as the benzylating reagent.

EXAMPLE 73 rac-4-Chloro-N-[4-(1-cyano-cyclopropyl)-benzyl]-N-(2-oxo-azepan-3-yl)-benzenesulfonamide The title compound, MS: m/e=458.4 (MH$^+$), 475.4 (MNH$_4^+$), was obtained in comparable yield according to the procedure described for Example 2c, using 1-(4-bromomethyl-phenyl)-cyclopropanecarbonitrile.

EXAMPLE 74 rac-1-(4-{[(4-Chloro-benzenesulfonyl)-(2-oxo-azepan-3-yl)-amino]-methyl}-phenyl)-cyclopropanecarboxylic acid methyl ester The title compound, MS: m/e=491.4 (MH$^+$), was obtained in comparable yield according to the procedure described for Example 2c, using 1-(4-bromomethyl-phenyl)-cyclopropanecarboxylic acid methyl ester.

EXAMPLE 75 rac-4-{[(4-Chloro-benzenesulfonyl)-(2-oxo-azepan-3-yl)-amino]-methyl}-N-cyclopropyl-benzamide rac-4-{[(4-Chloro-benzenesulfonyl)-(2-oxo-azepan-3-yl)-amino]-methyl}-benzoic acid (0.70 g, 1.6 mmol) was dissolved in DMF and activated with the coupling reagent TPTU (0.48 g, 1.6 mmol) and Hünig's base (0.55 ml, 3.2 mmol) for 2 min. ⅛ of this activated mixture was delivered to a reaction tube on a parallel synthesizer containing cyclopropylamine (0.013 g, 0.22 mmol) and a further amount of Hünig's base (0.04 ml, 0.22 mmol) in DMF (3 ml). The reaction mixture was shaken for 2 h, concentrated under reduced pressure and purified directly using preparative RP($C_{18}$) chromatography: lyophilisate 40 mg; MS: m/e=476.1 (MH$^+$), 493.1 (MNH$_4^+$).

EXAMPLE 76 rac-4-{[(4-Chloro-benzenesulfonyl)-(2-oxo-azepan-3-yl)-amino]-methyl}-N-methyl-benzamide The title compound, MS: m/e=450.3 (MH$^+$), 467.1 (MNH$_4^+$), was obtained in comparable yield according to the procedure described for Example 75, using methylamine in the coupling step.

EXAMPLE 77 rac-4-{[(4-Chloro-benzenesulfonyl)-(2-oxo-azepan-3-yl)-amino]-methyl}-N-(2,2,2-trifluoro-ethyl)-benzamide The title compound, MS: m/e=518.3 (MH$^+$), 535.4 (MNH$_4^+$), was obtained in comparable yield according to the procedure described for Example 75, using 2,2,2-trifluoro-ethylamine in the coupling step.

EXAMPLE 78 rac-4-{[(4-Chloro-benzenesulfonyl)-(2-oxo-azepan-3-yl)-amino]-methyl}-N-morpholin-4-yl-benzamide The title compound, MS: m/e=521.4 (MH$^+$), was obtained in comparable yield according to the procedure described for Example 75, using morpholin-4-ylamine in the coupling step.

EXAMPLE 79 rac-4-Chloro-N-[4-(N',N'-dimethyl-hydrazinocarbonyl)-benzyl]-N-(2-oxo-azepan-3-yl)-benzenesulfonamide The title compound, MS: m/e=479.1 (MH$^+$), was obtained in comparable yield according to the procedure described for Example 75, using N,N-dimethyl-hydrazine in the coupling step.

EXAMPLE 80 rac-4-{[(4-Chloro-benzenesulfonyl)-(2-oxo-azepan-3-yl)-amino]-methyl}-N-pyrrolidin-1-yl-benzamide The title compound, MS: m/e=505.4 (MH$^+$), was obtained in comparable yield according to the procedure described for Example 75, using pyrrolidin-1-ylamine in the coupling step.

EXAMPLE 81 rac-4-{[(4-Chloro-benzenesulfonyl)-(2-oxo-azepan-3-yl)-amino]-methyl}-N-piperidin-1-yl-benzamide The title compound, MS: m/e=519.5 (MH$^+$), was obtained in comparable yield according to the procedure described for Example 75, using piperidin-1-ylamine in the coupling step.

EXAMPLE 82

1-(4-1{[(4-Chloro-benzenesulfonyl)-((R)-2-oxo-azepan-3-yl)-amino]-methyl}-phenyl)-cyclopropanecarboxylic acid methyl ester The title compound, MS: m/e=491.3 (MH$^+$), 508.5 (MNH$_4^+$), was obtained in comparable yield according to the procedure described for Example 2c, using 1-(4-bromomethyl-phenyl)-cyclopropanecarboxylic acid methyl ester.

EXAMPLE 83

(4-{[(4-Chloro-benzenesulfonyl)-((R)-2-oxo-azepan-3-yl)-amino]-methyl}-phenyl)-acetic acid methyl ester The title compound, MS: m/e=465.3 (MH$^+$), 482.5 (MNH$_4^+$), was obtained in comparable yield according to the procedure described for Example 2c, using (4-bromomethyl-phenyl)-acetic acid methyl ester.

EXAMPLE 84

4-Chloro-N-(4-nitro-benzyl)-N-((R)-2-oxo-azepan-3-yl)-benzenesulfonamide

The title compound, MS: m/e=438.3 (MH$^+$), 455.5 (MNH$_4^+$), was obtained in comparable yield according to the procedure described for Example 2c, using 1-bromomethyl-4-nitro-benzene.

EXAMPLE 85 rac-Thiophene-2-sulfonic acid (3-fluoro-4-methoxy-benzyl)-(2-oxo-azepan-3-yl)-amide The title compound, MS: m/e=413.3 (MH$^+$), 435.3 (MNH$_4^+$), was obtained in comparable yield according to the procedure described for Example 1b, using thiophene-2-sulfonyl chloride.

EXAMPLE 86 rac-5-Bromo-thiophene-2-sulfonic acid (3-fluoro-4-methoxy-benzyl)-(2-oxo-azepan-3-yl)-amide The title compound, MS: m/e=491.2 (MH$^+$), 508.4 (MNH$_4^+$), was obtained in comparable yield according to the procedure described for Example 1b, using 5-bromo-thiophene-2-sulfonyl chloride.

EXAMPLE 87 rac-4,5-Dichloro-thiophene-2-sulfonic acid (3-fluoro-4-methoxy-benzyl)-(2-oxo-azepan-3-yl)-amide The title compound, MS: m/e=481.2 (MH$^+$), 503.2 (MNH$_4^+$), was obtained in comparable yield according to the procedure described for Example 1b, using 4,5-dichloro-thiophene-2-sulfonyl chloride.

EXAMPLE 88 rac5-Chloro-4-nitro-thiophene-2-sulfonic acid (3-fluoro-4-methoxy-benzyl)-(2-oxo-azepan-3-yl)-amide The title compound, MS: m/e=492.2 (MH$^+$), 509.4 (MNH$_4^+$), was obtained in comparable yield according to the procedure described for Example 1b, using 5-chloro-4-nitro-thiophene-2-sulfonyl chloride.

EXAMPLE 89 rac-3-Bromo-5-chloro-thiophene-2-sulfonic acid (3-fluoro-4-methoxy-benzyl)-(2-oxo-azepan-3-yl)-amide The title compound, MS: m/e=525.1 (MH$^+$), 542.1 (MNH$_4^+$), was obtained in comparable yield according to the procedure described for Example 1b, using 3-bromo-5-chloro-thiophene-2-sulfonyl chloride.

EXAMPLE 90 rac-5-Methyl-2-trifluoromethyl-furan-3-sulfonic acid (3-fluoro-4-methoxy-benzyl)-(2-oxo-azepan-3-yl)-amide The title compound, MS: m/e=479.4 (MH$^+$), 496.3 (MNH$_4^+$), was obtained in comparable yield according to the procedure described for Example 1b, using 5-methyl-2-trifluoromethyl-furan-3-sulfonyl chloride.

EXAMPLE 91 rac-2,5-Dichloro-thiophene-3-sulfonic acid (3-fluoro-4-methoxy-benzyl)-(2-oxo-azepan-3-yl)-amide The title compound, MS: m/e=481.3 (MH$^+$), 498.1 (MNH$_4^+$), was obtained in comparable yield according to the procedure described for Example 1b, using 2,5-dichloro-thiophene-3-sulfonyl chloride.

EXAMPLE 92

N-(4-Amino-benzyl)-4-chloro-N-((R)-2-oxo-azepan-3-yl)-benzenesulfonamide

4-Chloro-N-(4-nitro-benzyl)-N-((R)-2-oxo-azepan-3-yl)-benzenesulfonamide (0.10 g, 0.22 mmol) was dissolved in ethanol (15 ml) and treated with SnCl$_2$ (0.42 g, 2.2. mmol) overnight at 70° C. The reaction mixture was concentrated under reduced pressure and purified directly using preparative RP(C$_{18}$) chromatography: lyophilisate 27 mg; MS: m/e=408.2 (MH$^+$), 425.3 (MNH$_4^+$).

EXAMPLE 93

1-(4-{[(4-Chloro-benzenesulfonyl)-((R)-2-oxo-azepan-3-yl)-amino]-methyl}-phenyl)-cyclopropanecarboxylic acid 1-(4-{[(4-Chloro-benzenesulfonyl)-((R)-2-oxo-azepan-3-yl)-amino]-methyl}-phenyl)-cyclopropanecarboxylic acid methyl ester (0.03 g, 0.06 mmol) was dissolved in MeOH (1 ml) and treated with 1 N NaOH (0.07 ml) for 24 hr at 50° C. The reaction mixture was concentrated under reduced pressure and purified directly using preparative RP(C$_{18}$) chromatography: lyophilisate 8 mg; MS: m/e=475.0 (MH$^+$).

EXAMPLE 94

Cyclopropanecarboxylic acid (4-{[(4-chloro-benzenesulfonyl)-((R)-2-oxo-azepan-3-yl)-amino]-methyl}-phenyl)-amide N-(4-Amino-benzyl)-4-chloro-N-((R)-2-oxo-azepan-3-yl)-benzenesulfonamide (0.024 g, 0.06 mmol) was dissolved in CH$_2$Cl$_2$ (1 ml) and Hünig's base (0.01 ml, 0.07 mmol) and cyclopropanecarbonyl chloride (0.007 ml, 0.07 mmol) were added. After 30 min at r.t. the solvent was removed under reduced pressure and the residue dissolved in ethyl acetate and washed with 5% KHSO$_4$/10% K$_2$SO$_4$, brine, dried (Na$_2$SO$_4$), filtered and concentrated. The crude was purified using preparative RP(C$_{18}$) chromatography: lyophilisate 9 mg; MS: m/e=493.4 (MNH$_4^+$).

EXAMPLE 95 rac-N-Benzo[1,3]dioxol-5-ylmethyl-4-chloro-N-(2-oxo-azepan-3-yl)-benzenesulfonamide The title compound, MS: m/e=436.9 (MH$^+$), 459.0 (MNa$^+$), was obtained in comparable yield analogous to the procedure described for Example 3, using piperonyl alcohol and rac-4-chloro-N-(2-oxo-azepan-3-yl)-benzenesulfonamide.

EXAMPLE 96 rac-4-Chloro-N-(6-methoxy-pyridin-3-ylmethyl)-N-(2-oxo-azepan-3-yl)-benzenesulfonamide The title compound, MS: m/e=423.9 (MH$^+$), 445.9 (MNa$^+$), was obtained in comparable yield analogous to the procedure described for Example 3, using (6-methoxy-pyridin-3-yl)-methanol and rac-4-chloro-N-(2-oxo-azepan-3-yl)-benzenesulfonamide.

EXAMPLE 97 rac-4-Chloro-N-{3-methoxy-4-[2-(4-methyl-thiazol-5-yl)-ethoxy]-benzyl}-N-(2-oxo-azepan-3-yl)-benzenesulfonamide The title compound, MS: m/e=565.3 (MH$^+$), was obtained in comparable yield analogous to the procedure described for Example 3, using [3-methoxy-4-(2-(4-methyl-thiazol-5-yl)-ethoxy)-phenyl]-methanol (synthesized according to the procedure described for intermediate [3-Fluoro-4-(2-morpholin-4-yl-ethoxy)-phenyl]-methanol using 5-(2-chloroethyl)-4-methylthiazole) and rac-4-chloro-N-(2-oxo-azepan-3-yl)-benzenesulfonamide.

EXAMPLE 98 rac-4-{[(4-Chloro-benzenesulfonyl)-(2-oxo-azepan-3-yl)-amino]-methyl}-N-[1,2,4]triazol-4-yl-benzamide The title compound, MS: m/e=503.3 (MH$^+$), 525.3 (MNa$^+$), was obtained in comparable yield according to the procedure described for Example 75, using [1,2,4]triazol-4-ylamine in the coupling step.

EXAMPLE 99 rac-4-(2-{1-[(4-Chloro-benzenesulfonyl)-(2-oxo-azepan-3-yl)-amino]-ethyl}-phenyl)-butyric acid a) rac-4-(2-{1-[(4-Chloro-benzenesulfonyl)-(2-oxo-azepan-3-yl)-amino]-ethyl}-phenyl)-butyric acid methyl ester
rac-4-(2-{1-[(4-Chloro-benzenesulfonyl)-(2-oxo-azepan-3-yl)-amino]-ethyl}-phenyl)-butyric acid methyl ester, MS: m/e=524.4 (MNH$_4^+$), was obtained in comparable yield analogous to the procedure described for Example 3, using rac-2-(1-hydroxyethyl)-benzenebutanoic acid methyl ester as the alcohol.

b) rac-4-(2-{1-[(4-Chloro-benzenesulfonyl)-(2-oxo-azepan-3-yl)-amino]-ethyl}-phenyl)-butyric acid, MS: m/e=491.1 (M–H$^+$), was obtained by the following:
Rac-4-(2-{1-[(4-Chloro-benzenesulfonyl)-(2-oxo-azepan-3-yl)-amino]-ethyl}-phenyl)-butyric acid methyl ester (40 mg) was dissolved in methanol (1 ml) and treated with a solution of aqueous lithiumhydroxide (10 mg in 0.5 ml) for 1 hour. After evaporation of the methanol the pH is adjusted to 6 with 1N hydrochloric acid and the mixture was extracted with ethyl acetate to yield 31 mg of a solid. After chromatography (hexane/ethylacetate=1:1) 25 mg of the title compound were obtained.

EXAMPLE 100 rac-N-(3-Fluoro-4-methoxy-benzyl)-N-(2-oxo-azepan-3-yl)-4-trifluoromethoxy-benzenesulfonamide The title compound, MS: m/e=491.3 (MH$^+$), 508.5 (MNH$_4^+$), was obtained in comparable yield analogous to the procedure described for Example 1b, using 4-trifluoromethoxybenzenesulfonyl chlorid instead of 5-chloro-thiophene-2-sulfonyl chloride.

EXAMPLE 101 rac-N-(3-Fluoro-4-methoxy-benzyl)-N-(2-oxo-azepan-3-yl)-4-cyano-benzenesulfonamide The title compound, MS: m/e=432.4 (MH$^+$), 449.3 (MNH$_4^+$), was obtained in comparable yield analogous to the procedure described for Example 1b, using 4-cyanobenzenesulfonyl chlorid instead of 5-chloro-thiophene-2-sulfonyl chloride.

EXAMPLE 102

4-{[(4-Chloro-benzenesulfonyl)-(6,6-dimethyl-2-oxo-azepan-3-yl)-amino]-methyl}-N-cyclopropyl-benzamide The title compound, MS: m/e=504.4 (MH$^+$), 521.0 (MNH$_4^+$), was obtained in comparable yield analogous to the procedure described for Example 2c, using 4-chloromethyl-N-cyclopropyl-benzamide and 4-chloro-N-(6,6-dimethyl-2-oxo-azepan-3-yl)-benzenesulfonamide which was prepared analogous to Example 4e using 3-azidohexahydro-6,6-dimethyl-2H-azepin-2-one.

EXAMPLE 103 rac-4-Chloro-N-[1-(2,3-dihydro-benzo[1,4]dioxin-6-yl)-allyl]-N-(2-oxo-azepan-3-yl)-benzenesulfonamide The title compound, MS: m/e=532.1 (M–H$^+$), was obtained in comparable yield analogous to the procedure described for Example 99, using 1-(alpha-hydroxy-o-toluoyl)-proline-tert-butyl ester as the alcohol in step a) followed by the ester cleavage.

EXAMPLE 104

4-{[(4-Chloro-benzenesulfonyl)-(2-oxo-5-phenyl-azepan-3-yl)-amino]-methyl}-N-cyclopropyl-benzamide The title compound, MS: m/e=552.2 (MH$^+$), 569.4 (MNH$_4^+$), was obtained in comparable yield analogous to the procedure described for Example 2c, using 4-chloromethyl-N-cyclopropyl-benzamide and 4-chloro-N-(5-phenyl-2-oxo-azepan-3-yl)-benzenesulfonamide which was prepared analogous to Example 4e starting with 4-phenylcyclohexanone in Example 4a.

EXAMPLE 105

5-{[(4-Chloro-benzenesulfonyl)-(5-isopropyl-2-oxo-azepan-3-yl)-amino]-methyl}-pyridine-2-carboxylic acid cyclopropylamide The title compound, MS: m/e=519.0 (MH$^+$), 541.1 (MNa$^+$), was obtained in comparable yield analogous to the procedure described for Example 3, using 5-hydroxymethyl-pyridine-2-carboxylic acid cyclopropylamide and 4-chloro-N-(5-isopropyl-2-oxo-azepan-3-yl)-benzenesulfonamide in the Mitsunobu protocol.

EXAMPLE 106

N-Cyclopropyl-4-{[((R)-2-oxo-azepan-3-yl)-(4-trifluoromethyl-benzenesulfonyl)-amino]-methyl}-benzamide The title compound, MS: m/e=510.1 (MH$^+$), 531.9 (MNa$^+$), was obtained in comparable yield according to the procedure described for Example 2c, using 4-chloromethyl-N-cyclopropyl-benzamide and 4-trifluoromethyl-N-((R)-2-oxo-azepan-3-yl)-benzenesulfonamide.

EXAMPLE 107

N-Cyclopropyl-4-{[((R)-2-oxo-azepan-3-yl)-(4-bromo-benzenesulfonyl)-amino]-methyl}-benzamide The title compound, MS: m/e=520.0 (MH$^+$), 541.9 (MNa$^+$), was obtained in comparable yield according to the procedure described for Example 2c, using 4-chloromethyl- N-cyclopropyl-benzamide and 4-bromo-N-((R)-2-oxo-azepan-3-yl)-benzenesulfonamide.

EXAMPLE 108

4-{[(5-tert-Butyl-2-oxo-azepan-3-yl)-(4-chloro-benzenesulfonyl)-amino]-methyl}-N-cyclopropyl-benzamide The title compound, MS: m/e=532.0 (MH$^+$), 554.0 (MNa$^+$), was obtained in comparable yield analogous to the procedure described for Example 2c, using 4-chloromethyl-N-cyclopropyl-benzamide and 4-chloro-N-(5-tert-butyl-2-oxo-azepan-3-yl)-benzenesulfonamide which was prepared analogous to Example 4e starting with 4-tert-butyl cyclohexanone in Example 4a.

EXAMPLE 109

4-{[(4-Chloro-benzenesulfonyl)-(5,5-dimethyl-2-oxo-azepan-3-yl)-amino]-methyl}-N-cyclopropyl-benzamide The title compound, MS: m/e=504.0 (MH$^+$), 526.0 (MNa$^+$), was obtained in comparable yield analogous to the procedure described for Example 2c, using 4-chloromethyl-N-cyclopropyl-benzamide and 4-chloro-N-(5,5-dimethyl-2-oxo-azepan-3-yl)-benzenesulfonamide which was prepared analogous to Example 4e starting with 4,4-dimethyl cyclohexanone in Example 4a.

EXAMPLE 110

4-Chloro-N-((R)-2-oxo-azepan-3-yl)-N-pyridin-4-ylmethyl-benzenesulfonamide

The title compound, MS: m/e=394.2 (MH$^+$), was obtained in comparable yield analogous to the procedure described for Example 3, using pyridin-4-yl-methanol.

EXAMPLE 111

4-Chloro-N-(5-isopropyl-2-oxo-azepan-3-yl)-N-(4-methoxy-benzyl)-benzenesulfonamide The title compound, MS: m/e=465 (MH$^+$), 488.1 (MNa$^+$), was obtained in comparable yield analogous to the procedure described for Example 2c, using 4-methoxybenzyl chloride and 4-chloro-N-(5-isopropyl-2-oxo-azepan-3-yl)-benzenesulfonamide from Example 4e.

EXAMPLE 112

4-Chloro-N-(5-isopropyl-2-oxo-azepan-3-yl)-N-(3-methoxy-benzyl)-benzenesulfonamide The title compound, MS: m/e=465 (MH$^+$), was obtained in comparable yield analogous to the procedure described for Example 2c, using 3-methoxybenzyl chloride and 4-chloro-N-(5-isopropyl-2-oxo-azepan-3-yl)-benzenesulfonamide from Example 4e.

EXAMPLE 113

4-{[(4-Chloro-benzenesulfonyl)-(5-isopropyl-2-oxo-azepan-3-yl)-amino]-methyl}-benzoic acid methyl ester The title compound, MS: m/e=493 (MH$^+$), was obtained in comparable yield analogous to the procedure described for Example 2c, using Methyl 4-(bromomethyl)-benzoate and 4-chloro-N-(5-isopropyl-2-oxo-azepan-3-yl)-benzenesulfonamide from Example 4e.

EXAMPLE 114

4-Chloro-N-(3-fluoro-4-methoxy-benzyl)-N-(5-isopropyl-2-oxo-azepan-3-yl)-benzenesulfonamide The title compound, MS: m/e=483.0 (MH$^+$), 505.1 (MNa$^+$), was obtained in comparable yield analogous to the procedure described for Example 2c, using 3-fluoro-4-methoxybenzyl bromide and 4-chloro-N-(5-isopropyl-2-oxo-azepan-3-yl)-benzenesulfonamide from Example 4e.

EXAMPLE 115

4-{[(4-Chloro-benzenesulfonyl)-(2-oxo-5-trifluoromethyl-azepan-3-yl)-amino]-methyl}-N-cyclopropyl-benzamide The title compound, MS: m/e=543.9 (MH$^+$), was obtained in comparable yield analogous to the procedure described for Example 2c, using 4-chloromethyl-N-cyclopropyl-benzamide and 4-chloro-N-(5-trifluoromethyl-2-oxo-azepan-3-yl)-benzenesulfonamide which was prepared analogous to Example 4e starting with 4-trifluoromethyl cyclohexanone in Example 4a.

EXAMPLE 116

4-Chloro-N-(2-fluoro-4-methoxy-benzyl)-N-(5-isopropyl-2-oxo-azepan-3-yl)-benzenesulfonamide The title compound, MS: m/e=483.0 (MH$^+$), was obtained in comparable yield analogous to the procedure described for Example 3, using (2-fluoro-4-methoxy-phenyl)-methanol and 4-chloro-N-(5-isopropyl-2-oxo-azepan-3-yl)-benzenesulfonamide from Example 4e.

EXAMPLE 117

4-(2-{[(4-Chloro-benzenesulfonyl)-(2-oxo-azepan-3-yl)-amino]-methyl}-phenyl)-butyric acid methyl ester The title compound, MS: m/e=493.4 (MH$^+$), 510.5 (MNH$_4^+$), was obtained in comparable yield analogous to the procedure described for Example 3, using 4-(2-hydroxymethyl-phenyl)-butyric acid methyl ester as the alcohol in the Mitsunobu protocol.

EXAMPLE 118

4-(3-{[(4-Chloro-benzenesulfonyl)-(2-oxo-azepan-3-yl)-amino]-methyl}-phenyl)-butyric acid methyl ester The title compound, MS: m/e=493.4 (MH$^+$), 510.5 (MNH$_4^+$), was obtained in comparable yield analogous to the procedure described for Example 3, using 4-(3-hydroxymethyl-phenyl)-butyric acid methyl ester as the alcohol in the Mitsunobu protocol.

EXAMPLE 119

4-(3-{[(4-Chloro-benzenesulfonyl)-(2-oxo-azepan-3-yl)-amino]-methyl}-phenyl)-butyric acid The title compound, MS: m/e=477.1 (M−H$^+$) was obtained in comparable yield analogous to the procedure described for Example 99b from 4-(2-{[(4-chloro-benzenesulfonyl)-(2-oxo-azepan-3-yl)-amino]-methyl}-phenyl)-butyric acid methyl ester.

EXAMPLE 120

4-(3-{[(4-Chloro-benzenesulfonyl)-(2-oxo-azepan-3-yl)-amino]-methyl}-phenyl)-butyric acid The title compound, MS: m/e=477.1 (M−H$^+$), 537.1 (M+CH3COO$^−$) was obtained in comparable yield analogous to the procedure described for Example 99b from 4-(3-{[(4-chloro-benzenesulfonyl)-(2-oxo-azepan-3-yl)-amino]-methyl}-phenyl)-butyric acid methyl ester.

EXAMPLE 121 rac-3-{[(4-Chloro-benzenesulfonyl)-(2-oxo-azepan-3-yl)-amino]-methyl}-benzoic acid methyl ester The title compound, MS: m/e=450.4 (MH$^+$), was obtained in comparable yield according to the procedure described for Example 2c, using methyl 3-(bromomethyl)benzoate as the benzylating reagent.

EXAMPLE 122 rac-1-(3-{[(4-Chloro-benzenesulfonyl)-(2-oxo-azepan-3-yl)-amino]-methyl}-benzoyl)-piperidine-4-carboxylic acid ethyl ester Rac-3-{[(4-chloro-benzenesulfonyl)-(2-oxo-azepan-3-yl)-amino]-methyl}-benzoic acid methyl ester was converted into the corresponding acid according to example 99b. Then the title compound, MS: m/e=576.2 (MH$^+$), 593.4 (M+NH$_4^+$), was obtained in comparable yield according to the procedure described for Example 75, using rac-3-{[(4-chloro-benzenesulfonyl)-(2-oxo-azepan-3-yl)-amino]-methyl}-benzoic acid as the acid and piperidine-4-carboxylic acid ethyl ester as the amine in the coupling step.

EXAMPLE 123 rac-[1-(3-{[(4-Chloro-benzenesulfonyl)-(2-oxo-azepan-3-yl)-amino]-methyl}-benzoyl)-piperidin-4-yl]-acetic acid ethyl ester Rac-3-{[(4-chloro-benzenesulfonyl)-(2-oxo-azepan-3-yl)-amino]-methyl}-benzoic acid methyl ester was converted into the corresponding acid according to example 99b. Then the title compound, MS: m/e=590.5 (MH$^+$), 607.3 (M+NH$_4^+$), was obtained in comparable yield according to the procedure described for Example 75, using rac-3-{[(4-chloro-benzenesulfonyl)-(2-oxo-azepan-3-yl)-amino]-methyl}-benzoic acid as the acid and piperidin-4-yl-acetic acid ethyl ester as the amine in the coupling step.

EXAMPLE 124

(3S)-2-(3-{[(4-Chloro-benzenesulfonyl)-((3RS)-2-oxo-azepan-3-yl)-amino]-methyl}-benzoylamino)-3-methyl-butyric acid tert-butyl ester Rac-3-{[(4-chloro-benzenesulfonyl)-(2-oxo-azepan-3-yl)-amino]-methyl}-benzoic acid methyl ester was converted into the corresponding acid according to example 99b. Then the title compound, MS: m/e=609.4 (M+NH$_4^+$) was obtained in comparable yield according to the procedure described for Example 75, using rac-3-{[(4-chloro-benzenesulfonyl)-(2-oxo-azepan-3-yl)-amino]-methyl}-benzoic acid as the acid and L-valin-tert.-butylester hydrochloride as the amine in the coupling step.

EXAMPLE 125 rac-(3-{[(4-Chloro-benzenesulfonyl)-(2-oxo-azepan-3-yl)-amino]-methyl}-benzoylamino)-acetic acid tert-butyl ester Rac-3-{[(4-chloro-benzenesulfonyl)-(2-oxo-azepan-3-yl)-amino]-methyl}-benzoic acid methyl ester was converted into the corresponding acid according to example 99b. Then the title compound, MS: m/e=567.4 (M+NH$_4^+$) was obtained in comparable yield according to the procedure described for Example 75, using rac-3-{[(4-chloro-benzenesulfonyl)-(2-oxo-azepan-3-yl)-amino]-methyl}-benzoic acid as the acid and glycine tert.-butylester hydrochloride as the amine in the coupling step.

EXAMPLE 126 rac-3-(3-{[(4-Chloro-benzenesulfonyl)-(2-oxo-azepan-3-yl)-amino]-methyl}-benzoylamino)-propionic acid tert-butyl ester Rac-3-{[(4-chloro-benzenesulfonyl)-(2-oxo-azepan-3-yl)-amino]-methyl}-benzoic acid methyl ester was converted into the corresponding acid according to example 99b. Then the title compound, MS: m/e=581.3 (M+NH$_4^+$) was obtained in comparable yield according to the procedure described for Example 75, using rac-3-{[(4-chloro-benzenesulfonyl)-(2-oxo-azepan-3-yl)-amino]-methyl}-benzoic acid as the acid and beta-alanine tert.-butylester hydrochloride as the amine in the coupling step.

EXAMPLE 127

Rac-(3-{[(4-Chloro-benzenesulfonyl)-(2-oxo-azepan-3-yl)-amino]-methyl}-phenoxy)-acetic acid The title compound, MS: m/e=467.4 (MH$^+$), 484.5 (M+NH$_4^+$) was obtained in comparable yield according to the procedure described for Example 2c, using 3-bromomethyl phenoxyacetic acid ethyl ester as the benzylating reagent followed by saponification of the ester according to the procedure described in example 99b.

EXAMPLE 128

Rac-4-Chloro-N-(5,5-dimethyl-2-oxo-azepan-3-yl)-N-(4-trifluoromethyl-benzyl)-benzenesulfonamide The title compound, MS: m/e=489.1 (MH$^+$), 506.1 (M+NH$_4^+$) was obtained in comparable yield according to the procedure described for Example 2c, using 4-(trifluoromethyl)benzyl bromide as the benzylating reagent and 4-chloro-N-(6,6-dimethyl-2-oxo-azepan-3-yl)-benzenesulfonamide which was prepared analogous to Example 4e using 3-azidohexahydro-6,6-dimethyl-2H-azepin-2-one.

EXAMPLE 129

Rac-4-Chloro-N-(4-cyano-benzyl)-N-(5,5-dimethyl-2-oxo-azepan-3-yl)-benzenesulfonamide The title compound, MS: m/e=446.0 (MH$^+$), 463.0 (M+NH$_4^+$) was obtained in comparable yield according to the procedure described for Example 2c, using 4-(bromomethyl)benzonitrile as the benzylating reagent and 4-chloro-N-(6,6-dimethyl-2-oxo-azepan-3-yl)-benzenesulfonamide which was prepared analogous to Example 4e using 3-azidohexahydro-6,6-dimethyl-2H-azepin-2-one.

EXAMPLE 130

Rac-4-Chloro-N-(6-chloro-pyridin-3-ylmethyl)-N-(5,5-dimethyl-2-oxo-azepan-3-yl)-benzenesulfonamide The title compound, MS: m/e=456.2 (MH$^+$) was obtained in comparable yield according to the procedure described for Example 2c, using 2-chloro-5-chloromethylpyridine as the alkylating reagent and 4-chloro-N-(6,6-dimethyl-2-oxo-azepan-3-yl)-benzenesulfonamide which was prepared analogous to Example 4e using 3-azidohexahydro-6,6-dimethyl-2H-azepin-2-one.

EXAMPLE 131 rac-3-{[(4-Chloro-benzenesulfonyl)-(2-oxo-azepan-3-yl)-amino]-methyl}-N-cyclopentyl-benzamide Rac-3-{[(4-chloro-benzenesulfonyl)-(2-oxo-azepan-3-yl)-amino]-methyl}-benzoic acid methyl ester was converted into the corresponding acid according to example 99b. Then the title compound, MS: m/e=504.2 (MH$^+$), 521.3 (M+NH$_4^+$) was obtained in comparable yield according to the procedure described for Example 75, using rac-3-{[(4-chloro-benzenesulfonyl)-(2-oxo-azepan-3-yl)-amino]-methyl}-benzoic acid as the acid and cyclopentylamine as the amine in the coupling step.

EXAMPLE 132 rac-4-Chloro-N-(2-oxo-azepan-3-yl)-N-[3-(piperidine-1-carbonyl)-benzyl]-benzenesulfonamide Rac-3-{[(4-chloro-benzenesulfonyl)-(2-oxo-azepan-3-yl)-amino]-methyl}-benzoic acid methyl ester was converted into the corresponding acid according to example 99b. Then the title compound, MS: m/e=504.2 (MH$^+$), was obtained in comparable yield according to the procedure described for Example 75, using rac-3-{[(4-chloro-benzenesulfonyl)-(2-oxo-azepan-3-yl)-amino]-methyl}-benzoic acid as the acid and piperidine as the amine in the coupling step.

EXAMPLE 133 rac-4-Chloro-N-(2-oxo-azepan-3-yl)-N-[3-(4,4-difluoro-piperidine-1-carbonyl)-benzyl]-benzenesulfonamide Rac-3-{[(4-chloro-benzenesulfonyl)-(2-oxo-azepan-3-yl)-amino]-methyl}-benzoic acid methyl ester was converted into the corresponding acid according to example 99b. Then the title compound, MS: m/e=540.3 (MH$^+$), was obtained in comparable yield according to the procedure described for Example 75, using rac-3-{[(4-chloro-benzenesulfonyl)-(2-oxo-azepan-3-yl)-amino]-methyl}-benzoic acid as the acid and 4,4-difluoropiperidine as the amine in the coupling step.

EXAMPLE 134 rac-4-Chloro-N-(2-oxo-azepan-3-yl)-N-[3-(2,6-dimethyl-piperidine-1-carbonyl)-benzyl]-benzenesulfonamide Rac-3-{[(4-chloro-benzenesulfonyl)-(2-oxo-azepan-3-yl)-amino]-methyl}-benzoic acid methyl ester was converted into the corresponding acid according to example 99b. Then the title compound, MS: m/e=532.3 (MH$^+$), was obtained in comparable yield according to the procedure described for Example 75, using rac-3-{[(4-chloro-benzenesulfonyl)-(2-oxo-azepan-3-yl)-amino]-methyl}-benzoic acid as the acid and 2,6-dimethylperidine as the amine in the coupling step.

EXAMPLE 135 rac-4-Chloro-N-(2-oxo-azepan-3-yl)-N-[3-(4-fluoro-piperidine-1-carbonyl)-benzyl]-benzenesulfonamide Rac-3-{[(4-chloro-benzenesulfonyl)-(2-oxo-azepan-3-yl)-amino]-methyl}-benzoic acid methyl ester was converted into the corresponding acid according to example 99b. Then the title compound, MS: m/e=522.3 (MH$^+$), was obtained in comparable yield according to the procedure described for Example 75, using rac-3-{[(4-chloro-benzenesulfonyl)-(2-oxo-azepan-3-yl)-amino]-methyl}-benzoic acid as the acid and 4-fluoropiperidine as the amine in the coupling step.

EXAMPLE 136 rac-4-Chloro-N-(2-oxo-azepan-3-yl)-N-[3-(3,3-difluoro-piperidine-1-carbonyl)-benzyl]-benzenesulfonamide Rac-3-{[(4-chloro-benzenesulfonyl)-(2-oxo-azepan-3-yl)-amino]-methyl}-benzoic acid methyl ester was converted into the corresponding acid according to example 99b. Then the title compound, MS: m/e=540.3 (MH$^+$), was obtained in comparable yield according to the procedure described for Example 75, using rac-3-{[(4-chloro-benzenesulfonyl)-(2-oxo-azepan-3-yl)-amino]-methyl}-benzoic acid as the acid and 3,3-difluoropiperidine as the amine in the coupling step.

EXAMPLE 137 rac-4-Chloro-N-(2-oxo-azepan-3-yl)-N-[3-(3,3-difluoro-pyrrolidine-1-carbonyl)-benzyl]-benzenesulfonamide Rac-3-{[(4-chloro-benzenesulfonyl)-(2-oxo-azepan-3-yl)-amino]-methyl}-benzoic acid methyl ester was converted into the corresponding acid according to example 99b. Then the title compound, MS: m/e=526.1 (MH$^+$), was obtained in comparable yield according to the procedure described for Example 75, using rac-3-{[(4-chloro-benzenesulfonyl)-(2-oxo-azepan-3-yl)-amino]-methyl}-benzoic acid as the acid and 3,3-difluoropyrrolidine as the amine in the coupling step.

EXAMPLE 138

Rac-4-{[(4-Chloro-benzenesulfonyl)-(5,5-dimethyl-2-oxo-azepan-3-yl)-amino]-methyl}-benzoic acid methyl ester The title compound, MS: m/e=479.1 (MH$^+$), 496.1 (M+NH$_4^+$) was obtained in comparable yield according to the procedure described for Example 2c, using methyl 4-(chloromethyl)benzoate as the benzylating reagent and 4-chloro-N-(6,6-dimethyl-2-oxo-azepan-3-yl)-benzenesulfonamide which was prepared analogous to Example 4e using 3-azidohexahydro-6,6-dimethyl-2H-azepin-2-one.

EXAMPLE 139

4-{[(4-Chloro-benzenesulfonyl)-(5,5-dimethyl-2-oxo-azepan-3-yl)-amino]-methyl}-benzoic acid The title compound, MS: m/e=463.4 (M–H$^+$) was obtained in comparable yield analogous to the procedure described for Example 99b from 4-{[(4-Chloro-benzenesulfonyl)-(5,5-dimethyl-2-oxo-azepan-3-yl)-amino]-methyl}-benzoic acid methyl ester.

EXAMPLE 140 rac-4-{[(4-Chloro-benzenesulfonyl)-(5,5-dimethyl-2-oxo-azepan-3-yl)-amino]-methyl}-N-(2-fluoro-ethyl)-benzamide The title compound, MS: m/e=510.4 (MH$^+$), 527.2 (M+NH$_4^+$) was obtained in comparable yield according to the procedure described for Example 75, using 4-{[(4-Chloro-benzenesulfonyl)-(5,5-dimethyl-2-oxo-azepan-3-yl)-amino]-methyl}-benzoic acid as the acid and 2-fluoro-ethylamine as the amine in the coupling step.

EXAMPLE 141 rac-4-{[(4-Chloro-benzenesulfonyl)-(5,5-dimethyl-2-oxo-azepan-3-yl)-amino]-methyl}-N-(2,2,2-trifluoro-ethyl)-benzamide The title compound, MS: m/e=546.3 (MH$^+$), 563.3 (M+NH$_4^+$) was obtained in comparable yield according to the procedure described for Example 75, using 4-{[(4-Chloro-benzenesulfonyl)-(5,5-dimethyl-2-oxo-azepan-3-yl)-amino]-methyl}-benzoic acid as the acid and 2,2,2-trifluoroethylamine as the amine in the coupling step.

EXAMPLE 142 rac-4-{[(4-Chloro-benzenesulfonyl)-(5,5-dimethyl-2-oxo-azepan-3-yl)-amino]-methyl}-N-((1R,2S)-2-fluoro-cyclopropyl)-benzamide The title compound, MS: m/e=522.3 (MH$^+$), 539.4 (M+NH$_4^+$) was obtained in comparable yield according to the procedure described for Example 75, using 4-{[(4-Chloro-benzenesulfonyl)-(5,5-dimethyl-2-oxo-azepan-3-yl)-amino]-methyl}-benzoic acid as the acid and 2-fluoro-cyclopropylamine as the amine in the coupling step.

EXAMPLE 143 rac-4-{[(4-Chloro-benzenesulfonyl)-(5,5-dimethyl-2-oxo-azepan-3-yl)-amino]-methyl}-N-(2-hydroxy-ethyl)-benzamide The title compound, MS: m/e=508.3 (MH$^+$) was obtained in comparable yield according to the procedure described for Example 75, using 4-{[(4-Chloro-benzenesulfonyl)-(5,5-dimethyl-2-oxo-azepan-3-yl)-amino]-methyl}-benzoic acid as the acid and 2-aminoethanol as the amine in the coupling step.

EXAMPLE 144 rac-4-{[(4-Chloro-benzenesulfonyl)-(5,5-dimethyl-2-oxo-azepan-3-yl)-amino]-methyl}-N-cyclopentyl-benzamide The title compound, MS: m/e=532.2 (MH$^+$), 549.4 (M+NH$_4^+$) was obtained in comparable yield according to the procedure described for Example 75, using 4-{[(4-Chloro-benzenesulfonyl)-(5,5-dimethyl-2-oxo-azepan-3-yl)-amino]-methyl}-benzoic acid as the acid and cyclopentylamine as the amine in the coupling step.

EXAMPLE 145 rac-4-{[(4-Chloro-benzenesulfonyl)-(5,5-dimethyl-2-oxo-azepan-3-yl)-amino]-methyl}-N-methyl-benzamide The title compound, MS: m/e=478.2 (MH$^+$), 495.3 (M+NH$_4^+$) was obtained in comparable yield according to the procedure described for Example 75, using 4-{[(4-Chloro-benzenesulfonyl)-(5,5-dimethyl-2-oxo-azepan-3-yl)-amino]-methyl}-benzoic acid as the acid and methylamine hydrochloride as the amine in the coupling step.

EXAMPLE 146 rac-4-{[(4-Chloro-benzenesulfonyl)-(5,5-dimethyl-2-oxo-azepan-3-yl)-amino]-methyl}-benzamide The title compound, MS: m/e=464.2 (MH$^+$), 481.2 (M+NH$_4^+$) was obtained in comparable yield according to the procedure described for Example 75, using 4-{[(4-Chloro-benzenesulfonyl)-(5,5-dimethyl-2-oxo-azepan-3-yl)-amino]-methyl}-benzoic acid as the acid and ammonia in methanol (7M solution) as the amine in the coupling step.

EXAMPLE 147 rac-N-Benzyl-4-{[(4-chloro-benzenesulfonyl)-(5,5-dimethyl-2-oxo-azepan-3-yl)-amino]-methyl}-benzamide The title compound, MS: m/e=554.3 (MH$^+$), 571.3 (M+NH$_4^+$) was obtained in comparable yield according to the procedure described for Example 75, using 4-{[(4-Chloro-benzenesulfonyl)-(5,5-dimethyl-2-oxo-azepan-3-yl)-amino]-methyl}-benzoic acid as the acid and benzylamine as the amine in the coupling step.

EXAMPLE 148 rac-(4-{[(4-Chloro-benzenesulfonyl)-(5,5-dimethyl-2-oxo-azepan-3-yl)-amino]-methyl}-benzoylamino)-acetic acid methyl ester The title compound, MS: m/e=536.3 (MH$^+$), 553.3 (M+NH$_4^+$) was obtained in comparable yield according to the procedure described for Example 75, using 4-{[(4-Chloro-benzenesulfonyl)-(5,5-dimethyl-2-oxo-azepan-3-yl)-amino]-methyl}-benzoic acid as the acid and glycine methylester hydrochloride as the amine in the coupling step.

EXAMPLE 149 rac-4-{[(4-Chloro-benzenesulfonyl)-(5,5-dimethyl-2-oxo-azepan-3-yl)-amino]-methyl}-N-(2-morpholin-4-yl-ethyl)-benzamide The title compound, MS: m/e=577.4 (MH$^+$) was obtained in comparable yield according to the procedure described for Example 75, using 4-{[(4-Chloro-benzenesulfonyl)-(5,5-dimethyl-2-oxo-azepan-3-yl)-amino]-methyl}-benzoic acid as the acid and 2-(morpholin-4-yl)-ethylamine hydrochloride as the amine in the coupling step.

EXAMPLE 150 rac-4-Chloro-N-(5,5-dimethyl-2-oxo-azepan-3-yl)-N-[4-(2H-tetrazol-5-yl)-benzyl]-benzenesulfonamide Rac-4-Chloro-N-(4-cyano-benzyl)-N-(5,5-dimethyl-2-oxo-azepan-3-yl)-benzenesulfonamide (80 mg, 0.18 mmol) was dissolved in dimethylformamide (1 ml). Then ammonium chloride (11 mg, 0.2 mmol) and sodium azide (13 mg, 0.2 mmol) was added and the mixture was stirred overnight at 120° C. After cooling the mixture was distributed 3 times between ethyl acetate (10 ml) and hydrochloric acid (10 ml 1N). The combined organic layers were dried and evaporated. The residue was purified on silica gel (eluent hexane/ethyl acetate) to yield 79 mg (89%). MS: m/e=506.1 (M+NH$_4^+$).

EXAMPLE 151 rac-(4-{[(4-Chloro-benzenesulfonyl)-(5,5-dimethyl-2-oxo-azepan-3-yl)-amino]-methyl}-phenyl)-carbamic acid ethyl ester The title compound, MS: m/e=446.0 (MH$^+$), 463.0 (M+NH$_4^+$) was obtained in comparable yield according to the procedure described for Example 2c, using (4-chloromethyl-phenyl)-carbamic acid ethyl ester as the benzylating reagent and 4-chloro-N-(6,6-dimethyl-2-oxo-azepan-3-yl)-benzenesulfonamide which was prepared analogous to Example 4e using 3-azidohexahydro-6,6-dimethyl-2H-azepin-2-one.

EXAMPLE 152 rac-N-(4-{[(4-Chloro-benzenesulfonyl)-(5,5-dimethyl-2-oxo-azepan-3-yl)-amino]-methyl}-phenyl)-acetamide The title compound, MS: m/e=495.2 (M+NH$_4^+$) was obtained in comparable yield according to the procedure described for Example 2c, using 4-acetamido benzylchloride as the benzylating reagent and 4-chloro-N-(6,6-dimethyl-2-oxo-azepan-3-yl)-benzenesulfonamide which was prepared analogous to Example 4e using 3-azidohexahydro-6,6-dimethyl-2H-azepin-2-one.

EXAMPLE 153 rac-Cyclopropanecarboxylic acid (4-{[(2-oxo-azepan-3-yl)-(4-trifluoromethyl-benzenesulfonyl)-amino]-methyl}-phenyl)-amide a) rac-4-Trifluoromethyl-benzenesulfonic acid (4-nitro-benzyl)-(2-oxo-azepan-3-yl)-amide rac-4-Trifluoromethyl-benzenesulfonic acid (4-nitro-benzyl)-(2-oxo-azepan-3-yl)-amide was obtained in comparable yield according to the procedure described for Example 1, using 4-nitrobenzaldehyde instead of 3-fluoro-p-anisaldehyde in step 1a and trifluoromethyl-benzenesulfonyl chloride instead of 5-chloro-thiophene-2-sulfonyl chloride in step 1b).

b) rac-4-Trifluoromethyl-benzenesulfonic acid (4-amino-benzyl)-(2-oxo-azepan-3-yl)-amide Rac-4-trifluoromethyl-benzenesulfonic acid (4-nitro-benzyl)-(2-oxo-azepan-3-yl)-amide (2.08 g, 4.4 mmol) was dissolved in methanol (50 ml), palladium on charcoal (200 mg, 10%) was added and the mixture was hydrogenated at room temperature for 2 hours. The catalyst was filtered off and the filtrate was evaporated. The residue was recrystallised from heptane/ethyl acetate to yield a yellowish solid (1.2 g, 61%).

c) rac-Cyclopropanecarboxylic acid (4-{[(2-oxo-azepan-3-yl)-(4-trifluoromethyl-benzenesulfonyl)-amino]-methyl}-phenyl)-amide Rac-4-trifluoromethyl-benzenesulfonic acid (4-amino-benzyl)-(2-oxo-azepan-3-yl)-amide (75 mg, 0.17 mmol) is dissolved in dichloromethane (2 ml), then pyridine (80 mg, 1 mmol) and cyclopropanecarbonyl chloride (21 mg, 0.2 mmol) were added. After shaking the mixture at room temperature for 1 hour hydrochloric acid (5 ml, 0.1M) was added. The organic layer was separated evaporated and the residue was redissolved in 1 ml of dimethylformamide for preparative HPLC separation (RP—C$_{18}$, eluent acetonitrile/water) to yield 12 mg (14% of the final product). MS: m/e=510.4 (MH$^+$), 527.2 (M+NH$_4^+$).

EXAMPLE 154 rac-Cyclohexanecarboxylic acid (4-{[(2-oxo-azepan-3-yl)-(4-trifluoromethyl-benzenesulfonyl)-amino]-methyl}-phenyl)-amide The title compound, MS: m/e=552.3 (MH$^+$), 569.5 (M+NH$_4^+$), was obtained in comparable yield analogous to the procedure described for Example 153, using cyclohexanecarbonyl chloride instead of cyclopropanecarbonyl chloride in step 153c).

EXAMPLE 155 rac-2-Methoxy-N-(4-{[(2-oxo-azepan-3-yl)-(4-trifluoromethyl-benzenesulfonyl)-amino]-methyl}-phenyl)-acetamide The title compound, MS: m/e=514.3 (MH$^+$), 531.2 (M+NH$_4^+$), was obtained in comparable yield analogous to the procedure described for Example 153, using methoxyacetyl chloride instead of cyclopropanecarbonyl chloride in step 153c).

EXAMPLE 156 rac-N-(4-{[(2-Oxo-azepan-3-yl)-(4-trifluoromethyl-benzenesulfonyl)-amino]-methyl}-phenyl)-malonamic acid ethyl ester The title compound, MS: m/e=556.2 (MH$^+$), 573.3 (M+NH$_4^+$), was obtained in comparable yield analogous to the procedure described for Example 153, using ethyl malonyl chloride instead of cyclopropanecarbonyl chloride in step 153c).

EXAMPLE 157 rac-N-(4-{[(2-Oxo-azepan-3-yl)-(4-trifluoromethyl-benzenesulfonyl)-amino]-methyl}-phenyl)-2-phenyl-acetamide The title compound, MS: m/e=560.2 (MH$^+$), 577.4 (M+NH$_4^+$), was obtained in comparable yield analogous to the procedure described for Example 153, using phenylacetyl chloride instead of cyclopropanecarbonyl chloride in step 153c).

EXAMPLE 158 rac-Isoxazole-5-carboxylic acid (4-{[(2-oxo-azepan-3-yl)-(4-trifluoromethyl-benzenesulfonyl)-amino]-methyl}-phenyl)-amide The title compound, MS: m/e=537.2 (MH$^+$), 554.4 (M+NH$_4^+$), was obtained in comparable yield analogous to the procedure described for Example 153, using isoxazole-5-carbonyl chloride instead of cyclopropanecarbonyl chloride in step 153c).

EXAMPLE 159 rac-N-(4-{[(2-Oxo-azepan-3-yl)-(4-trifluoromethyl-benzenesulfonyl)-amino]-methyl}-phenyl)-benzamide The title compound, MS: m/e=546.3 (MH$^+$), 563.3 (M+NH$_4^+$), was obtained in comparable yield analogous to the procedure described for Example 153, using benzoyl chloride instead of cyclopropanecarbonyl chloride in step 153c).

EXAMPLE 160

Rac-4-{[(4-Chloro-benzenesulfonyl)-(2-oxo-azepan-3-yl)-amino]-methyl}-N-cyclopropyl)-benzenesulfonamide The title compound, MS: m/e=512.1 (MH$^+$), 529.1 (M+NH$_4^+$), was obtained in comparable yield analogous to the procedure described for Example 1, using N-cyclopropyl-4-formyl-benzenesulfonamide instead of 3-fluoro-p-anisaldehyde in step 1a).

EXAMPLE 161 rac-N-(3-Amino-benzyl)-4-chloro-N-(2-oxo-azepan-3-yl)-benzenesulfonamide

The title compound, MS: m/e=408.0 (MH$^+$), 425.1 (M+NH$_4^+$), was obtained in comparable yield analogous to the procedure described for Example 92, using 4-chloro-N-(3-nitro-benzyl)-N-((R)-2-oxo-azepan-3-yl)-benzenesulfonamide instead of 4-chloro-N-(4-nitro-benzyl)-N-((R)-2-oxo-azepan-3-yl)-benzenesulfonamide.

EXAMPLE 162 rac-4-Chloro-N-(4-methanesulfonylamino-benzyl)-N-(2-oxo-azepan-3-yl)-benzenesulfonamide The title compound, MS: m/e=484.2 (M–H$^+$), was obtained in comparable yield analogous to the procedure described for Example 94, using methanesulfonyl chloride instead of cyclopropanecarbonyl chloride.

EXAMPLE 163 rac-Cyclopropanecarboxylic add (3-{[(4-chloro-benzenesulfonyl)-(2-oxo-azepan-3-yl)-amino]-methyl}-phenyl)-amide The title compound, MS: m/e=476.0 (MH$^+$), 493.1 (M+NH$_4^+$), was obtained in comparable yield analogous to the procedure described for Example 94, using N-(3-amino-benzyl)-4-chloro-N-((R)-2-oxo-azepan-3-yl)-benzenesulfonamide instead of N-(4-amino-benzyl)-4-chloro-N-((R)-2-oxo-azepan-3-yl)-benzenesulfonamide.

EXAMPLE 164 rac-4-Chloro-N-(3-methanesulfonylamino-benzyl)-N-(2-oxo-azepan-3-yl)-benzenesulfonamide The title compound, MS: m/e=484.10 (M–H$^+$), was obtained in comparable yield analogous to the procedure described for Example 94, using N-(3-amino-benzyl)-4-chloro-N-((R)-2-oxo-azepan-3-yl)-benzenesulfonamide instead of N-(4-amino-benzyl)-4-chloro-N-((R)-2-oxo-azepan-3-yl)-benzenesulfonamide and methanesulfonyl chloride instead of cyclopropanecarbonyl chloride.

EXAMPLE 165

Rac-N-(4-{[(4-Chloro-benzenesulfonyl)-(2-oxo-azepan-3-yl)-amino]-methyl}-phenyl)-malonamic acid ethyl ester The title compound, MS: m/e=522.1 (MH$^+$), 539.3 (M+NH$_4{}^+$), was obtained in comparable yield analogous to the procedure described for Example 94, using ethyl malonyl chloride instead of cyclopropanecarbonyl chloride.

EXAMPLE 166

N-(2,3-Difluoro-4-methoxy-benzyl)-N-((R)-2-oxo-azepan-3-yl)-4-trifluoromethyl-benzenesulfonamide The title compound, MS: m/e=493.1 (MH$^+$), 510.3 (MNH$_4{}^+$), was obtained in comparable yield analogous to the procedure described for Example 2, using 4-trifluoromethyl-N-((R)-2-oxo-azepan-3-yl)-benzenesulfonamide instead of 4-chloro-N-((R)-2-oxo-azepan-3-yl)-benzenesulfonamide and 1-bromomethyl-2,3-difluoro-4-methoxy-benzene as the benzylbromide in step 2c, which was previously prepared from 2,3-difluoro-4-methylanisole analogous to the bromination protocol described in Example 185.

EXAMPLE 167

3-Methyl-3-(4-{[((R)-2-oxo-azepan-3-yl)-(4-trifluoromethyl-benzenesulfonyl)-amino]-methyl}-phenyl)-butyric acid methyl ester The title compound, MS: m/e=558.2 (MNH$_4{}^+$), was obtained in comparable yield analogous to the procedure described for Example 2, using 4-trifluoromethyl-N-((R)-2-oxo-azepan-3-yl)-benzenesulfonamide instead of 4-chloro-N-((R)-2-oxo-azepan-3-yl)-benzenesulfonamide and 3-(4-bromomethyl-phenyl)-3-methyl-butyric acid methyl ester as the benzyl bromide in step 2c, which was previously prepared from 3-methyl-3-phenyl-butyric acid analogous to the bromomethylation and esterifaction sequence described in Example 190 and from the literature (U.S. Pat. No. 4,032,533).

EXAMPLE 168

N-(2-Fluoro-4-methoxy-benzyl)-N-((R)-2-oxo-azepan-3-yl)-4-trifluoromethyl-benzenesulfonamide The title compound, MS: m/e=475.0 (MH$^+$), 492.0 (MNH$_4{}^+$), was obtained in comparable yield analogous to the procedure described for Example 3, using 4-trifluoromethyl-N-((R)-2-oxo-azepan-3-yl)-benzenesulfonamide instead of 4-chloro-N-((R)-2-oxo-azepan-3-yl)-benzenesulfonamide and (2-fluoro-4-methoxy-phenyl)-methanol in the Mitsunobu protocol.

EXAMPLE 169

3-Methyl-3-(4-{[((R)-2-oxo-azepan-3-yl)-(4-trifluoromethyl-benzenesulfonyl)-amino]-methyl}-phenyl)-butyric acid The title compound, MS: m/e=525.1 (M–H$^+$), 585.1 (M+CH3COO$^-$) was obtained in comparable yield analogous to the procedure described for Example 99b from 3-methyl-3-(4-{[((R)-2-oxo-azepan-3-yl)-(4-trifluoromethyl-benzenesulfonyl)-amino]-methyl}-phenyl)-butyric acid methyl ester.

EXAMPLE 170

Rac-4-Chloro-N-(2-oxo-azepan-3-yl)-N-(4-pyrazol-1-yl-benzyl)-benzenesulfonamide

4-Chloro-N-(2-oxo-azepan-3-yl)-benzenesulfonamide (0.16 g, 0.52 mmol), 1-[4-(bromomethyl)phenyl]-1H-pyrazole (0.26 g, 1.03 mmol), potassium carbonate (0.72 g, 5.17 mmol) and potassium iodide (0.02 g, 0.10 mmol) in 5 ml dimethylformamide were stirred at 65° C. for 5 hours. Extraction with water/ethylacetate and chromatography on silicagel with ethylacetate/heptane (90/10 to 1/0) yielded 0.20 g (87%) 4-chloro-N-(2-oxo-azepan-3-yl)-N-(4-pyrazol-1-yl-benzyl)-benzenesulfonamide as light yellow solid, MS: m/e (%)=459.1 (MH$^+$, 100).

EXAMPLE 171

Rac-4-Chloro-N-(2-oxo-azepan-3-yl)-N-(4-[1,2,4]triazol-1-yl-benzyl)-benzenesulfonamide 4-Chloro-N-(2-oxo-azepan-3-yl)-benzenesulfonamide (0.16 g, 0.52 mmol), 1-[4-(bromomethyl)phenyl]-1H-1,2,4-triazol (0.25 g, 1.03 mmol), potassium carbonate (0.72 g, 5.17 mmol) and potassium iodide (0.02 g, 0.10 mmol) in 5 ml dimethylformamide were stirred at 65° C. for 5 hours. Extraction with water/ethylacetate and chromatography on silicagel with ethylacetate yielded 0.15 g (64%) 4-chloro-N-(2-oxo-azepan-3-yl)-N-(4-[1,2,4]triazol-1-yl-benzyl)-benzenesulfonamide as white solid, MS: m/e (%)=460.1 (MH$^+$, 100).

EXAMPLE 172

Rac-4-Chloro-N-(4-difluoromethyl-benzyl)-N-(2-oxo-azepan-3-yl)-benzenesulfonamide a) 1-Bromomethyl-4-difluoromethyl-benzene alpha-Bromo-p-tolualdehyde (1.00 g, 5.02 mmol) was suspended in 60 ml dichloromethane. Bis(2-methoxyethyl)aminosulfur trifluoride (5.9 ml, 30.5 mmol) and 58 µl (1.01 mmol) ethanol were added. The mixture was stirred at 40° C. for 8 hours. After evaporation of the solvent the residue was added drop-wise to cold saturated aqueous sodium bicarbonate solution. Extraction with ethylacetate, washing with saturated aqueous sodium bicarbonate and brine, drying with sodium sulfate and removal of the solvent by distillation yielded 0.81 g (73%) 1-bromomethyl-4-difluoromethyl-benzene, MS: m/e (%)=141.0 (M–Br, 100), 220/222 (M, 6).

b) 4-Chloro-N-(4-difluoromethyl-benzyl)-N-(2-oxo-azepan-3-yl)-benzenesulfonamide 4-Chloro-N-(2-oxo-azepan-3-yl)-benzenesulfonamide (0.45 g, 1.50 mmol), 1-bromomethyl-4-difluoromethyl-benzene (0.66 g, 3.00 mmol), potassium carbonate (2.09 g, 15.0 mmol) and potassium iodide (0.05 g, 0.20 mmol) in 15 ml dimethylformamide were stirred at 65° C. for 5 hours. Extraction with water/ethylacetate and chromatography on silicagel with ethylacetate/heptane (90/10 to 1/0) yielded 0.63 g (94%) 4-chloro-N-(4-difluoromethyl-benzyl)-N-(2-oxo-azepan-3-yl)-benzenesulfonamide as white solid, MS: m/e (%)=443.0 (MH$^+$, 100).

EXAMPLE 173

Rac-4-Chloro-N-(4-cyano-benzyl)-N-(2-oxo-azepan-3-yl)-benzenesulfonamide

4-Chloro-N-(2-oxo-azepan-3-yl)-benzenesulfonamide (1.21 g, 4.00 mmol), 4-(bromomethyl)-benzonitrile (0.79 g, 4.00 mmol), potassium carbonate (5.58 g, 40.0 mmol) and potassium iodide (0.13 g, 0.80 mmol) in 200 ml dimethylformamide were stirred at 65° C. for 16 hours. Extraction with water/ethylacetate and chromatography on silicagel with ethylacetate yielded 1.05 g (63%) 4-chloro-N-(4-cyano-benzyl)-N-(2-oxo-azepan-3-yl)-benzenesulfonamide as white solid, MS: m/e (%)=418.1 (MH+, 100).

EXAMPLE 174

Rac-4-Chloro-N-[4-(5-methoxymethyl-[1,2,4]oxadiazol-3-yl)-benzyl]-N-(2-oxo-azepan-3-yl)-benzenesulfonamide a) 4-{[(4-Chloro-benzenesulfonyl)-(2-oxo-azepan-3-yl)-amino]-methyl}-N-hydroxy-benzamidine 4-Chloro-N-(4-cyano-benzyl)-N-(2-oxo-azepan-3-yl)-benzenesulfonamide (2.09 g, 5.00 mmol), sodium bicarbonate (0.52 g, 6.15 mmol) and hydroxylamine hydrochloride (0.43 g, 6.15 mmol) in a mixture of 20 ml ethanol and 4 ml water were refluxed for 11 hours. The solvents were removed by distillation and the residue was recrystalized from water. The solid was then suspended in dichloromethane, refluxed, cooled to room temperature and filtered to yield 1.74 g (77%) 4-{[(4-chloro-benzenesulfonyl)-(2-oxo-azepan-3-yl)-amino]-methyl}-N-hydroxy-benzamidine as white solid, MS: m/e (%)=451.0 (MH+, 100).

b) 4-Chloro-N-[4-(5-methoxymethyl-[1,2,4]oxadiazol-3-yl)-benzyl]-N-(2-oxo-azepan-3-yl)-benzenesulfonamide To a solution of methoxyacetic acid (86 µl, 1.10 mmol) in 5 ml dimethylformamide were added 1,1'-carbonyl-diimidazole (0.18 g, 1.10 mmol). The mixture was stirred at room temperature for 10 minutes, heated to 40° C. for a few minutes and cooled to room temperature. 4-{[(4-Chloro-benzenesulfonyl)-(2-oxo-azepan-3-yl)-amino]-methyl}-N-hydroxy-benzamidine (0.45 g, 1.00 mmol) was added and the mixture was stirred at 100° C. for 5 hours and then poured into water. Filtration and chromatography on silicagel with ethylacetate/heptane (1/1 to 4/1) yielded 0.46 g (90%) 4-chloro-N-[4-(5-methoxymethyl-[1,2,4]oxadiazol-3-yl)-benzyl]-N-(2-oxo-azepan-3-yl)-benzenesulfonamide as white solid, MS: m/e (%)=505.0 (MH+, 100).

EXAMPLE 175

Rac-4-Chloro-N-[4-(5-methyl-[1,2,4]oxadiazol-3-yl)-benzyl]-N-(2-oxo-azepan-3-yl)-benzenesulfonamide To a solution of acetic acid (63 µl, 1.10 mmol) in 5 ml dimethylformamide were added 1,1'-carbonyl-diimidazole (0.18 g, 1.10 mmol). The mixture was stirred at room temperature for 10 minutes, heated to 40° C. for a few minutes and cooled to room temperature. 4-{[(4-Chloro-benzenesulfonyl)-(2-oxo-azepan-3-yl)-amino]-methyl}-N-hydroxy-benzamidine (0.45 g, 1.00 mmol) was added and the mixture was stirred at 100° C. for 5 hours and then poured into water. Filtration and chromatography on silicagel with ethylacetate/heptane (1/1 to 4/1) yielded 0.43 g (91%) 4-chloro-N-[4-(5-methyl-[1,2,4]oxadiazol-3-yl)-benzyl]-N-(2-oxo-azepan-3-yl)-benzenesulfonamide as white solid, MS: m/e (%)=474.9 (MH+, 100).

EXAMPLE 176

Rac-N-[4-(5-Benzyloxymethyl-[1,2,4]oxadiazol-3-yl)-benzyl]-4-chloro-N-(2-oxo-azepan-3-yl)-benzenesulfonamide To a solution of benzyloxyacetic acid (162 µl, 1.10 mmol) in 5 ml dimethylformamide were added 1,1'-carbonyl-diimidazole (0.18 g, 1.10 mmol). The mixture was stirred at room temperature for 10 minutes, heated to 40° C. for a few minutes and cooled to room temperature. 4-{[(4-Chloro-benzenesulfonyl)-(2-oxo-azepan-3-yl)-amino]-methyl}-N-hydroxy-benzamidine (0.45 g, 1.00 mmol) was added and the mixture was stirred at 100° C. for 5 hours and then poured into water. Filtration and chromatography on silicagel with ethylacetate/heptane (1/1 to 4/1) yielded 0.51 g (87%) N-[4-(5-benzyloxymethyl-[1,2,4]oxadiazol-3-yl)-benzyl]-4-chloro-N-(2-oxo-azepan-3-yl)-benzenesulfonamide as white solid, MS: m/e (%)=581.1 (MH+, 100).

EXAMPLE 177

4-Chloro-N-[4-(5-hydroxymethyl-[1,2,4]oxadiazol-3-yl)-benzyl]-N-(2-oxo-azepan-3-yl)-benzenesulfonamide a) Acetic acid 3-(4-{[(4-chloro-benzenesulfonyl)-(2-oxo-azepan-3-yl)-amino]-methyl}-phenyl)-[1,2,4]oxadiazol-5-ylmethyl ester To a solution of acetoxyacetic acid (0.13 g, 1.10 mmol) in 5 ml dimethylformamide were added 1,1'-carbonyl-diimidazole (0.18 g, 1.10 mmol). The mixture was stirred at room temperature for 10 minutes, heated to 40° C. for a few minutes and cooled to room temperature. 4-{[(4-Chloro-benzenesulfonyl)-(2-oxo-azepan-3-yl)-amino]-methyl}-N-hydroxy-benzamidine (0.45 g, 1.00 mmol) was added and the mixture was stirred at 100° C. for 5 hours and then poured into water. Filtration and chromatography on silicagel with ethylacetate/heptane (3/1) yielded 0.15 g (29%) acetic acid 3-(4-{[(4-chloro-benzenesulfonyl)-(2-oxo-azepan-3-yl)-amino]-methyl}-phenyl)-[1,2,4]oxadiazol-5-ylmethyl ester as white solid, MS: m/e (%)=533.0 (MH+, 100).

b) 4-Chloro-N-[4-(5-hydroxymethyl-[1,2,4]oxadiazol-3-yl)-benzyl]-N-(2-oxo-azepan-3-yl)-benzenesulfonamide A solution of 0.03 g (0.05 mmol) acetic acid 3-(4-{[(4-chloro-benzenesulfonyl)-(2-oxo-azepan-3-yl)-amino]-methyl}-phenyl)-[1,2,4]oxadiazol-5-ylmethyl ester in 1 ml tetrahydrofuran was stirred with 0.2 ml (0.2 mmol) 1 molar aqueous sodium hydroxide for 3 hours at room temperature. Water and aqueous hydrochloric acid was added to reach pH 1. Extraction with ethylacetate, drying with sodium sulfate, filtration and removal of the solvent by distillation yielded 0.02 g (98%) 4-chloro-N-[4-(5-hydroxymethyl-[1,2,4]oxadiazol-3-yl)-benzyl]-N-(2-oxo-azepan-3-yl)-benzenesulfonamide as white solid, MS: m/e (%)=491.0 (MH+, 100).

EXAMPLE 178

4-Chloro-N-(5-isopropyl-2-oxo-azepan-3-yl)-N-pyridin-4-ylmethyl-benzenesulfonamide The title compound, MS: m/e=436.0 (MH$^+$), was obtained in comparable yield analogous to the procedure described for Example 3, using 4-(hydroxymethyl)pyridine and 4-chloro-N-(5-isopropyl-2-oxo-azepan-3-yl)-benzenesulfonamide from Example 4e.

EXAMPLE 179

4-Chloro-N-[4-(3-fluoro-propoxy)-benzyl]-N-(5-isopropyl-2-oxo-azepan-3-yl)-benzenesulfonamide The title compound, MS: m/e=511.0 (MH$^+$), was obtained in comparable yield analogous to the procedure described for Example 3, using [4-(3-fluoropropoxy) phenyl]methanol and 4-chloro-N-(5-isopropyl-2-oxo-azepan-3-yl)-benzenesulfonamide from Example 4e.

EXAMPLE 180

4-Chloro-N-(5-isopropyl-2-oxo-azepan-3-yl)-N-[4-(5-methyl-[1,3,4]oxadiazol-2-yl)-benzyl]-benzenesulfonamide 4-{[(4-Chloro-benzenesulfonyl)-(5-isopropyl-2-oxo-azepan-3-yl)-amino]-methyl}-benzoic acid methyl ester (0.30 g, 0.60 mmol) was treated with hydrazine monohydrate (1.1 g, 22.4 mmol) in methanol (20 ml) for 48 h at r.t. The reaction mixture was concentrated under reduced pressure, diluted with water and extracted with $CH_2Cl_2$ (3×), The combined organic extracts were washed with water, dried ($MgSO_4$), filtered and concentrated under reduced pressure to yield a crude foam (0.29 g). 0.10 g of this crude hydrazide was dissolved in pyridine (1.4 ml) treated with ethylacetimidate hydrochloride (0.08 g, 0.66 mmol) under reflux for 1 h. The cooled reaction mixture was concentrated and extracted with ethyl acetate and washed with 1 N HCl (1×), $NaHCO_3$ sat.d (1×), brine, dried ($MgSO_4$) and filtered. The concentrated, crude product was purified using preparative RP($C_{18}$) chromatography: lyophilisate 25 mg; MS: m/e=517.4 (MH$^+$).

EXAMPLE 181

4-Chloro-N-(5-isopropyl-2-oxo-azepan-3-yl)-N-[4-(3-methyl-[1,2,4]oxadiazol-5-yl)-benzyl]-benzenesulfonamide 4-{[(4-Chloro-benzenesulfonyl)-(5-isopropyl-2-oxo-azepan-3-yl)-amino]-methyl}-benzoic acid methyl ester (0.30 g, 0.60 mmol) was saponified to the acid using LiOH.H$_2$O (0.04 g, 0.90 mmol). The acid (0.10 g, 0.21 mmol) was dissolved in THF (3 ml) and added dropwise to a solution of 1,1-carbonyl diimidazole (CDI, 0.04 g, 0.23 mmol) in THF (0.5 ml). After 30 min, N-hydroxy-acetamidine (0.04 g, 0.23 mmol) was added. A further two equivalents each of CDI and N-hydroxy-acetamidine were added during a further 48 h stirring at r.t. The reaction mixture was concentrated and crude, coupled amidine was purified over silica gel (gradient ethyl acetate to ethyl acetate/methanol 15%): white solid 0.09 g (73%); MS: m/e=535.5 (MH$^+$). Purified amidine (0.08 g, 0.15 mmol) cyclised in the presence of tetrabutylammonium fluoride (1 M, THF 5 ml) over 36 h at r.t. The reaction mixture was diluted with water and extracted with ethyl acetate (3×). The combined organice extracts were washed with water, brine, dried ($MgSO_4$), filtered and concentrated under reduced pressure. The concentrated, crude product was purified using preparative RP($C_{18}$) chromatography: lyophilisate 15 mg; MS: m/e=517.4 (MH$^+$).

EXAMPLE 182

3-(4-{[(4-Chloro-benzenesulfonyl)-(5-isopropyl-2-oxo-azepan-3-yl)-amino]-methyl}-phenyl)-propionic acid 3-(4-{[(4-Chloro-benzenesulfonyl)-(5-isopropyl-2-oxo-azepan-3-yl)-amino]-methyl}-phenyl)-propionic acid methyl ester was prepared according to alkylation protocol Example 2c using 3-(4-bromomethyl-phenyl)-propionic acid methyl ester (prepared analogous to lit. route: U.S. Pat. No. 4,032,533). The methyl ester (0.21 g, 0.40 mmol) was saponified using NaOH (0.2 g) in THF (4 ml) for 4 h. The reaction mixture was diluted with water and acidified (KHSO4/$K_2SO_4$) to pH 2-3, extracted with ethyl acetate (2×). The combined organice extracts were washed with water, brine, dried ($MgSO_4$), filtered and concentrated under reduced pressure. The crude was crystallised from ethyl acetate to yield 3-(4-{[(4-chloro-benzenesulfonyl)-(5-isopropyl-2-oxo-azepan-3-yl)-amino]-methyl}-phenyl)-propionic acid: 0.04 g; MS: m/e=505.1 (MH$^+$).

EXAMPLE 183

4-{[(4-Chloro-benzenesulfonyl)-((R)-5,5-dimethyl-2-oxo-azepan-3-yl)-amino]-methyl}-N-cyclopropyl-benzamide 4-Chloro-N-((R)-5,5-dimethyl-2-oxo-azepan-3-yl)-benzenesulfonamide was obtained following chiral preparative chromatography [Chiralpak AD; isocratic 20% isopropanol/heptane] of racemic 4-chloro-N-(5,5-dimethyl-2-oxo-azepan-3-yl)-benzenesulfonamide intermediate prepared according to Example 4e starting with 4,4-dimethyl cyclohexanone and then alkylated as previously described for Example 2c to give 4-{[(4-chloro-benzenesulfonyl)-((R)-5,5-dimethyl-2-oxo-azepan-3-yl)-amino]-methyl}-N-cyclopropyl-benzamide MS: m/e=504.3 (MH$^+$).

EXAMPLE 184

4-{[(4-Chloro-benzenesulfonyl)-((S)-5,5-dimethyl-2-oxo-azepan-3-yl)-amino]-methyl}-N-cyclopropyl-benzamide 4-Chloro-N-((S)-5,5-dimethyl-2-oxo-azepan-3-yl)-benzenesulfonamide was obtained following chiral preparative chromatography [Chiralpak AD; isocratic 20% isopropanol/heptane] of racemic 4-chloro-N-(5,5-dimethyl-2-oxo-azepan-3-yl)-benzenesulfonamide intermediate prepared according to Example 4e starting with 4,4-dimethyl cyclohexanone and then alkylated as previously described for Example 2c to give 4-{[(4-chloro-benzenesulfonyl)-((S)-5,5-dimethyl-2-oxo-azepan-3-yl)-amino]-methyl}-N-cyclopropyl-benzamide MS: m/e=504.3 (MH$^+$).

EXAMPLE 185

4-{[(4-Chloro-benzenesulfonyl)-((R)-5,5-dimethyl-2-oxo-azepan-3-yl)-amino]-methyl}-3-fluoro-benzoic acid methyl ester 4-Bromomethyl-3-fluoro-benzoic acid methyl ester
3-Fluoromethyl benzoic acid methyl ester (4.2 g, 25 mmol), N-bromosuccinimide (4.90 g, 27.50 mmol) and dibenzoyl peroxide (0.18 g, 0.75 mmol) were dissolved in CCl$_4$ (100 ml) and the mixture was irradiated with a 150 W lamp and refluxed under an argon atmosphere for 5 h. The reaction mixture was allowed to cool to r.t. and then filtered. The concentrated filtrate was purified over silica gel (isopropyl ether/n-heptane 1:10 v/v): colourless oil 4.6 g (75%); MS: m/e=248.0 (M), 167.1 (M−Br, 100%).

4-{[(4-Chloro-benzenesulfonyl)-((R)-5,5-dimethyl-2-oxo-azepan-3-yl)-amino]-methyl}-3-fluoro-benzoic acid methyl ester
4-Chloro-N-((R)-5,5-dimethyl-2-oxo-azepan-3-yl)-benzenesulfonamide was alkylated using 4-bromomethyl-3-fluoro-benzoic acid methyl ester analogous to Example 2c to yield 4-{[(4-chloro-benzenesulfonyl)-((R)-5,5-dimethyl-2-oxo-azepan-3-yl)-amino]-methyl}-3-fluoro-benzoic acid methyl ester: MS: m/e=497.4 (MH$^+$).

EXAMPLE 186

3-(4-{[(4-Chloro-benzenesulfonyl)-((R)-5,5-dimethyl-2-oxo-azepan-3-yl)-amino]-methyl}-phenyl)-propionic acid methyl ester 4-Chloro-N-((R)-5,5-dimethyl-2-oxo-azepan-3-yl)-benzenesulfonamide was alkylated using 3-(4-bromomethyl-phenyl)-propionic acid methyl ester analogous to Example 2c to yield 3-(4-{[(4-chloro-benzenesulfonyl)-((R)-5,5-dimethyl-2-oxo-azepan-3-yl)-amino]-methyl}-phenyl)-propionic acid methyl ester: MS: m/e=507.6 (MH$^+$).

EXAMPLE 187

3-(4-{[(4-Chloro-benzenesulfonyl)-((R)-5,5-dimethyl-2-oxo-azepan-3-yl)-amino]-methyl}-phenyl)-propionic acid 3-(4-{[(4-Chloro-benzenesulfonyl)-((R)-5,5-dimethyl-2-oxo-azepan-3-yl)-amino]-methyl}-phenyl)-propionic acid methyl ester (0.06 g, 0.11 mmol) was dissolved in methanol (4 ml) and treated with 1 N NaOH (0.2 ml) overnight. The mixture was diluted with water and the methanol removed under reduced pressure. The residue was acidified (KHSO$_4$/K$_2$SO$_4$) and extracted with ethyl acetate (3×). The combined extracts were concentrated and the crude residue was purified using preparative RP(C$_{18}$) chromatography: lyophilisate 15 mg; MS: m/e=491.1 (MH$^+$).

EXAMPLE 188

4-{[(4-Chloro-benzenesulfonyl)-((R)-5,5-dimethyl-2-oxo-azepan-3-yl)-amino]-methyl}-3-fluoro-benzoic acid 4-{[(4-Chloro-benzenesulfonyl)-((R)-5,5-dimethyl-2-oxo-azepan-3-yl)-amino]-methyl}-3-fluoro-benzoic acid methyl ester (0.52 g, 1.1 mmol) was dissolved in THF (20 ml) and treated with 1 N NaOH (2.1 ml) for 2 h. Work-up as for Example 187 yielded crude which was crystallised from acetonitrile to give 4-{[(4-chloro-benzenesulfonyl)-((R)-5,5-dimethyl-2-oxo-azepan-3-yl)-amino]-methyl}-3-fluoro-benzoic acid: 0.38 g; MS: m/e=481.1 (MH$^+$).

EXAMPLE 189

4-Chloro-N-[4-(N',N'-dimethyl-hydrazinocarbonyl)-2-fluoro-benzyl]-N-((R)-5,5-dimethyl-2-oxo-azepan-3-yl)-benzenesulfonamide 4-{[(4-Chloro-benzenesulfonyl)-((R)-5,5-dimethyl-2-oxo-azepan-3-yl)-amino]-methyl}-3-fluoro-benzoic acid (0.15 g, 0.30 mmol) was dissolved in DMF (20 ml) and treated with 2-(2-pyridon-1-yl)-1,1,3,3-tetramethyluronium tetrafluoroborate (TPTU) (0.1 g, 0.33 mmol), Hünig's base (0.15 ml, 0.90 mmol) and N,N-dimethyl hydrazine (0.07 ml, 0.90 mmol). After 1 h the reaction mixture was concentrated under reduced pressure and the residue was dissolved in ethyl acetate and washed with NaHCO$_3$, KHSO$_4$/K$_2$SO$_4$, brine, dried (Na$_2$SO$_4$) filtered anconcentrated under reduced pressure. Crystallisation from isopropyl acetate yielded 4-chloro-N-[4-(N',N'-dimethyl-hydrazinocarbonyl)-2-fluoro-benzyl]-N-((R)-5,5-dimethyl-2-oxo-azepan-3-yl)-benzenesulfonamide as a crystalline solid: δ 0.12 g; MS: m/e=525.4 (MH$^+$).

EXAMPLE 190

3-(2-{[(4-Chloro-benzenesulfonyl)-((R)-5,5-dimethyl-2-oxo-azepan-3-yl)-amino]-methyl}-5-fluoro-phenyl)-propionic acid HBr gas was passed through a suspension of 3-(3-fluorophenyl)propionic acid (5.1 g, 30 mmol), paraformaldehyde (1.2 g) in aqueous HBr (48%, 20 ml). After 3.5 h at 55° C. the suspension was extracted with ethyl acetate (3×) and the combined orgaic extracts were washed with brine, dried (Na$_2$SO$_4$) filtered and evaporated. The crude was recrystallized from CCl$_4$-n-hexane to yield crystalline 3-(2-bromomethyl-5-fluoro-phenyl)-propionic acid: 2.7 g; MS: m/e=260 (M), 181 (M−Br).

The acid (2.6 g, 10 mmol) was added to a mixture of sulfuric acid (0.60 ml, 11 mmol) in methanol (30 ml). After 1 h at r.t. the reaction mixture was diluted with watere and solvent was removed under reduced pressure. The residue was dissolved in ethyl acetate and washed with NaHCO$_3$, brine, dried (Na$_2$SO$_4$) filtered and concentrated under reduced pressure to yield 3-(2-bromomethyl-5-fluoro-phenyl)-propionic acid methyl ester as a colourless oil:: 2.6 g; MS: m/e=276 (M), 195 (M−Br).

4-Chloro-N-((R)-5,5-dimethyl-2-oxo-azepan-3-yl)-benzenesulfonamide was alkylated using 3-(2-bromomethyl-5-fluoro-phenyl)-propionic acid methyl ester analogous to Example 2c and then saponified to give 3-(2-{[(4-chloro-benzenesulfonyl)-((R)-5,5-dimethyl-2-oxo-azepan-3-yl)-amino]-methyl}-5-fluoro-phenyl)-propionic acid. MS: m/e=509.3 (MH$^−$).

EXAMPLE 191

4-Chloro-N-((R)-5,5-dimethyl-2-oxo-azepan-3-yl)-N-(4-isoxazol-5-yl-benzyl)-benzenesulfonamide 4-Chloro-N-((R)-5,5-dimethyl-2-oxo-azepan-3-yl)-benzenesulfonamide was alkylated using 5-(4-bromomethyl-phenyl)-isoxazole analogous to Example 2c to afford 4-chloro-N-((R)-5,5-dimethyl-2-oxo-azepan-3-yl)-N-(4-isoxazol-5-yl-benzyl)-benzenesulfonamide MS: m/e=488.1 (MH⁺).

EXAMPLE 192

4-Chloro-N-((R)-5,5-dimethyl-2-oxo-azepan-3-yl)-N-(2-fluoro-4-methoxy-benzyl)-benzenesulfonamide The title compound, MS: m/e=469.4 (MH⁺), was obtained in comparable yield analogous to the procedure described for Example 3, using (2-fluoro-4-methoxy-phenyl)-methanol and 4-chloro-N-((R)-5,5-dimethyl-2-oxo-azepan-3-yl)-benzenesulfonamide from Example 4e.

EXAMPLE 193

4-Chloro-N-((R)-5,5-dimethyl-2-oxo-azepan-3-yl)-N-(2-fluoro-4-hydroxymethyl-benzyl)-benzenesulfonamide 4-{[(4-Chloro-benzenesulfonyl)-((R)-5,5-dimethyl-2-oxo-azepan-3-yl)-amino]-methyl}-3-fluoro-benzoic acid (0.05 g, 0.10 mmol) was dissolved in THF (2 ml) and added dropwise to a suspension of LiAlH$_4$ (0.04 g, 1 mmol) in THF (2 ml). After 6 h to the reaction mixture was added water (0.5 ml), 1 N NaOH (0.2 ml) and after 15 min of vigorous stirring it was filtered. The filtrate was concentrated under reduced pressure and purified using preparative RP(C$_{18}$) chromatography: lyophilisate 5 mg; MS: m/e=469.1 (MH⁺).

EXAMPLE 194

3-(4-{[(4-Chloro-benzenesulfonyl)-(2-oxo-5-trifluoromethyl-azepan-3-yl)-amino]-methyl}-phenyl)-propionic acid The title compound, MS: m/e=531.1 (MH⁻), was obtained in comparable yield analogous to the procedure described for Example 182 using 4-chloro-N-(5-trifluoromethyl-2-oxo-azepan-3-yl)-benzenesulfonamide and 3-(4-bromomethyl-phenyl)-propionic acid methyl ester in the alkylation step.

EXAMPLE 195

4-{[(4-Chloro-benzenesulfonyl)-(2-oxo-5-trifluoromethyl-azepan-3-yl)-amino]-methyl}-benzoic acid The title compound, MS: m/e=505.1 (MH⁺), was obtained in comparable yield analogous to the procedure described for Example 182 using 4-chloro-N-(5-trifluoromethyl-2-oxo-azepan-3-yl)-benzenesulfonamide and 4-bromomethyl-benzoic acid methyl ester in the alkylation step.

EXAMPLE 196

4-Chloro-N-[4-(N',N'-dimethyl-hydrazinocarbonyl)-benzyl]-N-(2-oxo-5-trifluoromethyl-azepan-3-yl)-benzenesulfonamide The title compound, MS: m/e=547.2 (MH⁺), was obtained in comparable yield analogous to the procedure described for Example 189 using 4-{[(4-chloro-benzenesulfonyl)-(2-oxo-5-trifluoromethyl-azepan-3-yl)-amino]-methyl}-benzoic acid as the precursor to hydrazide formation.

EXAMPLE 197

4-{[(4-Chloro-benzenesulfonyl)-(2-oxo-5-trifluoromethyl-azepan-3-yl)-amino]-methyl}-3-fluoro-benzoic acid methyl ester The title compound, MS: m/e=537.5 (MH⁺), was obtained in comparable yield analogous to the procedure described for Example 185 using 4-chloro-N-(5-trifluoromethyl-2-oxo-azepan-3-yl)-benzenesulfonamide and 4-bromomethyl-3-fluoro-benzoic acid methyl ester in the alkylation step.

EXAMPLE 198

4-Chloro-N-(2-fluoro-4-methoxy-benzyl)-N-(2-oxo-5-trifluoromethyl-azepan-3-yl)-benzenesulfonamide The title compound, MS: m/e=509.2 (MH⁺), was obtained in comparable yield analogous to the procedure described for Example 3 using 4-chloro-N-(5-trifluoromethyl-2-oxo-azepan-3-yl)-benzenesulfonamide and (2-fluoro-4-methoxy-phenyl)-methanol in the Mitsunobu reaction.

EXAMPLE 199

4-{[(4-Chloro-benzenesulfonyl)-(2-oxo-5-trifluoromethyl-azepan-3-yl)-amino]-methyl}-3-fluoro-benzoic acid 4-{[(4-Chloro-benzenesulfonyl)-(2-oxo-5-trifluoromethyl-azepan-3-yl)-amino]-methyl}-3-fluoro-benzoic acid methyl ester (0.03 g, 0.06 mmol) was dissolved in THF (2 ml) and 1 N NaOH (4 ml) was added. The reaction mixture was stirred for 6 h at pH 10. A KHSO$_4$/K$_2$SO$_4$ aqueous buffer was added to adjust the pH to 3. The mixture was extracted with ethyl acetate and the combined organic extracts were dried (Na$_2$SO$_4$) and concentrated under reduced pressure and lyophilised yielding a solid: 11 mg; MS: m/e=521.2 (MH⁻).

EXAMPLE 200

4-Chloro-N-(2-fluoro-4-hydroxymethyl-benzyl)-N-(2-oxo-5-trifluoromethyl-azepan-3-yl)-benzenesulfonamide 4-{[(4-Chloro-benzenesulfonyl)-(2-oxo-5-trifluoromethyl-azepan-3-yl)-amino]-methyl}-3-fluoro-benzoic acid methyl ester (0.05 g, 0.09 mmol) in THF (1 ml) was added dropwise to a cooled (ice-bath) suspension of LiAlH$_4$ (0.02 g, 0.44 mmol) in THF (1 ml) under an argon atmosphere. The cold bath was removed and the reaction mixture was further stirred for 3.5 h. Ethyl acetate and a KHSO$_4$/K$_2$SO$_4$ buffer was added to the reaction mixture. The organic fraction was further washed with a KHSO$_4$/K$_2$SO$_4$ (2×), water, brine, dried (Na$_2$$_{SO4}$), filtered, concentrated under reduced pressure and purified using preparative RP(C$_{18}$) chromatography to give 4-chloro-N-(2-fluoro-4-hydroxymethyl-benzyl)-N-(2-oxo-5-trifluoromethyl-azepan-3-yl)-benzenesulfonamide as a lyophilisate: 13 mg; MS: m/e=509.4 (MH⁺).

EXAMPLE 201

3-(4-{[(4-Chloro-benzenesulfonyl)-((R)-2-oxo-azepan-3-yl)-amino]-methyl}-phenyl)-propionic acid The title compound, MS: m/e=465.3 (MH$^+$), was obtained in comparable yield analogous to the procedure described for Example 187 from its corresponding methyl ester.

EXAMPLE 202

4-(4-{[(4-Chloro-benzenesulfonyl)-((R)-2-oxo-azepan-3-yl)-amino]-methyl}-phenyl)-butyric acid methyl ester The title compound, MS: m/e=510.6 (MNH$_4^+$), was obtained in comparable yield analogous to the procedure described for Example 2c, using 4-(4-bromomethyl-phenyl)-butyric acid methyl ester as the benzylating reagent.

EXAMPLE 203 rac-4-{[(4-Chloro-benzenesulfonyl)-(2-oxo-azepan-3-yl)-amino]-methyl}-3-fluoro-benzoic acid methyl ester The title compound, MS: m/e=469.4 (MH$^+$), was obtained in comparable yield analogous to the procedure described for Example 2c, using 4-bromomethyl-3-fluoro-benzoic acid methyl ester as the benzylating reagent and the achiral sulfonamide.

EXAMPLE 204

4-(4-{[(4-Chloro-benzenesulfonyl)-((R)-2-oxo-azepan-3-yl)-amino]-methyl}-phenyl)-butyric acid The title compound, MS: m/e=496.4 (MNH4$^+$), was obtained in comparable yield from 4-(4-{[(4-chloro-benzenesulfonyl)-((R)-2-oxo-azepan-3-yl)-amino]-methyl}-phenyl)-butyric acid methyl ester analogous to the procedure described for Example 182.

EXAMPLE 205

(4-{[(4-Chloro-benzenesulfonyl)-((R)-2-oxo-azepan-3-yl)-amino]-methyl}-phenyl)-acetic acid The title compound, MS: m/e=449.1 (MH$^-$), was obtained in comparable yield from (4-{[(4-chloro-benzenesulfonyl)-((R)-2-oxo-azepan-3-yl)-amino]-methyl}-phenyl)-acetic acid methyl ester analogous to the procedure described for Example 182.

EXAMPLE 206

4-Chloro-N-(4-oxazol-5-yl-benzyl)-N-((R)-2-oxo-azepan-3-yl)-benzenesulfonamide

The title compound, MS: m/e=460.1 (MH$^+$), was obtained in comparable yield analogous to the procedure described for Example 2c, using 5-(4-bromomethyl-phenyl)-oxazole as the benzylating reagent.

EXAMPLE 207

N-[2-(4-1{[(4-Chloro-benzenesulfonyl)-((R)-2-oxo-azepan-3-yl)-amino]-methyl}-phenyl)-ethyl]-acetamide The title compound, MS: m/e=478.0 (MH$^+$), was obtained in comparable yield analogous to the procedure described for Example 2c, using N-[2-(4-chloromethyl-phenyl)-ethyl]-acetamide as the benzylating reagent.

EXAMPLE 208

4-Chloro-N-(4-isoxazol-5-yl-benzyl)-N-((R)-2-oxo-azepan-3-yl)-benzenesulfonamide The title compound, MS: m/e=460.1 (MH$^+$), was obtained in comparable yield analogous to the procedure described for Example 2c, using 5-(4-bromomethyl-phenyl)-isoxazole as the benzylating reagent.

EXAMPLE 209

4-Chloro-N-(4-hydroxymethyl-benzyl)-N-((R)-2-oxo-azepan-3-yl)-benzenesulfonamide The title compound, MS: m/e=423.0 (MH$^+$), 440.3 (MNH$_4^+$), was obtained in comparable yield analogous to the procedure described for Example 193.

EXAMPLE 210

4-Chloro-N-(2,5-difluoro-4-methoxy-benzyl)-N-((R)-2-oxo-azepan-3-yl)-benzenesulfonamide The title compound, MS: m/e=459.1 (MH$^+$), was obtained in comparable yield analogous to the procedure described for Example 2c, using 1-bromomethyl-2,5-difluoro-4-methoxy-benzene as the benzylating reagent.

EXAMPLE 211

4-Chloro-N-(2,3-difluoro-4-methoxy-benzyl)-N-((R)-2-oxo-azepan-3-yl)-benzenesulfonamide The title compound, MS: m/e=459.0 (MH$^+$), 479.0 (MNH$_4^+$) was obtained in comparable yield analogous to the procedure described for Example 2c, using 1-bromomethyl-2,3-difluoro-4-methoxy-benzene which was previously prepared from 2,3-difluoro-4-methylanisole analogous to the bromination protocol described in Example 185.

EXAMPLE 212

3-(4-{[(4-Chloro-benzenesulfonyl)-((R)-2-oxo-azepan-3-yl)-amino]-methyl}-phenyl)-3-methyl-butyric acid methyl ester The title compound, MS: m/e=507.3 (MH$^+$), 524.2 (MNH$_4^+$) was obtained in comparable yield analogous to the procedure described for Example 2c, using 3-(4-bromomethyl-phenyl)-3-methyl-butyric acid methyl ester which was previously prepared from 3-methyl-3-phenyl-butyric acid analogous to the bromomethylation and esterifaction sequence described in Example 190 and from the literature (U.S. Pat. No. 4,032,533).

EXAMPLE 213

3-(4-{[(4-Chloro-benzenesulfonyl)-((R)-2-oxo-azepan-3-yl)-amino]-methyl}-phenyl)-2,2-dimethyl-propionic acid methyl ester The title compound, MS: m/e=507.2 (MH$^+$), 524.1 (MNH$_4^+$) was obtained in comparable yield analogous to the procedure described for Example 2c, using 3-(4-bromomethyl-phenyl)-2,2-dimethyl-propionic acid methyl ester which was previously prepared from 2,2-dimethyl-3-phenyl-propionic acid analogous to the bromomethylation and esterifaction sequence described in Example 190 and from the literature (U.S. Pat. No. 4,032,533).

EXAMPLE 214

3-(3-Chloro-4-{[(4-chloro-benzenesulfonyl)-((R)-2-oxo-azepan-3-yl)-amino]-methyl}-phenyl)-propionic acid methyl ester The title compound, MS: m/e=513.1 (MH$^+$), 530.1 (MNH$_4^+$) was obtained in comparable yield analogous to the procedure described for Example 2c, using 3-(4-bromomethyl-3-chloro-phenyl)-propionic acid methyl ester which was previously prepared from 3-(3-chloro-phenyl)-propionic acid analogous to the bromomethylation and esterifaction sequence described in Example 190 and from the literature (U.S. Pat. No. 4,032,533).

EXAMPLE 215

5-{[(4-Chloro-benzenesulfonyl)-((R)-2-oxo-azepan-3-yl)-amino]-methyl}-benzofuran-2-carboxylic acid ethyl ester The title compound, MS: m/e=505.2 (MH$^+$), 522.2 (MNH$_4^+$) was obtained in comparable yield analogous to the procedure described for Example 2c, using 5-chloromethyl-benzofuran-2-carboxylic acid ethyl ester.

EXAMPLE 216 rac-4-{[(4-Chloro-benzenesulfonyl)-(2-oxo-azepan-3-yl)-amino]-methyl}-3-fluoro-benzoic acid The title compound, MS: m/e=453.2 (MH$^-$), 522.2 (MOAc$^-$) was obtained in comparable yield by saponification of rac-4-{[(4-chloro-benzenesulfonyl)-(2-oxo-azepan-3-yl)-amino]-methyl}-3-fluoro-benzoic acid methyl ester analogous to the procedure described for Example 199.

EXAMPLE 217

4-{[(4-Chloro-benzenesulfonyl)-((R)-2-oxo-azepan-3-yl)-amino]-methyl}-3-fluoro-benzoic acid The title compound, MS: m/e=453.1 (MH$^-$), 513.1 (MOAc$^-$) was obtained in comparable yield by saponification of 4-{[(4-chloro-benzenesulfonyl)-((R)-2-oxo-azepan-3-yl)-amino]-methyl}-3-fluoro-benzoic acid methyl ester analogous to the procedure described for Example 199.

EXAMPLE 218

3-(4-{[(4-Chloro-benzenesulfonyl)-((R)-2-oxo-azepan-3-yl)-amino]-methyl}-phenyl)-3-methyl-butyric acid The title compound, MS: m/e=491.1 (MH$^-$), 551.1 (MOAc$^-$) was obtained in comparable yield by saponification 3-(4-{[(4-chloro-benzenesulfonyl)-((R)-2-oxo-azepan-3-yl)-amino]-methyl}-phenyl)-3-methyl-butyric acid methyl ester analogous to the procedure described for Example 199.

EXAMPLE 219

3-(4-{[(4-Chloro-benzenesulfonyl)-((R)-2-oxo-azepan-3-yl)-amino]-methyl}-phenyl)-2,2-dimethyl-propionic acid The title compound, MS: m/e=491.0 (MH$^-$), 551.0 (MOAc$^-$) was obtained in comparable yield by saponification 3-(4-{[(4-chloro-benzenesulfonyl)-((R)-2-oxo-azepan-3-yl)-amino]-methyl}-phenyl)-2,2-dimethyl-propionic acid methyl ester analogous to the procedure described for Example 199.

EXAMPLE 220

3-(3-Chloro-4-{[(4-chloro-benzenesulfonyl)-((R)-2-oxo-azepan-3-yl)-amino]-methyl}-phenyl)-propionic acid The title compound, MS: m/e=497.0 (MH$^-$), 557.0 (MOAc$^-$) was obtained in comparable yield by saponification 3-(3-chloro-4-{[(4-chloro-benzenesulfonyl)-((R)-2-oxo-azepan-3-yl)-amino]-methyl}-phenyl)-propionic acid methyl ester analogous to the procedure described for Example 199.

EXAMPLE 221 rac-4-{[(4-Chloro-benzenesulfonyl)-(4,4-dimethyl-2-oxo-azepan-3-yl)-amino]-methyl}-N-cyclopropyl-benzamide a) {1-[Allyl-(2,4-dimethoxy-benzyl)-carbamoyl]-2,2-dimethyl-but-3-enyl}-carbamic acid tert-butyl ester 2-[[(1,1-Dimethylethoxy)carbonyl]amino]-3,3-dimethyl-4-pentenoic acid (322 mg, 1.32 mmol; Synthesis see Bartlett, Paul A.; Barstow, James F. Journal of Organic Chemistry (1982), 47(20), 3933-41) was dissolved in dimethylformamide (6 ml) and activated with the coupling reagent TATU (469 mg, 1.46 mmol) and Hünig's base (376 mg, 2.91 mmol) for 2 min. Allyl-(2,4-dimethoxy-benzyl)-amine (274 mg, 1.32 mmol) dissolved in dimethylformamide (2 ml) was added and the mixture was stirred overnight. The solvent was evaporated and the residue was dissolved in ethyl acetate, washed with saturated NaHCO$_3$ solution, 1 M KHSO4 solution and brine. After drying with magnesiumsulfate the organic layer was concentrated and purified by flash chromatography (heptane/ethyl acetate=2:1) to yield 510 mg (89%) of {1-[allyl-(2,4-dimethoxy-benzyl)-carbamoyl]-2,2-dimethyl-but-3-enyl}-carbamic acid tert-butyl ester; MS: m/e=433.6 (MH$^+$), 450.6 (M+NH$_4^+$).

b) [1-(2,4-Dimethoxy-benzyl)-4,4-dimethyl-2-oxo-2,3,4,7-tetrahydro-1H-azepin-3-yl]-carbamic acid tert-butyl ester {1-[Allyl-(2,4-dimethoxy-benzyl)-carbamoyl]-2,2-dimethyl-but-3-enyl}-carbamic acid tert-butyl ester (0.5 g, 1.16 mmol) was dissolved in dichloromethane (400 ml), bis (tricyclohexylphosphine)benzylidine ruthenium dichloride (145 mg, 0.17 mmol) was added and the purple solution was refluxed for 48 hours. The solvent was evaporated, the residue was dissolved in ethyl acetate and washed with NaHCO$_3$ solution, 1M KHSO$_4$ solution and brine. After drying with magnesiumsulfate the organic layer was concentrated and purified by flash chromatography (heptane/ethyl acetate=4:1) to yield 295 mg (63%) of [1-(2,4-dimethoxy-benzyl)-4,4-dimethyl-2-oxo-2,3,4,7-tetrahydro-1H-azepin-3-yl]-carbamic acid tert-butyl ester; MS: m/e=405.5 (MH$^+$).

c) [1-(2,4-Dimethoxy-benzyl)-4,4-dimethyl-2-oxo-azepan-3-yl]-carbamic acid tert-butyl ester

[1-(2,4-Dimethoxy-benzyl)-4,4-dimethyl-2-oxo-2,3,4,7-tetrahydro-1H-azepin-3-yl]-carbamic acid tert-butyl ester (260 mg, 0.64 mmol) was dissolved in methanol (10 ml). Palladium on charcoal (30 mg, 10%) was added and the mixture was hydrogenated at room temperature for 90 minutes. The catalyst was filtered off and the filtrate was evaporated. The residue was purified by flash chromatography (heptane/ethyl acetate=1:1) to yield 220 mg (84%) of [1-(2,4-dimethoxy-benzyl)-4,4-dimethyl-2-oxo-azepan-3-yl]-carbamic acid tert-butyl ester as a colourless oil; MS: m/e=407.4 (MH$^+$).

d) 4-({(4-Chloro-benzenesulfonyl)-[1-(2,4-dimethoxy-benzyl)-4,4-dimethyl-2-oxo-azepan-3-yl]-amino}-methyl)-N-cyclopropyl-benzamide For Boc-deprotection [1-(2,4-dimethoxy-benzyl)-4,4-dimethyl-2-oxo-azepan-3-yl]-carbamic acid tert-butyl ester (210 mg, 0.52 mmol) was dissolved in dichloromethane (2 ml) and trifluoroacetic acid (0.5 ml) was added dropwise. After stirring for 90 minutes the solvent and excess trifluoroacetic acid was evaporated and the residue was dried under high vacuum. Then it was dissolved in tetrahydrofurane (3 ml), 4-chlorobenzenesulfonyl chloride (121 mg, 0.57 mmol) and Hünig's base (202 mg, 1.56 mmol) was added and the mixture was stirred overnight. The mixture was diluted with dichloromethane and washed with 0.1N hydrochloric acid and water. The organic layer was dried over magnesium sulfate and evaporated. Flash chromatography (heptane/ethyl acetate=2:1) yielded 150 mg (60%) sulfonamide that was then dissolved in dimethylformamide (5 ml) for the alkylation step. To this solution 4-chloromethyl-N-cyclopropyl-benzamide (157 mg, 0.75 mmol), potassium carbonate (862 mg, 6.24 mmol) and potassium iodide (10 mg) were added and the mixture was stirred for 48 hours at 80° C. The solvent was evaporated and the residue was distributed between ethyl acetate and water. The organic layer was dried over magnesium sulfate and evaporated. Flash chromatography (heptane/ethyl acetate gradient) yielded 99 mg (48%) of the title compound as a foam; MS: m/e=654.4 (MH$^+$), 671.3 (M+NH$_4^+$).

e) 4-{[(4-Chloro-benzenesulfonyl)-(4,4-dimethyl-2-oxo-azepan-3-yl)-amino]-methyl}-N-cyclopropyl-benzamide 4-({(4-Chloro-benzenesulfonyl)-[1-(2,4-dimethoxy-benzyl)-4,4-dimethyl-2-oxo-azepan-3-yl]-amino}-methyl)-N-cyclopropyl-benzamide (95 mg) was dissolved in a mixture of trifluoroacetic acid/trifluoromethanesulfonic acid/dichloromethane=40:1:59 (2 ml) and stirred at room temperature for 15 minutes. After evaporation flash chromatography (heptane/ethyl acetate gradient) yielded 65 mg (90%) of 4-{[(4-chloro-benzenesulfonyl)-(4,4-dimethyl-2-oxo-azepan-3-yl)-amino]-methyl}-N-cyclopropyl-benzamide as a foam; MS: m/e=504.2 (MH$^+$), 521.3 (M+NH$_4^+$).

EXAMPLE 222 rac-4-Chloro-N-cyclopropylmethyl-N-(2-oxo-azepan-3-yl)-benzenesulfonamide

The title compound, MS: m/e=357.2 (MH$^+$), 379.3 (MNa$^+$), was obtained in comparable yield according to the procedure described for Example 2c, using bromomethyl-cyclopropane as the alkylating reagent.

EXAMPLE 223 rac-4-Chloro-N-cyclobutylmethyl-N-(2-oxo-azepan-3-yl)-benzenesulfonamide

The title compound, MS: m/e=371.2 (MH$^+$), was obtained in comparable yield according to the procedure described for Example 2c, using bromomethyl-cyclobutane as the alkylating reagent.

What is claimed is:
1. A compound of formula I

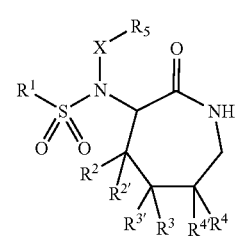

wherein
R$^1$ is aryl or is heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, each of which is unsubstituted or substituted by one or more substituents selected from the group consisting of
halogen,
lower alkyl,
lower alkyl substituted by halogen,
—O-lower alkyl substituted by halogen,
NO$_2$ and
CN;
R$^2$, R$^3$, R$^4$, R$^{2'}$, R$^{3'}$, and R$^{4'}$ are each independently lower alkyl, phenyl or lower alkyl substituted by halogen;
R$^5$ is aryl or is heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, each of which is unsubstituted or substituted by one or more substituents selected from the group consisting of
halogen,
lower alkyl,
lower alkoxy,
CN, nitro,
amino,
hydroxy,
lower alkyl substituted by hydroxy, and
lower alkyl substituted by halogen,
or is aryl or is heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, each of which is substituted by
—C(O)—NR''$_2$,
—(CR$_2$)$_m$—C(O)—R',
—(CH$_2$)$_m$-heterocycloalkyl wherein heterocycloalkyl is selected from the group consisting of oxetanyl, tetrahydrofuranyl, tetrahydropyranyl, azetidinyl, pyrrolidinyl, piperidinyl, piperazinyl, morpholinyl and thiomorpholinyl;
—(CH$_2$)$_m$-heteroaryl wherein heteroaryl is selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl which is unsubstituted or substituted by —(CH$_2$)$_m$-lower alkoxy, lower alkyl, —(CH$_2$)$_m$—O-benzyl or CH$_2$OH,
—O—C(O)-lower alkyl,
—O—C(O)—NR$_2$,
—O—(CH$_2$)$_m$—C(O)OH,
—O-lower alkinyl,
—O-lower alkyl substituted by halogen,
—O—(CH$_2$)$_m$-heterocyclyl,
—O—(CH$_2$)$_m$-phenyl which is unsubstituted or substituted by hydroxy,
—O—(CH$_2$)$_m$-heteroaryl wherein heteroaryl is selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl which is unsubstituted or substituted by lower alkyl,
—(CH$_2$)$_m$—NH—C(O)R',
—(CH$_2$)$_m$—NH—S(O)$_2$—R',
—S(O)$_2$-lower alkyl,
—S(O)$_2$-heterocyclyl, or
—S(O)$_2$NH-cycloalkyl,
or is cycloalkyl;
R' is hydrogen,
lower alkyl,
lower alkinyloxy,
hydroxy,
cycloalkyl, heterocycloalkyl selected from the group consisting of oxetanyl, tetrahydrofuranyl, tetrahydropyranyl, azetidinyl, pyrrolidinyl, piperidinyl, piperazinyl, morpholinyl and thiomorpholinyl, which is unsubstituted or substituted by one or more substituents selected from
COOH,
—C(O)O-lower alkyl,
—CH$_2$C(O)O-lower alky,
halogen and
lower alkyl,
or is phenyl,
benzyl,
heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl,
—(CH$_2$)$_m$-lower alkoxy or
—(CHR)$_m$—C(O)O-lower alkyl;
R'' is hydrogen,
cycloalkyl which is unsubstituted or substituted by one or more halogen atoms,
lower alkyl,
lower alkyl substituted by halogen,
lower alkyl substituted by hydroxy,
—(CH$_2$)$_m$-heterocycloalkyl, wherein heterocycloalkyl is selected from the group consisting of oxetanyl, tetrahydrofuranyl, tetrahydropyranyl, azetidinyl, pyrrolidinyl, piperidinyl, piperazinyl, morpholinyl and thiomorpholinyl,
—NR$_2$,
heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl,
benzyl or
—(CHR)$_m$—C(O)O-lower alkyl;
R is hydrogen or lower alkyl;
$R^6$ is hydrogen or lower alkyl;
X is —CHR—; and
m is 0, 1, 2 or 3;
or a pharmaceutically acceptable acid addition salt, optically pure enantiomer, racemate or diastereomeric mixture thereof.

2. A compound of formula II wherein
$R^1$ is aryl or is heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, each of which is unsubstituted or substituted by one or more substituents selected from the group consisting of halogen, $CF_3$, $OCF_3$, $NO_2$ and CN;
$R^2$, $R^3$, $R^4$, $R^{2'}$, $R^{3'}$, and $R^{4'}$ are each independently hydrogen, lower alkyl or $CF_3$;
$R^5$ is cycloalkyl, aryl or heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, wherein cycloalkyl, aryl or heteroaryl are unsubstituted or substituted by one or more substituents selected from the group consisting of
halogen,
lower alkyl,
CHO,
CN,
hydroxy,
lower alkyloxy,
lower alkinyloxy,
—OCF$_3$,
OCHF$_2$,
OCH$_2$F,
—OC(O)-lower alkyl,
—OC(O)—NR'R",
—O—(CH$_2$)$_n$-heterocycloalkyl wherein heterocycloalkyl is selected from the group consisting of oxetanyl, tetrahydrofuranyl, tetrahydropyranyl, azetidinyl, pyrrolidinyl, piperidinyl, piperazinyl, morpholinyl and thiomorpholinyl,
—O—(CH$_2$)$_n$-heteroaryl wherein heteroaryl is selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl which is unsubstituted or substituted by lower alkyl,
—O—(CH$_2$)$_n$-aryl,
—(CH$_2$)$_n$—C(O)NR'R",
—(CH$_2$)$_n$—C(O)O-lower alkyl,
—(CH$_2$)$_n$—C(O)OH,
—(CH$_2$)$_n$—C(O)O-lower alkinyl,
—C(O)-heterocycloalkyl wherein heterocycloalkyl is selected from the group consisting of oxetanyl, tetrahydrofuranyl, tetrahydropyranyl, azetidinyl, pyrrolidinyl, piperidinyl, piperazinyl, morpholinyl and thiomorpholinyl optionally substituted by COOH,
—C(O)-cycloalkyl,
—C(O)-aryl,
—NR'R",
nitro,
—S(O)$_2$-lower alkyl,
—S(O)$_2$-cycloalkyl,
—S(O)$_2$-heterocycloalkyl wherein heterocycloalkyl is selected from the group consisting of oxetanyl, tetrahydrofuranyl, tetrahydropyranyl, azetidinyl, pyrrolidinyl, piperidinyl, piperazinyl, morpholinyl and thiomorpholinyl,
—S(O)$_2$-aryl, and
—S(O)$_2$—NR'R",
or is

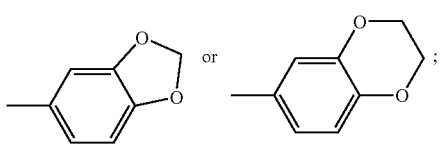

R' and R" are each independently hydrogen,
lower alkyl,
cycloalkyl,
heterocycloalkyl selected from the group consisting of oxetanyl, tetrahydrofuranyl, tetrahydropyranyl, azetidinyl, pyrrolidinyl, piperidinyl, piperazinyl, morpholinyl and thiomorpholinyl, heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl,
di-lower alkylamino,
—CH$_2$CF$_3$,
—CH$_2$CHF$_2$,
—CH$_2$CH$_2$F,
—C(O)-lower alkyl,
—C(O)O-lower alkyl or
—C(O)-cycloalkyl;
X is a bond, lower alkyl or lower alkenyl; and
n is 0, 1, 2 or 3;
or a pharmaceutically acceptable acid addition salt, optically pure enantiomer, racemate or diastereomeric mixture thereof.

3. A compound of claim 1, wherein
R$^1$ is phenyl substituted by halogen and R$^5$ is phenyl substituted by —C(O)—NR"$_2$.

4. A compound of claim 1, wherein R$^1$ is phenyl substituted by halogen or by lower alkyl substituted by halogen and R$^5$ is phenyl substituted by halogen, by lower alkyl substituted by halogen, by CH$_2$OH, or by halogen and lower alkoxy.

5. A compound of claim 1, wherein R$^1$ is phenyl substituted by halogen and R$^5$ is phenyl substituted by —(CR$_2$)$_m$—C(O)—R' or by —(CR$_2$)$_m$—C(O)—R' and halogen.

6. A compound of claim 1, wherein R$^1$ is phenyl substituted by halogen and R$^5$ is phenyl substituted by hydroxy.

7. A compound of claim 1, wherein R$^1$ is phenyl substituted by halogen and R$^5$ is phenyl substituted by NH$_2$.

8. A ompound of claim 1, wherein R$^1$ is heteroaryl, selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, unsubstituted or substituted by one or more substituents as described in claim 1.

9. A compound of claim 1, wherein X is —CH$_2$—.

10. A compound of claim 1, wherein R$^1$ is aryl and R$^5$ is aryl.

11. A pharmaceutical composition comprising a compound of formula I

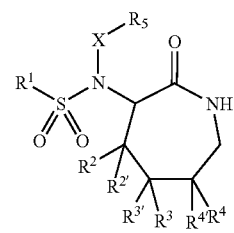

wherein
R$^1$ is aryl or is heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, each of which is unsubstituted or substituted by one or more substituents selected from the group consisting of
halogen,
lower alkyl,
lower alkyl substituted by halogen,
—O-lower alkyl substituted by halogen,
$NO_2$, and
CN;

$R^2$, $R^3$, $R^4$, $R^{2'}$, $R^{3'}$, and $R^{4'}$ are each independently hydrogen, lower alkyl, phenyl or lower alkyl substituted by halogen;

$R^5$ is aryl or is heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, each of which is unsubstituted or substituted by one or more substituents, selected from the group consisting of
halogen,
lower alkyl,
lower alkoxy,
CN,
nitro,
amino,
hydroxy,
lower alkyl substituted by hydroxy, and
lower alkyl substituted by halogen,
or is aryl or is heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, each of which is substituted by
—C(O)—$NR''_2$,
—$(CR_2)_m$—C(O)—R',
—$(CH_2)_m$-heterocycloalkyl,
—$(CH_2)_m$-heteroaryl wherein heteroaryl is selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl which is unsubstituted or substituted by —$(CH_2)_m$-lower alkoxy, lower alkyl, —$(CH_2)_m$—O-benzyl or $CH_2OH$,
—O—C(O)-lower alkyl,
—O—C(O)—$NR_2$,
—O—$(CH_2)_m$—C(O)OH,
—O-lower alkinyl,
—O-lower alkyl substituted by halogen,
—O—$(CH_2)_m$-heterocyclyl,
—O—$(CH_2)_m$-phenyl which is unsubstituted or substituted by hydroxy,
—O—$(CH_2)_m$-heteroaryl wherein heteroaryl is selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl which is unsubstituted or substituted by lower alkyl,
—$(CH_2)_m$—NH—C(O)R',
—$(CH_2)_m$—NH—$S(O)_2$—R',
—$S(O)_2$-lower alkyl,
—$S(O)_2$-heterocyclyl, or
—$S(O)_2$NH-cycloalkyl,
or is cycloalkyl;

R' is hydrogen,
lower alky,
lower alkinyloxy,
hydroxy,
cycloalkyl,
heterocycloalkyl selected from the group consisting of oxetanyl, tetrahydrofuranyl, tetrahydropyranyl, azetidinyl, pyrrolidinyl, piperidinyl, piperazinyl, morpholinyl and thiomorpholinyl, which is unsubstituted or substituted by one or more substituents selected from COOH, —C(O)O-lower alkyl, —$CH_2$C(O)O-lower alky, halogen and lower alkyl,
or is phenyl,
benzyl,
heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl,
—$(CH_2)_m$-lower alkoxy or
—$(CHR)_m$—C(O)O-lower alkyl;

R" is hydrogen,
cycloalkyl, which is unsubstituted or substituted by one or more halogen atoms,
lower alkyl,
lower alkyl substituted by halogen,
lower alkyl substituted by hydroxy,
—$(CH_2)_m$-heterocycloalkyl wherein heterocycloalkyl is selected from the group consisting of oxetanyl, tetrahydrofuranyl, tetrahydropyranyl, azetidinyl, pyrrolidinyl, piperidinyl, piperazinyl, morpholinyl and thiomorpholinyl,
—$NR_2$,
heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl,
benzyl or
—$(CHR)_m$—C(O)O-lower alkyl;

R is hydrogen or lower alkyl;
$R^6$ is hydrogen or lower alkyl;
X is —CHR—; and
m is 0, 1, 2 or 3;

or a pharmaceutically acceptable acid addition salt, optically pure enantiomer, racemate or diastereomeric mixture thereof and a pharmaceutically acceptable carrier.

12. A process for preparing a compound of formula I

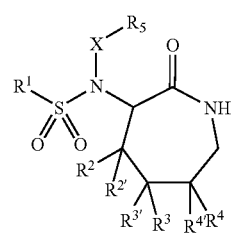

wherein
$R^1$ is aryl or is heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, each of which is unsubstituted or substituted by one or more substituents selected from the group consisting of
halogen,
lower alky,
lower alkyl substituted by halogen,
—O-lower alkyl substituted by halogen,
$NO_2$ and
CN;
$R^2$, $R^3$, $R^4$, $R^{2'}$, $R^{3'}$, and $R^{4'}$ are each independently lower alkyl, phenyl or lower alkyl substituted by halogen;
$R^5$ is aryl or is heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, each of which is unsubstituted or substituted by one or more substituents, selected from the group consisting of
halogen,
lower alkyl,
lower alkoxy,
CN,
nitro,
amino,
hydroxy,
lower alkyl substituted by hydroxy, and
lower alkyl substituted by halogen,
or is aryl or is heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, each of which is substituted by
—C(O)—NR'$_2$,
—(CR$_2$)$_m$—C(O)—R',
—(CH$_2$)$_m$-heterocycloalkyl,
—(CH$_2$)$_m$-heteroaryl wherein heteroaryl is selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, which is unsubstituted or substituted by —(CH$_2$)$_m$-lower alkoxy, lower alkyl, —(CH$_2$)$_m$—O-benzyl or CH$_2$OH,
—O—C(O)-lower alkyl,
—O—C(O)—NR$_2$,
—O—(CH$_2$)$_m$—C(O)OH,
—O-lower alkinyl,
—O-lower alkyl substituted by halogen,
—O—(CH$_2$)$_m$-heterocyclyl,
—O—(CH$_2$)$_m$-phenyl which is unsubstituted or substituted by hydroxy,
—O—(CH$_2$)$_m$-heteroaryl wherein heteroaryl is selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl, which is unsubstituted or substituted by lower alkyl,
—(CH$_2$)$_m$—NH—C(O)R',
—(CH$_2$)$_m$—NH—S(O)$_2$—R',
—S(O)$_2$-lower alkyl,
—S(O)$_2$-heterocyclyl, or
—S(O)$_2$NH-cycloalkyl,
or is cycloalkyl;
R' is hydrogen,
lower alkyl,
lower alkinyloxy,
hydroxy,
cycloalkyl,
heterocycloalkyl selected from the group consisting of oxetanyl, tetrahydrofuranyl, tetrahydropyranyl, azetidinyl, pyrrolidinyl, piperidinyl, piperazinyl, morpholinyl and thiomorpholinyl, which is unsubstituted or substituted by one or more substituents selected from
COOH,
—C(O)O-lower alkyl,
—CH$_2$C(O)O-lower alkyl,
halogen and
lower alkyl,
or is phenyl,
benzyl,
heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl,
—(CH$_2$)$_m$-lower alkoxy or
—(CHR)$_m$—C(O)O-lower alkyl;
R" is hydrogen,
cycloalkyl, which is unsubstituted or substituted by one or more halogen atoms,
lower alkyl,
lower alkyl substituted by halogen,
lower alkyl substituted by hydroxy,
—(CH$_2$)$_m$-heterocycloalkyl wherein heterocycloalkyl is selected from the group consisting of oxetanyl, tetrahydrofuranyl, tetrahydropyranyl, azetidinyl, pyrrolidinyl, piperidinyl, piperazinyl, morpholinyl and thiomorpholinyl,
—NR$_2$,
heteroaryl selected from the group consisting of pyridyl, pyrazinyl, pyrimidinyl, pyridazinyl, triazinyl, thiazolyl, thienyl, furyl, pyrrolyl, imidazolyl, pyrazolyl, isothiazolyl, tetrazolyl, [1,2,4]triazolyl, [1,2,4]oxadiazolyl, oxazolyl, indanyl, benzo[1,3]dioxolyl, benzofuranyl and isoxazolyl,
benzyl or
—(CHR)$_m$—C(O)O-lower alkyl;
R is hydrogen or lower alkyl;
$R^6$ is hydrogen or lower alkyl;
X is —CHR—; and
m is 0, 1, 2 or 3;
or a pharmaceutically acceptable acid addition salt, optically pure enantiomer, racemate or diastereomeric mixture thereof, wherein said process is selected from one of the following two processes which comprise
a) reacting a compound of formula

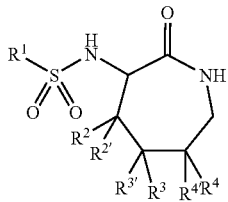

IV with a compound of formula
R⁵Xhal in the presence of a base, or
with a compound of formula
R⁵XOH in the presence of diethylazodicarboxylate and tripenylphosphine
to produce a compound of formula

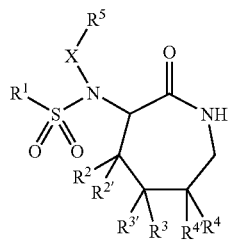

I wherein $R^1$-$R^5$ and X have the meaning as described in claim 1, and
b) reacting a compound of formula

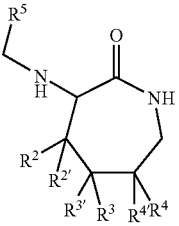

III with a compound of formula
$R^1$—S(O)$_2$—Cl in the presence of a base
to produce a compound of formula

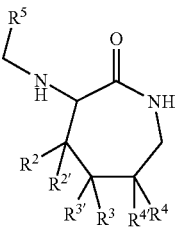

III

\* \* \* \* \*